(12) United States Patent
Gao et al.

(10) Patent No.: US 11,413,356 B2
(45) Date of Patent: Aug. 16, 2022

(54) METHODS AND COMPOSITIONS FOR TREATING METABOLIC IMBALANCE

(71) Applicant: University of Massachusetts, Boston, MA (US)

(72) Inventors: Guangping Gao, Westborough, MA (US); Dominic Gessler, Worcester, MA (US)

(73) Assignee: University of Massachusetts, Boston, MA (US)

( * ) Notice: Subject to any disclaimer, the term of this patent is extended or adjusted under 35 U.S.C. 154(b) by 776 days.

(21) Appl. No.: 16/093,813

(22) PCT Filed: Apr. 14, 2017

(86) PCT No.: PCT/US2017/027759
§ 371 (c)(1),
(2) Date: Oct. 15, 2018

(87) PCT Pub. No.: WO2017/181105
PCT Pub. Date: Oct. 19, 2017

(65) Prior Publication Data
US 2019/0125899 A1    May 2, 2019

Related U.S. Application Data

(60) Provisional application No. 62/323,587, filed on Apr. 15, 2016.

(51) Int. Cl.
| | | |
|---|---|---|
| *A61K 48/00* | (2006.01) | |
| *A61K 38/50* | (2006.01) | |
| *A61K 35/761* | (2015.01) | |
| *A61K 35/30* | (2015.01) | |
| *G01N 33/574* | (2006.01) | |
| *C12N 9/80* | (2006.01) | |
| *C12N 9/10* | (2006.01) | |
| *A61K 38/45* | (2006.01) | |
| *A61K 45/06* | (2006.01) | |

(52) U.S. Cl.
CPC .......... *A61K 48/0058* (2013.01); *A61K 35/30* (2013.01); *A61K 35/761* (2013.01); *A61K 38/45* (2013.01); *A61K 38/50* (2013.01); *A61K 45/06* (2013.01); *A61K 48/0075* (2013.01); *C12N 9/1029* (2013.01); *C12N 9/80* (2013.01); *C12Y 203/01017* (2013.01); *C12Y 305/01015* (2013.01); *G01N 33/574* (2013.01); *A01K 2227/105* (2013.01); *A01K 2267/035* (2013.01); *C12N 2750/14143* (2013.01)

(58) Field of Classification Search
CPC combination set(s) only.
See application file for complete search history.

(56) References Cited

U.S. PATENT DOCUMENTS

| | | |
|---|---|---|
| 5,478,745 A | 12/1995 | Samulski et al. |
| 5,871,982 A | 2/1999 | Wilson et al. |
| 6,156,303 A | 12/2000 | Russell et al. |
| 6,177,403 B1 | 1/2001 | Stedman |
| 6,251,677 B1 | 6/2001 | Wilson et al. |
| 6,485,966 B2 | 11/2002 | Gao et al. |
| 6,498,244 B1 | 12/2002 | Patel et al. |
| 6,544,786 B1 | 4/2003 | Xiao et al. |
| 6,620,800 B1 | 9/2003 | Roberts |
| 6,953,690 B1 | 10/2005 | Gao et al. |
| 6,962,815 B2 | 11/2005 | Bartlett |
| 7,022,519 B2 | 4/2006 | Gao et al. |
| 7,198,951 B2 | 4/2007 | Gao et al. |
| 7,235,393 B2 | 6/2007 | Gao et al. |
| 7,282,199 B2 | 10/2007 | Gao et al. |
| 7,427,396 B2 | 9/2008 | Arbetman et al. |
| 7,456,015 B2 | 11/2008 | Bohn et al. |
| 7,906,111 B2 | 3/2011 | Wilson et al. |
| 8,222,221 B2 | 7/2012 | Corey et al. |
| 8,524,446 B2 | 9/2013 | Gao et al. |
| 8,734,809 B2 | 5/2014 | Gao et al. |
| 9,217,155 B2 | 12/2015 | Gao et al. |
| 9,249,424 B2 | 2/2016 | Wolf et al. |
| 9,701,984 B2 | 7/2017 | Gao et al. |
| 2001/0016355 A1 | 8/2001 | Samulski et al. |
| 2002/0164783 A1 | 11/2002 | Feldhaus |
| 2002/0192823 A1 | 12/2002 | Bartlett |
| 2003/0103939 A1 | 6/2003 | Engelhardt et al. |

(Continued)

FOREIGN PATENT DOCUMENTS

| | | |
|---|---|---|
| EP | 2261242 A1 | 12/2010 |
| EP | 2468891 A2 | 6/2012 |

(Continued)

OTHER PUBLICATIONS

Seyfried et al., Targeting energy metabolism in brain cancer: review and hypothesis. Nutrition & Metabolism 2005, 2:30, p. 1-9 (Year: 2005).*
Extended European Search Report for Application No. EP 16858331.8, dated Jun. 4, 2019.
International Search Report and Written Opinion for Application No. PCT/US2016/058197, dated Jan. 24, 2017.
International Preliminary Report on Patentability for Application No. PCT/US2016/058197, dated May 3, 2018.
Aartsma-Rus et al., New insights in gene-derived therapy: the example of Duchenne muscular dystrophy. Ann NY Acad Sci. Dec. 2010;1214:199-212. doi: 10.1111/j.1749-6632.2010.05836.x. Epub Dec. 1, 2010.

(Continued)

*Primary Examiner* — Arthur S Leonard
(74) *Attorney, Agent, or Firm* — Wolf, Greenfield & Sacks, P.C.

(57) ABSTRACT

In some aspects, the disclosure relates to compositions and methods useful for the diagnosis and treatment of diseases associated with a metabolic imbalance in a subject (e.g., cancer). In some embodiments, the methods comprise administering to a subject an N-acetylaspartate (NAA)-depleting agent or an N-acetylaspartate (NAA)-increasing agent based upon the subject's metabolic profile.

18 Claims, 40 Drawing Sheets

Specification includes a Sequence Listing.

(56) References Cited

U.S. PATENT DOCUMENTS

| | | |
|---|---|---|
| 2003/0110526 A1 | 6/2003 | Brown et al. |
| 2003/0138772 A1 | 7/2003 | Gao et al. |
| 2003/0228282 A1 | 12/2003 | Gao et al. |
| 2004/0101514 A1 | 5/2004 | Liu et al. |
| 2004/0219528 A1 | 11/2004 | Morris et al. |
| 2005/0014262 A1 | 1/2005 | Gao et al. |
| 2005/0032219 A1 | 2/2005 | Aubourg et al. |
| 2005/0197313 A1 | 9/2005 | Roelvink |
| 2005/0255086 A1 | 11/2005 | Davidson et al. |
| 2005/0255089 A1 | 11/2005 | Chiorini et al. |
| 2005/0287122 A1 | 12/2005 | Bartlett et al. |
| 2006/0018841 A1 | 1/2006 | Arbetman et al. |
| 2006/0063174 A1 | 3/2006 | Turner et al. |
| 2006/0093589 A1 | 5/2006 | Warrington et al. |
| 2006/0153826 A1 | 7/2006 | Arnould et al. |
| 2006/0189564 A1 | 8/2006 | Burright et al. |
| 2006/0228800 A1 | 10/2006 | Lin et al. |
| 2006/0292117 A1 | 12/2006 | Loiler et al. |
| 2007/0036760 A1 | 2/2007 | Wilson et al. |
| 2007/0243526 A1 | 10/2007 | Kay et al. |
| 2007/0253936 A1 | 11/2007 | Kay et al. |
| 2008/0075737 A1 | 3/2008 | Gao et al. |
| 2008/0292595 A1 | 11/2008 | Arbetman et al. |
| 2009/0042828 A1 | 2/2009 | Xu et al. |
| 2009/0111766 A1 | 4/2009 | Atkinson et al. |
| 2009/0149409 A1 | 6/2009 | Bohn et al. |
| 2009/0197338 A1 | 8/2009 | Vandenberghe et al. |
| 2009/0215879 A1 | 8/2009 | DiPrimio et al. |
| 2009/0239240 A1 | 9/2009 | Chu |
| 2010/0104561 A1 | 4/2010 | Zhong et al. |
| 2010/0183570 A1 | 7/2010 | Wang et al. |
| 2010/0323001 A1 | 12/2010 | Pachuk |
| 2011/0171262 A1 | 7/2011 | Bakker et al. |
| 2011/0172293 A1 | 7/2011 | Fish et al. |
| 2011/0212520 A1 | 9/2011 | Davidson et al. |
| 2011/0258716 A1 | 10/2011 | Baltimore et al. |
| 2012/0077870 A1 | 3/2012 | Blanks et al. |
| 2012/0137379 A1 | 5/2012 | Gao et al. |
| 2012/0270930 A1 | 10/2012 | Van Der Maarel et al. |
| 2012/0309050 A1 | 12/2012 | Kumon et al. |
| 2013/0023488 A1 | 1/2013 | Wu |
| 2013/0030042 A1 | 1/2013 | Couto |
| 2013/0101558 A1 | 4/2013 | Gao et al. |
| 2013/0109742 A1 | 5/2013 | Hewitt et al. |
| 2013/0142861 A1 | 6/2013 | Tsou et al. |
| 2013/0195801 A1 | 8/2013 | Gao et al. |
| 2013/0323226 A1 | 12/2013 | Wilson et al. |
| 2013/0323229 A1 | 12/2013 | Leone et al. |
| 2014/0051601 A1 * | 2/2014 | Chinnaiyan ...... G01N 33/57434 506/12 |
| 2014/0142152 A1 | 5/2014 | Jaworski |
| 2014/0142161 A1 | 5/2014 | Flotte et al. |
| 2014/0142288 A1 | 5/2014 | Davidson et al. |
| 2014/0147418 A1 | 5/2014 | Chiorini et al. |
| 2014/0179770 A1 | 6/2014 | Zhang et al. |
| 2014/0201857 A1 | 7/2014 | Fahrenkrug et al. |
| 2014/0335054 A1 | 11/2014 | Gao et al. |
| 2015/0065560 A1 | 3/2015 | Bjorklund et al. |
| 2015/0160224 A1 | 6/2015 | Troyer |
| 2015/0258180 A1 | 9/2015 | Mahuran et al. |
| 2016/0017005 A1 | 1/2016 | Asokan et al. |
| 2016/0060624 A1 | 3/2016 | Davidson et al. |
| 2016/0076054 A1 | 3/2016 | Auricchio et al. |
| 2016/0153005 A1 | 6/2016 | Zhang et al. |
| 2016/0185832 A1 | 6/2016 | Drivas et al. |
| 2016/0194374 A1 | 7/2016 | Wijnholds et al. |
| 2016/0272976 A1 | 9/2016 | Kaspar |
| 2017/0029785 A1 | 2/2017 | Zhao et al. |
| 2017/0114340 A1 | 4/2017 | Mueller et al. |
| 2017/0165377 A1 | 6/2017 | Gao et al. |
| 2017/0166927 A1 | 6/2017 | Gao et al. |
| 2018/0311323 A1 | 11/2018 | Gao et al. |

FOREIGN PATENT DOCUMENTS

| | | | |
|---|---|---|---|
| JP | 2008-538286 | 10/2008 | |
| WO | 2003/042397 | 5/2003 | |
| WO | WO 2004/108922 A2 | 12/2004 | |
| WO | 2005/033321 | 4/2005 | |
| WO | 2006/031267 A2 | 3/2006 | |
| WO | 2006/066066 A2 | 6/2006 | |
| WO | 2006/119432 A2 | 11/2006 | |
| WO | 2008/125846 A2 | 10/2008 | |
| WO | WO 2008/150897 A2 | 12/2008 | |
| WO | WO 2009/043936 | 4/2009 | |
| WO | WO 2009/146178 A1 | 12/2009 | |
| WO | WO 2010/027446 A2 | 3/2010 | |
| WO | WO 2010/071454 A1 | 6/2010 | |
| WO | WO-2010071832 A1 * | 6/2010 | ............ A61P 21/00 |
| WO | WO 2010/099383 A2 | 9/2010 | |
| WO | WO 2010/129021 A1 | 11/2010 | |
| WO | WO 2010/138263 A2 | 12/2010 | |
| WO | WO 2011/094198 A1 | 8/2011 | |
| WO | WO 2011/133890 A1 | 10/2011 | |
| WO | WO 2012/123430 A1 | 9/2012 | |
| WO | WO 2013/055865 A1 | 4/2013 | |
| WO | WO 2013/123503 A1 | 8/2013 | |
| WO | WO 2013/170078 A1 | 11/2013 | |
| WO | WO 2013/181446 A2 | 12/2013 | |
| WO | WO 2013/190059 A1 | 12/2013 | |
| WO | WO 2014/160092 A1 | 10/2014 | |
| WO | WO 2014/186746 A1 | 11/2014 | |
| WO | WO 2014/197748 A2 | 12/2014 | |
| WO | WO 2015/121501 A1 | 8/2015 | |
| WO | WO 2015/127128 A2 | 8/2015 | |
| WO | WO 2015/164786 | 10/2015 | |
| WO | WO 2015/168666 A2 | 11/2015 | |
| WO | WO 2016/065001 A1 | 4/2016 | |
| WO | WO 2017/023724 A1 | 2/2017 | |

OTHER PUBLICATIONS

Afione et al., In vivo model of adeno-associated virus vector persistence and rescue. J Virol. May 1996;70(5):3235-41.

Berns et al., Detection of adeno-associated virus (AAV)-specific nucleotide sequences in DNA isolated from latently infected Detroit 6 cells. Virology. Dec. 1975;68(2):556-60.

Brantly et al., Phase I trial of intramuscular injection of a recombinant adeno-associated virus serotype 2 alpha1-antitrypsin (AAT) vector in AAT-deficient adults. Hum Gene Ther. Dec. 2006;17(12):1177-86.

Chen et al., Efficient transduction of vascular endothelial cells with recombinant adeno-associated virus serotype 1 and 5 vectors. Hum Gene Ther. Feb. 2005;16(2):235-47.

Chirmule et al., Humoral immunity to adeno-associated virus type 2 vectors following administration to murine and nonhuman primate muscle. J Virol. Mar. 2000;74(5):2420-5.

Conrad et al., Safety of single-dose administration of an adeno-associated virus (AAV)-CFTR vector in the primate lung. Gene Ther. Aug. 1996;3(8):658-68.

Davidson et al., Recombinant adeno-associated virus type 2, 4, and 5 vectors: transduction of variant cell types and regions in the mammalian central nervous system. Proc Natl Acad Sci U S A. Mar. 28, 2000;97(7):3428-32.

Dominov et al., A novel dysferlin mutant pseudoexon bypassed with antisense oligonucleotides. Ann Clin Transl Neurol. Sep. 2014;1(9):703-20. doi: 10.1002/acn3.96. Epub Sep. 27, 2014.

Ehlert et al., Cellular toxicity following application of adeno-associated viral vector-mediated RNA interference in the nervous system. BMC Neurosci. Feb. 18, 2010;11:20.

Fischer et al., Successful transgene expression with serial doses of aerosolized rAAV2 vectors in rhesus macaques. Mol Ther. Dec. 2003;8(6):918-26.

Flotte, Recombinant adeno-associated virus (AAV) gene therapy vectors for, cystic fibrosis (CF), alpha-1-antitrypsin deficiency (AAT) and fatty oxidation disorders (FAO). Umass Medical School. Interdisciplinary Graduate Program. Last accessed at http://www.umassmed.edu/igp/faculty/flotte.cfm?start=0& on Aug. 27, 2009.

(56) References Cited

OTHER PUBLICATIONS

Gao et al., Biology of AAV serotype vectors in liver-directed gene transfer to nonhuman primates. Mol Ther. Jan. 2006;13(1):77-87. Epub Oct. 10, 2005.
Gao et al., Clades of Adeno-associated viruses are widely disseminated in human tissues. J Virol. Jun. 2004;78(12):6381-8.
Gao et al., Erythropoietin gene therapy leads to autoimmune anemia in macaques. Blood. May 1, 2004;103(9):3300-2. Epub Dec. 24, 2003.
Gessler et al., Optimized AspA Expression Cassette Dramatically Improves Therapeutic Potency of Systemically Delivered rAAV in CNS Gene Therapy of Canavan's Disease. Mol Ther. May 2014;22(Suppl 1):S111. 1 page.
Grimm et al., Fatality in mice due to oversaturation of cellular microRNA/short hairpin RNA pathways. Nature. May 25, 2006;441(7092):537-41.
Hauswirth et al., Treatment of leber congenital amaurosis due to RPE65 mutations by ocular subretinal injection of adeno-associated virus gene vector: short-term results of a phase I trial. Hum Gene Ther. Oct. 2008;19(10):979-90.
Iwamoto et al., Global diffuse distribution in the brain and efficient gene delivery to the dorsal root ganglia by intrathecal injection of adeno-associated viral vector serotype 1. J Gene Med. Jun. 2009;11(6):498-505. doi: 10.1002/jgm.1325.
Jakobsson et al., Lentiviral vectors for use in the central nervous system. Mol Ther. Mar. 2006;13(3):484-93. Epub Jan. 3, 2006.
Kaspar et al., Retrograde viral delivery of IGF-1 prolongs survival in a mouse ALS model. Science. Aug. 8, 2003;301(5634):839-42.
Kota et al., AAV8-Mediated Delivery of miR-26a inhibits cancer cell proliferation and induces tumor-specific apoptosis in a liver cancer model. Mol. Therapy. May 2009. 17(1):S300. Abstract 783.
Kumar et al., Lack of aspartoacylase activity disrupts survival and differentiation of neural progenitors and oligodendrocytes in a mouse model of Canavan disease. J Neurosci Res. Nov. 15, 2009;87(15):3415-27. doi: 10.1002/jnr.22233.
Lebherz et al., Gene therapy with novel adeno-associated virus vectors substantially diminishes atherosclerosis in a murine model of familial hypercholesterolemia. J Gene Med. Jun. 2004;6(6):663-72.
Li et al., Ex vivo transduction and transplantation of bone marrow cells for liver gene delivery of alpha 1-antitrypsin. Mol Ther. Aug. 2010;18(8):1553-8. Epub Jun. 15, 2010.
Liu et al., Biological Differences in rAAV Transduction of Airway Epithelia in Humans and in Old World Non-human Primates. Mol Ther. Dec. 2007;15(12):2114-23. Epub Jul. 31, 2007.
Liu et al., Comparative biology of rAAV transduction in ferret, pig and human airway epithelia. Gene Ther. Nov. 2007;14(21):1543-8. Epub Aug. 30, 2007.
Liu et al., Species-specific differences in mouse and human airway epithelial biology of recombinant adeno-associated virus transduction. Am J Respir Cell Mol Biol. Jan. 2006;34(1):56-64. Epub Sep. 29, 2005.
Loiler et al., Targeting recombinant adeno-associated virus vectors to enhance gene transfer to pancreatic islets and liver. Gene Ther. Sep. 2003;10(18):1551-8.
Mandel et al., Recombinant adeno-associated viral vectors as therapeutic agents to treat neurological disorders. Mol Ther. Mar. 2006;13(3):463-83. Epub Jan. 18, 2006.
Manno et al., Successful transduction of liver in hemophilia by AAV-Factor IX and limitations imposed by the host immune response. Nat Med. Mar. 2006;12(3):342-7. Epub Feb. 12, 2006. Erratum in: Nat Med. May 2006;12(5):592. Rasko, John [corrected to Rasko, John JE]; Rustagi, Pradip K [added].
Mattan et al., Aspartoacylase deficiency affects early postnatal development of oligodendrocytes and myelination. Neurobiol Dis. Nov. 2010;40(2):432-43. doi: 10.1016/j.nbd.2010.07.003. Epub Jul. 14, 2010.
Meijer et al., Controlling brain tumor growth by intraventricular administration of an AAV vector encoding IFN-beta. Cancer Gene Ther. Aug. 2009;16(8):664-71. doi: 10.1038/cgt.2009.8. Epub Feb. 6, 2009.
Mingozzi et al., CD8(+) T-cell responses to adeno-associated virus capsid in humans. Nat Med. Apr. 2007;13(4):419-22. Epub Mar. 18, 2007.
Moffett et al., N-Acetylaspartate in the CNS: from neurodiagnostics to neurobiology. Prog Neurobiol. Feb. 2007;81(2):89-131. Epub Jan. 5, 2007.
Moss et al., Repeated adeno-associated virus serotype 2 aerosol-mediated cystic fibrosis transmembrane regulator gene transfer to the lungs of patients with cystic fibrosis: a multicenter, double-blind, placebo-controlled trial. Chest. Feb. 2004;125(2):509-21.
Mueller et al., In Vivo AAV Delivered Allele Specific shRNA for the Knockdown of Alpha-1 Antitrypsin. Molecular Therapy May 2010;18(1):S22. Abstract 53.
Mueller et al., Sustained miRNA-mediated knockdown of mutant AAT with simultaneous augmentation of wild-type AAT has minimal effect on global liver miRNA profiles. Mol Ther. Mar. 2012;20(3):590-600. Epub Jan. 17, 2012.
Mueller et al., The pros and cons of immunomodulatory IL-10 gene therapy with recombinant AAV in a Cftr-/--dependent allergy mouse model. Gene Ther. Feb. 2009;16(2):172-83. Epub Sep. 25, 2008.
Mueller et al., Using rAAV Delivered miRNAs to Knockdown Misfolded Human Alpha 1 Antitrypsin in a Transgenic Mouse Model. Molecular Therapy May 2010;18(1):S21. Abstract 51.
Parikh et al., A clinical approach to the diagnosis of patients with leukodystrophies and genetic leukoencephelopathies. Mol Genet Metab. Apr. 2015;114(4):501-515. doi: 10.1016/j.ymgme.2014.12. 434. Epub Dec. 29, 2014.
Pertin et al., Efficacy and specificity of recombinant adeno-associated virus serotype 6 mediated gene transfer to drg neurons through different routes of delivery. Poster sessions. Eur J. Pain. 2009;13:S74. Abstract 229.
Scallan et al., Human immunoglobulin inhibits liver transduction by AAV vectors at low AAV2 neutralizing titers in SCID mice. Blood. Mar. 1, 2006;107(5):1810-7. Epub Oct. 25, 2005.
Sondhi et al., Enhanced survival of the LINCL mouse following CLN2 gene transfer using the rh.10 rhesus macaque-derived adeno-associated virus vector. Mol Ther. Mar. 2007;15(3):481-91. Epub Dec. 19, 2006.
Song et al., Intramuscular administration of recombinant adeno-associated virus 2 alpha-1 antitrypsin (rAAV-SERPINA1) vectors in a nonhuman primate model: safety and immunologic aspects. Mol Ther. Sep. 2002;6(3):329-35.
Storkebaum et al., Treatment of motoneuron degeneration by intracerebroventricular delivery of VEGF in a rat model of ALS. Nat Neurosci. Jan. 2005;8(1):85-92. Epub Nov. 28, 2004.
Tenenbaum et al., Recombinant AAV-mediated gene delivery to the central nervous system. J Gene Med. Feb. 2004;6 Suppl 1:S212-22.
Uniprot Submission; Accession No. A8IGP7; Nov. 13, 2013.
Uniprot Submission; Accession No. H3GK32; Feb. 6, 2013.
Uniprot Submission; Accession No. T2BRA8; Nov. 13, 2013.
Virella-Lowell et al., Enhancing rAAV vector expression in the lung. J Gene Med. Jul. 2005;7(7):842-50.
Vulchanova et al., Differential adeno-associated virus mediated gene transfer to sensory neurons following intrathecal delivery by direct lumbar puncture. Mol Pain. May 28, 2010;6:31. doi: 10.1186/1744-8069-6-31.
Wang et al., Neuroprotective effects of glial cell line-derived neurotrophic factor mediated by an adeno-associated virus vector in a transgenic animal model of amyotrophic lateral sclerosis. J Neurosci. Aug. 15, 2002;22(16):6920-8.
Wang et al., Sustained correction of disease in naive and AAV2-pretreated hemophilia B dogs: AAV2/8-mediated, liver-directed gene therapy. Blood. Apr. 15, 2005;105(8):3079-86. Epub Jan. 6, 2005.
Wang et al., The design of vectors for RNAi delivery system. Curr Pharm Des. 2008;14(13):1327-40.
Wang et al., Therapeutic gene silencing delivered by a chemically modified small interfering RNA against mutant SOD1 slows amyo-

(56) References Cited

OTHER PUBLICATIONS trophic lateral sclerosis progression. J Biol Chem. Jun. 6, 2008;283(23):15845-52. doi: 10.1074/jbc.M800834200. Epub Mar. 26, 2008.
Watson et al., Intrathecal administration of AAV vectors for the treatment of lysosomal storage in the brains of MPS I mice. Gene Ther. Jun. 2006;13(11):917-25.
Wein et al., Efficient bypass of mutations in dysferlin deficient patient cells by antisense-induced exon skipping. Hum Mutat. Feb. 2010;31(2):136-42. doi: 10.1002/humu.21160.
Zabner et al., Adeno-associated virus type 5 (AAV5) but not AAV2 binds to the apical surfaces of airway epithelia and facilitates gene transfer. J Virol. Apr. 2000;74(8):3852-8.
Adachi et al., Drawing a high-resolution functional map of adeno-associated virus capsid by massively parallel sequencing. Nat Commun. 2014;5:3075. doi: 10.1038/ncomms4075.
Ahmed et al., A Single Intravenous rAAV Injection as Late as P20 Achieves Efficacious and Sustained CNS Gene Therapy in Canavan Mice. Mol Ther. Jul. 2, 2013. doi: 10.1038/mt.2013.138. [Epub ahead of print].
Akache et al., The 37/67-kilodalton laminin receptor is a receptor for adeno-associated virus serotypes 8, 2, 3, and 9. J Virol. Oct. 2006;80(19):9831-6.
Arbetman et al., Novel caprine adeno-associated virus (AAV) capsid (AAV-Go. 1) is closely related to the primate AAV-5 and has unique tropism and neutralization properties. J Virol. Dec. 2005;79(24):15238-45.
Arbuthnot et al., Hepatic delivery of RNA interference activators for therapeutic application. Curr Gene Ther. Apr. 2009;9(2):91-103.
Asokan et al., The AAV vector toolkit: poised at the clinical crossroads. Mol Ther. Apr. 2012;20(4):699-708. doi: 10.1038/mt. 2011.287. Epub Jan. 24, 2012.
Baek et al., AAV-mediated gene delivery in adult GM 1-gangliosidosis mice corrects lysosomal storage in CNS and improves survival. PLoS One. Oct. 18, 2010;5(10):e13468. doi: 10.1371/journal.pone. 0013468.
Bals et al., Transduction of well-differentiated airway epithelium by recombinant adeno-associated virus is limited by vector entry. J Virol. Jul. 1999;73(7):6085-8.
Berns et al., Biology of adeno-associated virus. Curr Top Microbiol Immunol. 1996;218:1-23.
Beutler et al., AAV for pain: steps towards clinical translation. Gene Ther. Apr. 2009;16(4):461-9. Epub Mar. 5, 2009.
Bish et al., Adeno-associated virus (AAV) serotype 9 provides global cardiac gene transfer superior to AAV1, AAV6, AAV7, and AAV8 in the mouse and rat. Hum Gene Ther. Dec. 2008;19(12):1359-68. doi: 10.1089/hum.2008.123.
Borel et al., Recombinant AAV as a platform for translating the therapeutic potential of RNA interference. Mol Ther. Apr. 2014;22(4):692-701. doi:10.1038/mt.2013.285. Epub Dec. 19, 2013.
Bourdenx et al., Systemic gene delivery to the central nervous system using Adeno-associated virus. Front Mol Neurosci. Jun. 2, 2014;7:50. doi: 10.3389/fnmol.2014.00050. eCollection 2014.
Buning et al., Receptor targeting of adeno-associated virus vectors. Gene Ther. Jul. 2003;10(14):1142-51.
Calcedo et al., Worldwide epidemiology of neutralizing antibodies to adeno-associated viruses. J Infect Dis. Feb. 1, 2009;199(3):381-90.
Carter et al., Adeno-associated virus gene expression and regulation. CRC Handbook of parvoviruses. 1990:227-54.
Carter, in "Handbook of Parvoviruses", ed., P. Tijsser, CRC Press, pp. 155-168 (1990).
Cearley et al., Expanded repertoire of AAV vector serotypes mediate unique patterns of transduction in mouse brain. Mol Ther. Oct. 2008;16(10):1710-8. doi: 10.1038/mt.2008.166. Epub Aug. 19, 2008.
Cearley et al., Transduction characteristics of adeno-associated virus vectors expressing cap serotypes 7, 8, 9, and Rh10 in the mouse brain. Mol Ther. Mar. 2006;13(3):528-37. Epub Jan. 18, 2006.
Chadderton et al., Improved retinal function in a mouse model of dominant retinitis pigmentosa following AAV-delivered gene therapy. Mol Ther. Apr. 2009;17(4):593-9. Epub Jan. 27, 2009.
Chen et al., Comparative study of anti-hepatitis B virus RNA interference by double-stranded adeno-associated virus serotypes 7, 8, and 9. Mol Ther. Feb. 2009;17(2):352-9. Epub Dec. 9, 2008.
Chen et al., Molecular signatures of disease brain endothelia provide new sites for CNS-directed enzyme therapy. Nat Med. Oct. 2009;15(10):1215-8. doi: 10.1038/nm.2025. Epub Sep. 13, 2009.
Cheng et al., Development of optimized AAV3 serotype vectors: mechanism of high-efficiency transduction of human liver cancer cells. Gene Ther. Apr. 2012;19(4):375-84. doi: 10.1038/gt.2011. 105. Epub Jul. 21, 2011.
Chiorini et al., Cloning and characterization of adeno-associated virus type 5. J Virol. Feb. 1999;73(2):1309-19.
Choudhury et al., Identification of Novel vectors capable of CNS transduction in adult mice after single round selection using DNA shuffled AAV capsid library. Mol Ther. May 1, 2013;21(1):S1/.
Cideciyan et al., Human RPE65 gene therapy for Leber congenital amaurosis: persistence of early visual improvements and safety at 1 year. Hum Gene Ther. Sep. 2009;20(9):999-1004.
Conlon et al., Efficient hepatic delivery and expression from a recombinant adeno-associated virus 8 pseudotyped alpha1-antitrypsin vector. Mol Ther. Nov. 2005;12(5):867-75. Epub Aug. 8, 2005.
Conlon et al., Ribozyme Approaches towards Down-Regulation of Pi*Z Mutant Human a-1 Anti-Trypsin. Mol. Therapy. 2004;9:S333. Abstract 875.
Cruz et al., In vivo post-transcriptional gene silencing of alpha-1 antitrypsin by adeno-associated virus vectors expressing siRNA. Lab Invest. Sep. 2007;87(9):893-902. Epub Jun. 25, 2007.
Cruz et al., The promise of gene therapy for the treatment of alpha-1 antitrypsin deficiency. Pharmacogenomics. Sep. 2007;8(9):1191-8.
Davidoff et al., Sex significantly influences transduction of murine liver by recombinant adeno-associated viral vectors through an androgen-dependent pathway. Blood. Jul. 15, 2003;102(2):480-8. Epub Mar. 13, 2003.
Daya et al., Gene therapy using adeno-associated virus vectors. Clin Microbiol Rev. Oct. 2008;21(4):583-93. doi: 10.1128/CMR.00008-08.
Duque et al., Intravenous administration of self-complementary AAV9 enables transgene delivery to adult motor neurons. Mol Ther. Jul. 2009;17(7):1187-96. doi: 10.1038/mt.2009.71. Epub Apr. 14, 2009.
Fechner et al., Cardiac-targeted RNA interference mediated by an AAV9 vector improves cardiac function in coxsackievirus B3 cardiomyopathy. J Mol Med (Berl). Sep. 2008;86(9):987-97. doi: 10.1007/s00109-008-0363-x. Epub Jun. 12, 2008.
Feigin et al., Modulation of metabolic brain networks after subthalamic gene therapy for Parkinson's disease. Proc Natl Acad Sci U S A. Dec. 4, 2007;104(49):19559-64. Epub Nov. 27, 2007.
Fisher et al., Transduction with recombinant adeno-associated virus for gene therapy is limited by leading-strand synthesis. J Virol. Jan. 1996;70(1):520-32.
Flotte et al., Gene therapy for alpha-1 antitrypsin deficiency. Hum Mol Genet. Apr. 15, 2011;20(R1):R87-92. doi: 10.1093/hmg/ddr156. Epub Apr. 16, 2011.
Flotte et al., Phase I trial of intramuscular injection of a recombinant adeno-associated virus alpha 1-antitrypsin (rAAV2-CB-hAAT) gene vector to AAT-deficient adults. Hum Gene Ther. Jan. 2004;15(1):93-128.
Foust et al., Intravascular AAV9 preferentially targets neonatal-neurons and adult-astrocytes. Nature Biotechnology, 27; 59-65 2009.
Foust et al., Over the barrier and through the blood: to CNS delivery we go. Cell Cycle. Dec. 15, 2009;8(24):4017-8.
Fraldi et al., Functional correction of CNS lesions in an MPS-IIIA mouse model by intracerebral AAV-mediated delivery of sulfamidase and SUMF1 genes. Hum Mol Genet. Nov. 15, 2007;16(22):2693-702. Epub Aug. 27, 2007.

(56) References Cited

OTHER PUBLICATIONS

Fu et al., Self-complementary adeno-associated virus serotype 2 vector: global distribution and broad dispersion of AAV-mediated transgene expression in mouse brain. Mol Ther. Dec. 2003;8(6):911-7.
Gadalla et al., Improved survival and reduced phenotypic severity following AAV9/MECP2 gene transfer to neonatal and juvenile male Mecp2 knockout mice. Mol Ther. Jan. 2013;21(1):18-30. doi:10.1038/mt.2012.200. Epub Sep. 25, 2012.
Gao et al., Adeno-associated viruses undergo substantial evolution in primates during natural infections. Proc Natl Acad Sci U S A. May 13, 2003;100(10):6081-6. Epub Apr. 25, 2003.
Gao et al., Adeno-associated virus-mediated gene transfer to non-human primate liver can elicit destructive transgene-specific T cell responses. Hum Gene Ther. Sep. 2009;20(9):930-42. doi: 10.1089/hum.2009.060.
Gao et al., Inadvertent gene transfer of co-packaged rep and cap sequences during the production of AAV vector and its potential impact on vector performance. Molecular Therapy. May 2008;16(Suppl. 1):S105-S106. Abstract 279.
Gao et al., New recombinant serotypes of AAV vectors. Curr Gene Ther. Jun. 2005;5(3):285-97.
Gao et al., Novel adeno-associated viruses from rhesus monkeys as vectors for human gene therapy. Proc Natl Acad Sci U S A. Sep. 3, 2002;99(18):11854-9. Epub Aug. 21, 2002.
Gao et al., RAAV-mediated targeting in adult mice and its potential in generating animal models of tissue-specific somatic transgenics or knock down. Molecular Therapy. May 2008;16(1):S118-S119. Abstract 316.
Genbank Submission; Accession No. ADZ26851; Wilson et al.; Jun. 30, 2005.
Genbank Submission; Accession No. AF028705.1; Rutledge et al.; Jan. 12, 1998.
Genbank Submission; NCBI, Accession No. AAB95450; Rutledge et al.; Jan. 12, 1998.
Genbank Submission; NCBI, Accession No. AAS99264; Gao et al.; Jun. 24, 2004.
Genbank Submission; NCBI, Accession No. ABA71701; Schmidt et al.; May 10, 2006.
Genbank Submission; NCBI, Accession No. ACB55301; Vandenberghe et al.; Jul. 31, 2008.
Genbank Submission; NCBI, Accession No. ACB55310; Vandenberghe et al.; Jul. 31, 2008.
Genbank Submission; NCBI, Accession No. AY530579.10; 2004.
Genbank Submission; NCBI, Accession No. NP_049542; Xiao et al.; Mar. 11, 2010.
Genbank Submission; NCBI, Accession No. YP_680426; Ruffing et al.; Nov. 19, 2010.
Grimm, Small silencing RNAs: state-of-the-art. Adv Drug Deliv Rev. Jul. 25, 2009;61(9):672-703. doi: 10.1016/j.addr.2009.05.002. Epub May 7, 2009.
Hernandez et al., Latent adeno-associated virus infection elicits humoral but not cell-mediated immune responses in a nonhuman primate model. J Virol. Oct. 1999;73(10):8549-58.
Hildinger et al., Hybrid vectors based on adeno-associated virus serotypes 2 and 5 for muscle-directed gene transfer. J Virol. Jul. 2001;75(13):6199-203.
Iida et al., Systemic Delivery of Tyrosine-Mutant AAV Vectors Results in Robust Transduction of Neurons in Adult Mice. BioMed Res Int. 2013;2013.
Janson et al., Clinical protocol. Gene therapy of Canavan disease: AAV-2 vector for neurosurgical delivery of aspartoacylase gene (ASPA) to the human brain. Hum Gene Ther. Jul. 20, 2002;13(11):1391-412.
Koornneef et al., Apolipoprotein B knockdown by AAV-delivered shRNA lowers plasma cholesterol in mice. Mol Ther. Apr. 2011;19(4):731-40. doi:10.1038/mt.2011.6. Epub Feb. 8, 2011.
Kotin et al., Organization of adeno-associated virus DNA in latently infected Detroit 6 cells. Virology. Jun. 1989;170(2):460-7.

Kotin et al., Site-specific integration by adeno-associated virus. Proc Natl Acad Sci U S A. Mar. 1990;87(6):2211-5.
Lawlor et al., Efficient gene delivery and selective transduction of glial cells in the mammalian brain by AAV serotypes isolated from nonhuman primates. Mol Ther. Oct. 2009;17(10):1692-702. doi:10.1038/mt.2009.170.
Leone et al., Aspartoacylase gene transfer to the mammalian central nervous system with therapeutic implications for Canavan disease. Ann Neurol. Jul. 2000;48(1):27-38. Erratum in: Ann Neurol Sep. 2000;48(3):398. Bilianuk L [corrected to Bilaniuk L].
Li et al., Efficient and Targeted Transduction of Nonhuman Primate Liver With Systemically Delivered Optimized AAV3B Vectors. Mol Ther. Dec. 2015;23(12):1867-76. doi: 10.1038/mt.2015.174. Epub Sep. 25, 2015.
Li et al., Protein trans-splicing as a means for viral vector-mediated in vivo gene therapy. Hum Gene Ther. Sep. 2008;19(9):958-64. doi: 10.1089/hum.2008.009.
Lin et al., Impact of preexisting vector immunity on the efficacy of adeno-associated virus-based HIV-1 Gag vaccines. Hum Gene Ther. Jul. 2008;19(7):663-9.
Lowenstein, Crossing the rubicon. Nat Biotechnol. Jan. 2009;27(1):42-4.
Lux et al., Green fluorescent protein-tagged adeno-associated virus particles allow the study of cytosolic and nuclear trafficking. J Virol. Sep. 2005;79(18):11776-87.
Ma et al., Therapeutic silencing of miR-10b inhibits metastasis in a mouse mammary tumor model. Nat Biotechnol. Apr. 2010;28(4):341-7. doi: 10.1038/nbt.1618. Epub Mar. 28, 2010.
Maguire et al., Directed evolution of adeno-associated virus for glioma cell transduction. J Neurooncol. Feb. 2010;96(3):337-47. doi:10.1007/s11060-009-9972-7. Epub Jul. 19, 2009.
Maguire et al., Gene therapy for the nervous system: challenges and new strategies. Neurotherapeutics. Oct. 2014;11(4):817-39. doi: 10.1007/s13311-014-0299-5.
Manfredsson et al., AAV9: a potential blood-brain barrier buster. Mol Ther. Mar. 2009;17(3):403-5.
Matalon et al., Adeno-associated virus-mediated aspartoacylase gene transfer to the brain of knockout mouse for canavan disease. Mol Ther. May 2003;7(5 Pt 1):580-7.
McCarty et al., Adeno-associated virus terminal repeat (TR) mutant generates self-complementary vectors to overcome the rate-limiting step to transduction in vivo. Gene Ther. Dec. 2003;10(26):2112-8.
McCarty et al., Integration of adeno-associated virus (AAV) and recombinant AAV vectors. Annu Rev Genet. 2004;38:819-45.
McCarty et al., Self-complementary recombinant adeno-associated virus (scAAV) vectors promote efficient transduction independently of DNA synthesis. Gene Ther. Aug. 2001;8(16):1248-54.
Mccarty, Self-complementary AAV vectors; advances and applications. Mol Ther. Oct. 2008;16(10):1648-56. Epub Aug. 5, 2008.
McCurdy et al., Sustained normalization of neurological disease after intracranial gene therapy in a feline model. Sci Transl Med. Apr. 9, 2014;6(231):231ra48. doi: 10.1126/scitranslmed.3007733.
Mietzsch et al., OneBac 2.0: Sf9 Cell Lines for Production of AAV5 Vectors with Enhanced Infectivity and Minimal Encapsidation of Foreign DNA. Hum Gene Ther. Oct. 2015;26(10):688-97. doi:10.1089/hum.2015.050. Epub Aug. 6, 2015.
Mueller et al., Development of Simultaneous Gene Augmentation and Reduction of Mutant Gene Expression with a Single Recombinant AAV for Alpha-1 Antitrypsin Disease. Molecular Therapy May 2009;17(1):S391-S392. Abstract 1030.
Mueller et al., In Vivo Allele Specific Knockdown of Mutant Alpha-1 Antitrypsin Using Recombinant AAV Delivered shRNA. Molecular Therapy May 2009;17(1):S313. Abstract 817.
NCBI Blast Protein Sequence. RID-09JSKF33114. Alignment of Seq ID Nos. 87, 179. 2016.
O'reilly et al., RNA interference-mediated suppression and replacement of human rhodopsin in vivo. Am J Hum Genet. Jul. 2007;81(1):127-35. Epub May 23, 2007.
Passini et al., CNS-targeted gene therapy improves survival and motor function in a mouse model of spinal muscular atrophy. J Clin Invest. Apr. 2010;120(4):1253-64. doi: 10.1172/JCI41615. Epub Mar. 15, 2010.

(56) References Cited

OTHER PUBLICATIONS

Pfeifer et al., Pharmacological potential of RNAi—focus on miRNA. Pharmacol Ther. Jun. 2010;126(3):217-27. doi: 10.1016/j.pharmthera. 2010.03.006. Epub Apr. 11, 2010.
Schattgen et al., Cutting Edge: DNA in the Lung Microenvironment during Influenza Virus Infection Tempers Inflammation by Engaging the DNA Sensor AIM2. J Immunol. Jan. 1, 2016;196(1):29-33. doi: 10.4049/jimmunol.1501048.
Schnepp et al., Characterization of adeno-associated virus genomes isolated from human tissues. J Virol. Dec. 2005;79(23):14793-803.
Seiler et al., Adeno-associated virus types 5 and 6 use distinct receptors for cell entry. Hum Gene Ther. Jan. 2006;17(1):10-9.
Snyder et al., Comparison of adeno-associated viral vector serotypes for spinal cord and motor neuron gene delivery. Hum Gene Ther. Sep. 2011;22(9):1129-35. doi: 10.1089/hum.2011.008. Epub Jul. 25, 2011.
Stoica et al., Targeting Human SOD1 Using AAV mediated RNAi in a mouse model of amyotrophic lateral sclerosis. Mol ther. Jun. 2013;21(1):S149.
Storek et al., Intrathecal long-term gene expression by self-complementary adeno-associated virus type 1 suitable for chronic pain studies in rats. Mol Pain. Jan. 30, 2006;2:4.
Tomar et al., Use of adeno-associated viral vector for delivery of small interfering RNA. Oncogene. Aug. 28, 2003;22(36):5712-5.
Towne et al., Systemic AAV6 delivery mediating RNA interference against SOD1: neuromuscular transduction does not alter disease progression in fALS mice. Mol Ther. Jun. 2008;16(6):1018-25. doi:10.1038/mt.2008.73. Epub Apr. 15, 2008.
Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015.
Vandenberghe et al., Heparin binding directs activation of T cells against adeno-associated virus serotype 2 capsid. Nat Med. Aug. 2006;12(8):967-71. Epub Jul. 16, 2006.
Vandenberghe et al., Tailoring the AAV vector capsid for gene therapy. Gene Ther. Mar. 2009;16(3):311-9. Epub Dec. 4, 2008.
Vandendriessche et al., Efficacy and safety of adeno-associated viral vectors based on serotype 8 and 9 vs. lentiviral vectors for hemophilia B gene therapy. J Thromb Haemost. Jan. 2007;5(1):16-24. Epub Sep. 26, 2006.
Wang et al., Rescue and replication of adeno-associated virus type 2 as well as vector DNA sequences from recombinant plasmids containing deletions in the viral inverted terminal repeats: selective encapsidation of viral genomes in progeny virions. J Virol. Mar. 1996;70(3):1668-77.
Wang et al., Somatically Repairing Compound Heterozygous Recessive Mutations by Chromosomal Cut-and-Paste for in Vivo Gene Therapy. May 2016. 24(1):S289. Abstract 733.
Wang et al., The potential of adeno-associated viral vectors for gene delivery to muscle tissue. Expert Opin Drug Deliv. Mar. 2014;11(3):345-64. doi: 10.1517/17425247.2014.871258. Epub Jan. 3, 2014.
Wang et al., Widespread spinal cord transduction by intrathecal injection of rAAV delivers efficacious RNAi therapy for amyotrophic lateral sclerosis. Hum Mol Genet. Feb. 1, 2014;23(3):668-81. doi: 10.1093/hmg/ddt454. Epub Sep. 18, 2013.
Weismann et al., Systemic AAV9 gene transfer in adult GM1 gangliosidosis mice reduces lysosomal storage in CNS and extends lifespan. Hum Mol Genet. Aug. 1. 2015;24(15):4353-64. doi: 10.1093/hmg/ddv168. Epub May 10, 2015.
Weismann, Approaches and Considerations Towards a Safe and Effective Adena-Associated Virus Mediated Therapeutic Intervention for GM 1-Gangliosidosis: A Dissertation. University Massachusetts Medical School. Aug. 5, 2014.
Wu et al., Alpha2,3 and alpha2,6 N-linked sialic acids facilitate efficient binding and transduction by adeno-associated virus types 1 and 6. J Virol. Sep. 2006;80(18):9093-103.
Xie et al., Isolation of transcriptionally active novel AAV capsid sequences from chimpanzee tissues for vector development. Meeting Abstract: 12th Annual Meeting of the American Society of Gene Therapy. May 1, 2009. Abstract 91.
Xie et al., 676. DNA Sequences Encoding shRNAs Can Replace Mutant ITR in scAAV Genome for Efficient Replication and Packaging and Transcribe shRNAs by pol III Promoter Activity of wt ITR for Efficient Gene Silencing Mol Therapy. May 2015;23(1):S269.
Xie et al., Characterization of positioning effect of pol III-shRNA transcription unit in scAAV vector genome on the packaging efficiency and functionality of shRNA silencing. Molecular Therapy. May 2010;18(1): S262. Abstract 671.
Xie et al., MicroRNA regulated tissue specific transduction by rAAV vector. Molecular Therapy. May 2009;17(1): S279. Abstract 732.
Xie et al., MicroRNA-regulated, systemically delivered rAAV9: a step closer to CNS-restricted transgene expression. Mol Ther. Mar. 2011;19(3):526-35. doi: 10.1038/mt.2010.279. Epub Dec. 21, 2010.
Xie et al., rAAV-mediated delivery of micro RNA scavengers leads to efficient and stable knock-down of cognate micro RNAs, upregulation of their natural target genes and phenotypic changes in mice. Molecular Therapy. May 2010;18(1): S140. Abstract 362.
Xie et al., Short DNA Hairpins Compromise Recombinant Adeno-Associated Virus Genome Homogeneity. Mol Ther. Jun. 7, 2017;25(6):1363-1374. doi: 10.1016/j.ymthe.2017.03.028. Epub Apr. 24, 2017.
Xu et al., Delivery of MDR1 small interfering RNA by self-complementary recombinant adeno-associated virus vector. Mol Ther. Apr. 2005;11(4):523-30.
Yan et al., Unique biologic properties of recombinant AAV1 transduction in polarized human airway epithelia. J Biol Chem. Oct. 6, 2006;281(40):29684-92. Epub Aug. 9, 2006.
Zhang et al., Characterization of 12 AAV vectors for intravascular delivery to target CNS and detarget non-CNS tissues by mirna regulation: implications in treatment of canavan disease. Molecular Therapy. May 2010;18(1): S174. Abstract 450.
Zhong et al., Chimpanzee-derived novel natural variants of aav9: vector development and interrogation of correlations between capsid structure and vector biology. Molecular Therapy. May 2010;18(1): S24. Abstract 58.
Zincarelli et al., Analysis of AAV serotypes 1-9 mediated gene expression and tropism in mice after systemic injection. Mol Ther. Jun. 2008;16(6):1073-80. doi: 10.1038/mt.2008.76. Epub Apr. 15, 2008.
Zolotukhin et al., Production and purification of serotype 1, 2, and 5 recombinant adeno-associated viral vectors. Methods. Oct. 2002;28(2): 158-67.

* cited by examiner

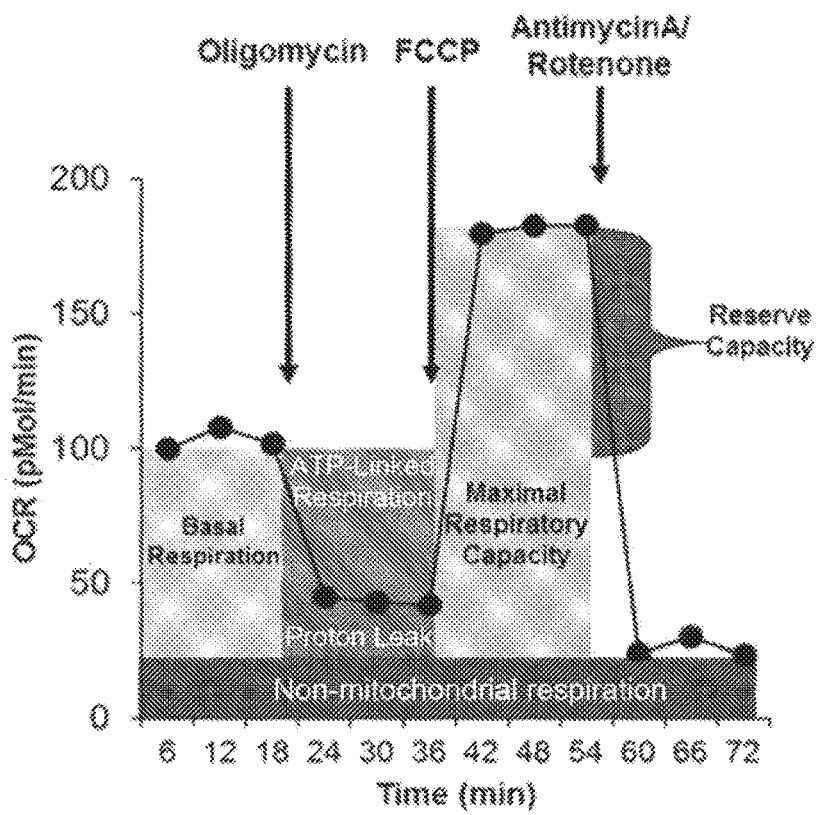
GLIOMA
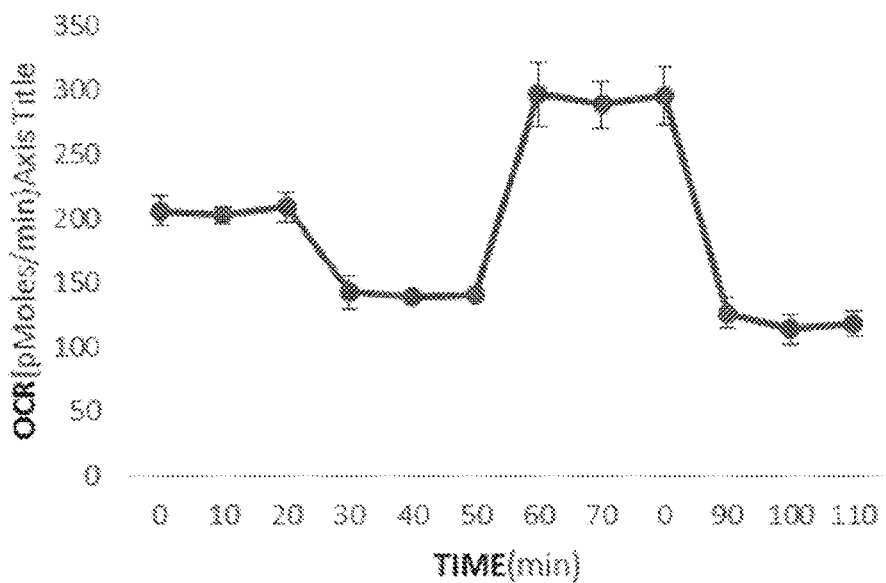
FIG. 1A

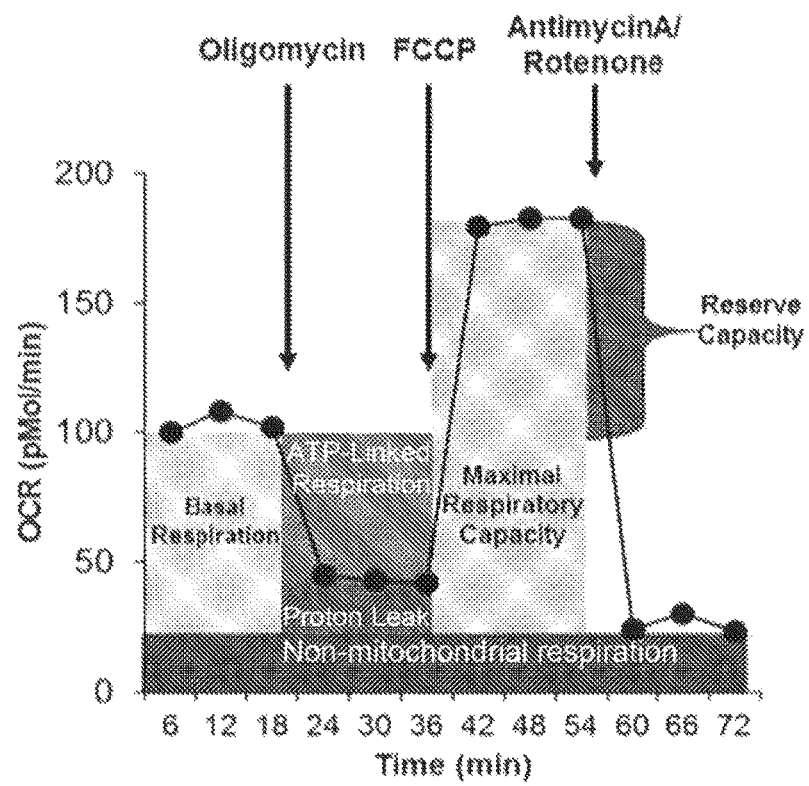
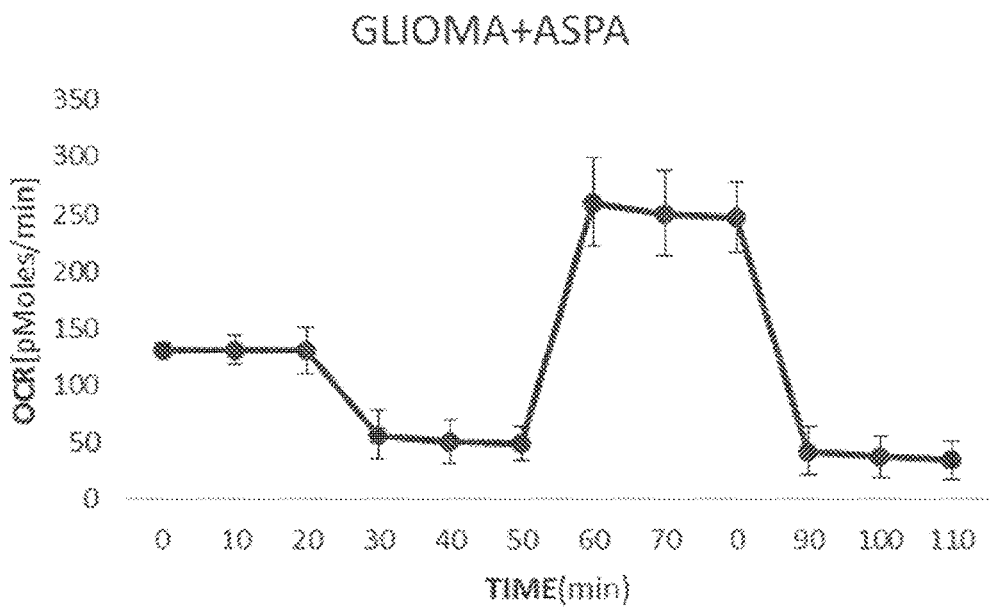
FIG. 1B

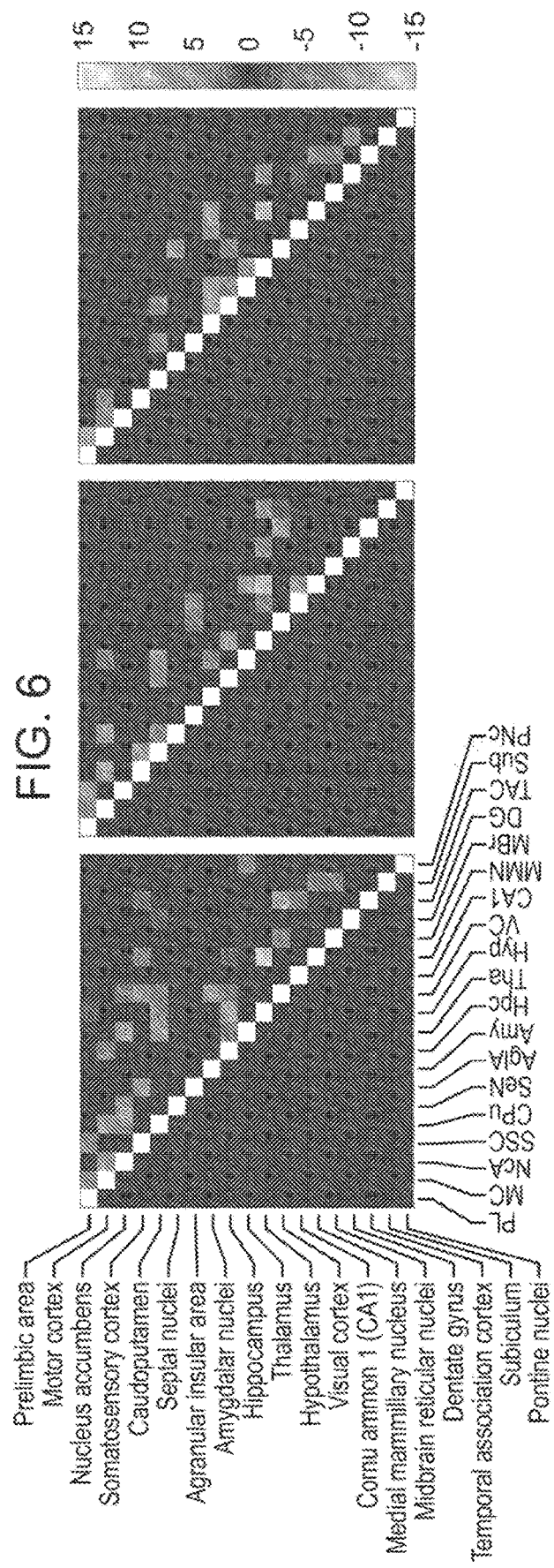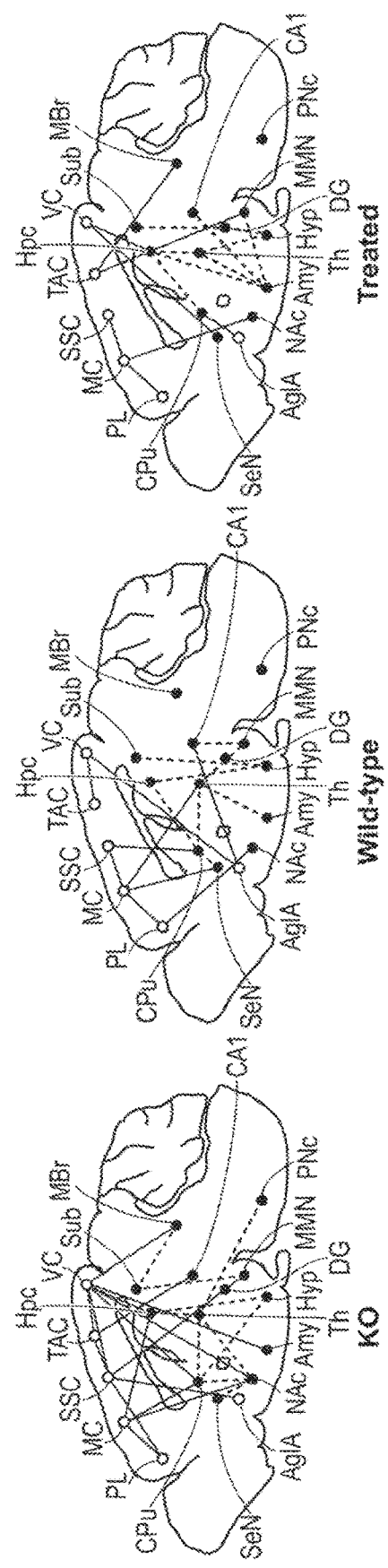
FIG. 6

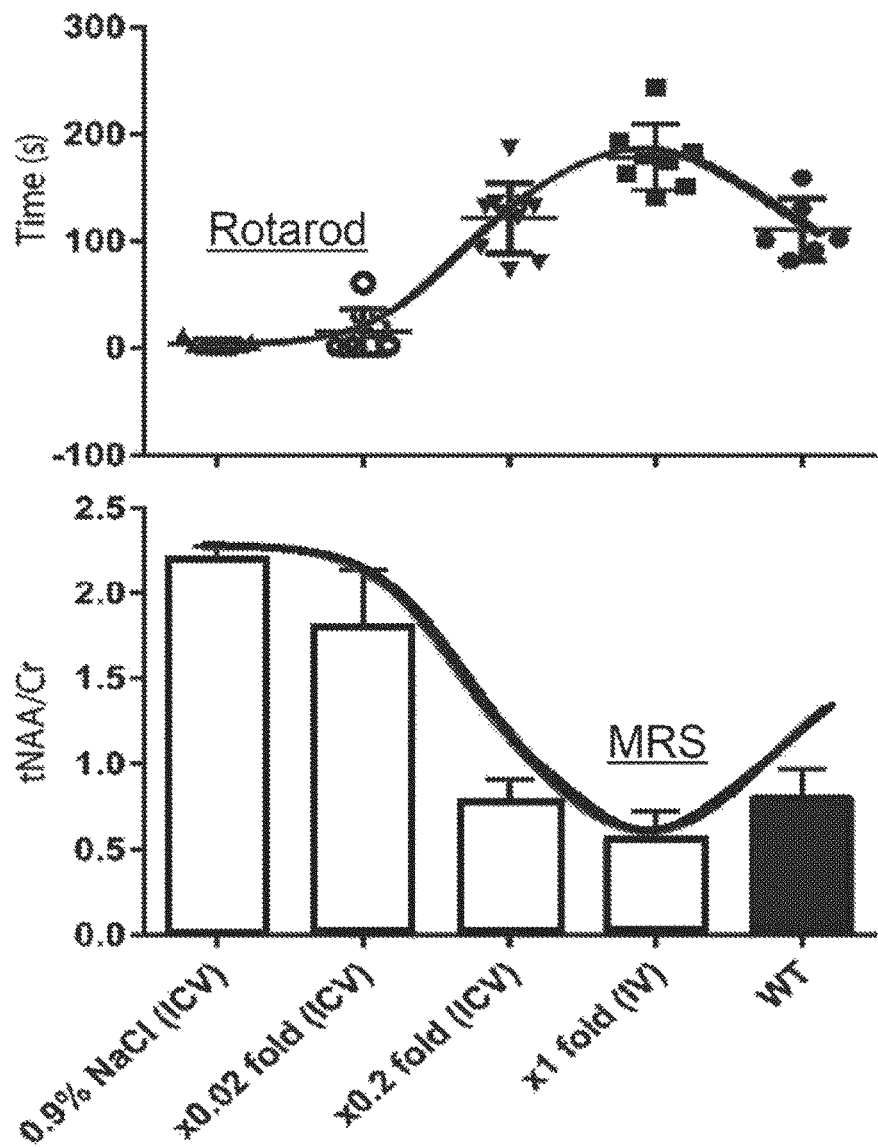
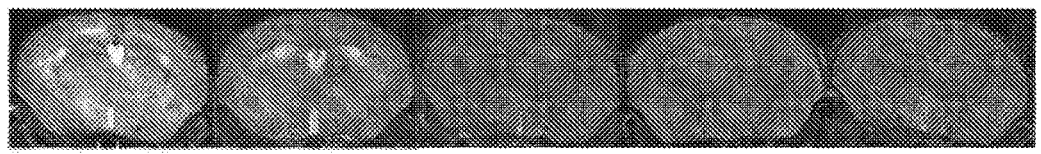
FIG. 11

* p<0.05;  p<0.01; * p<0.001; **** p<0.0001

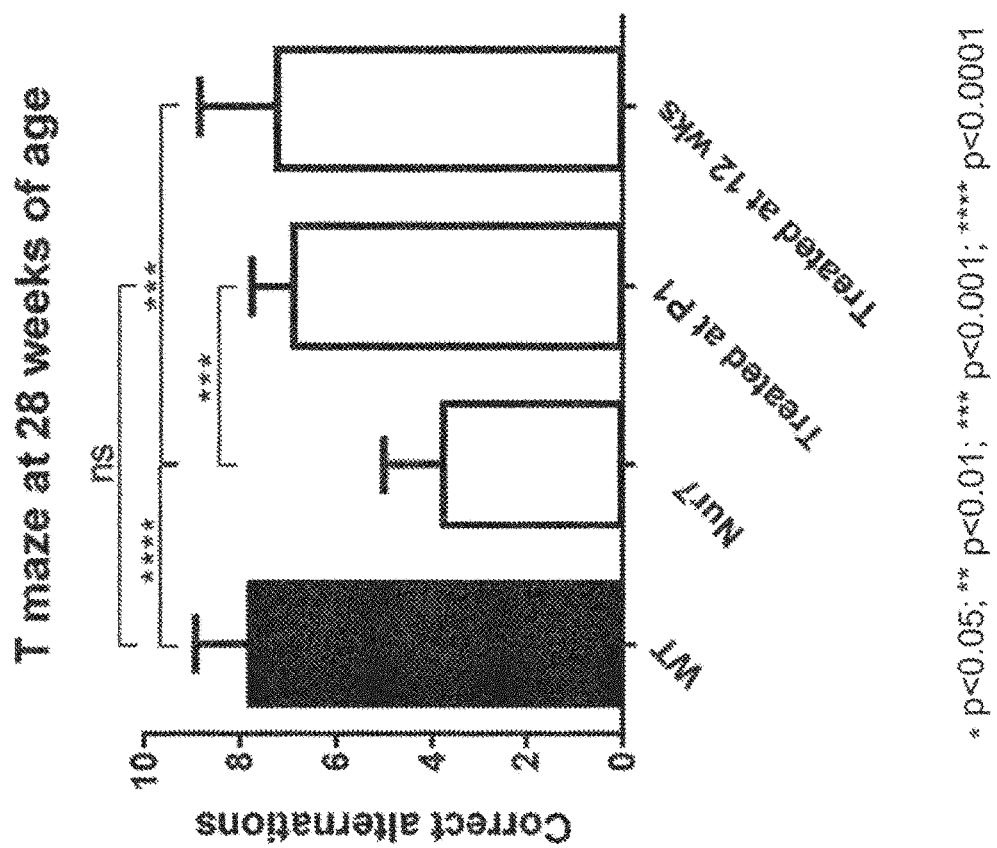
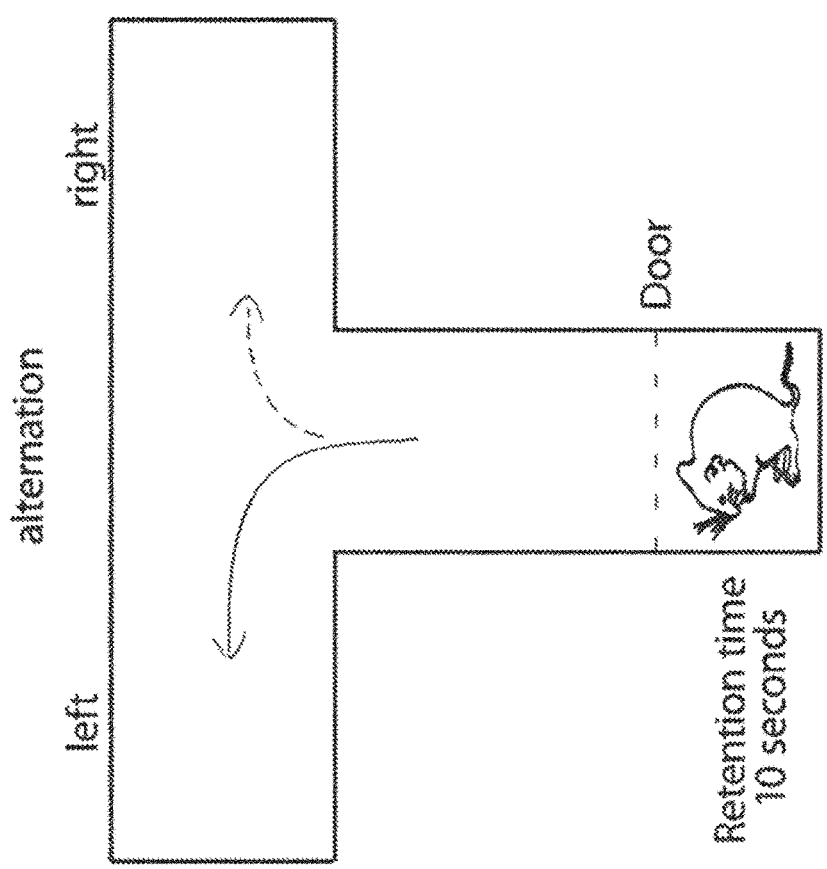
FIG. 13

| sphingomyelins | KO/WT | rAAV (Tx/Ctrl) |
|---|---|---|
| palmitoyl sphingomyelin (d18:1/16:0) | 0.59 | 1.22 |
| stearoyl sphingomyelin (d18:1/18:0) | 0.84 | 1.16 |
| sphingomyelin (d18:1/18:1, d18:2/18:0) | 0.97 | 1.05 |
| sphingomyelin (d18:1/14:0, d16:1/16:0)* | 0.5 | 1.01 |
| sphingomyelin (d18:1/24:1, d18:2/24:0)* | 0.56 | 1.95 |
| sphingomyelin (d18:2/16:0, d18:1/16:1)* | 0.47 | 0.82 |
| sphingomyelin (d18:1/20:1, d18:2/20:0)* | 0.82 | 0.87 |
| behenoyl sphingomyelin (d18:1/22:0)* | 0.56 | 1.56 |
| sphingomyelin (d18:1/22:1, d18:2/22:0, d | 0.59 | 1.62 |
| sphingomyelin (d18:1/20:0, d16:1/22:0)* | 0.9 | 1.09 |
| palmitoyl dihydrosphingomyelin (d18:0/16 | 0.37 | 2.09 |
| sphingomyelin (d18:1/15:0, d16:1/17:0)* | 0.26 | 0.95 |
| sphingomyelin (d18:1/21:0, d17:1/22:0, d | 0.6 | 1.19 |
| sphingomyelin (d18:2/23:0, d18:1/23:1, d | 0.6 | 1.79 |
| sphingomyelin (d18:2/24:1, d18:1/24:2)* | 0.76 | 1.38 |
| tricosanoyl sphingomyelin (d18:1/23:0)* | 0.83 | 0.87 |
| sphingomyelin (d18:1/17:0, d17:1/18:0,d | 0.72 | 1.28 |

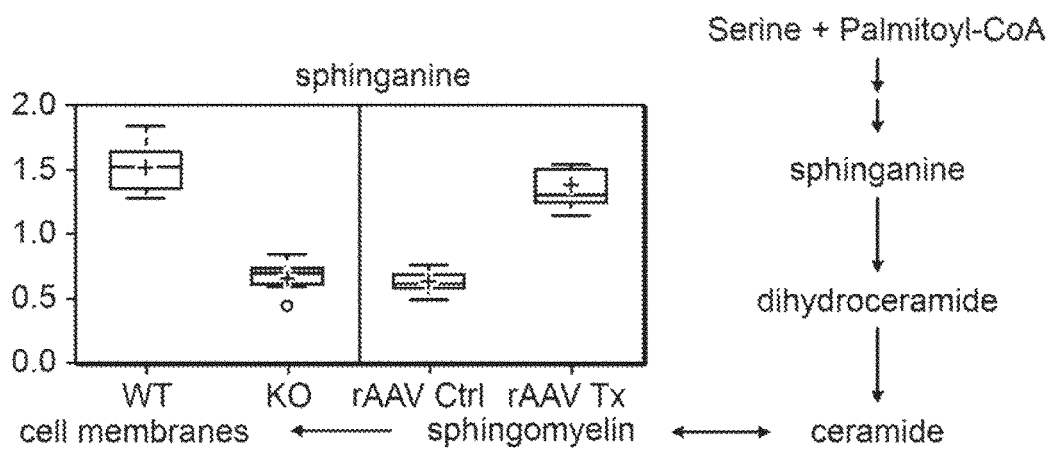

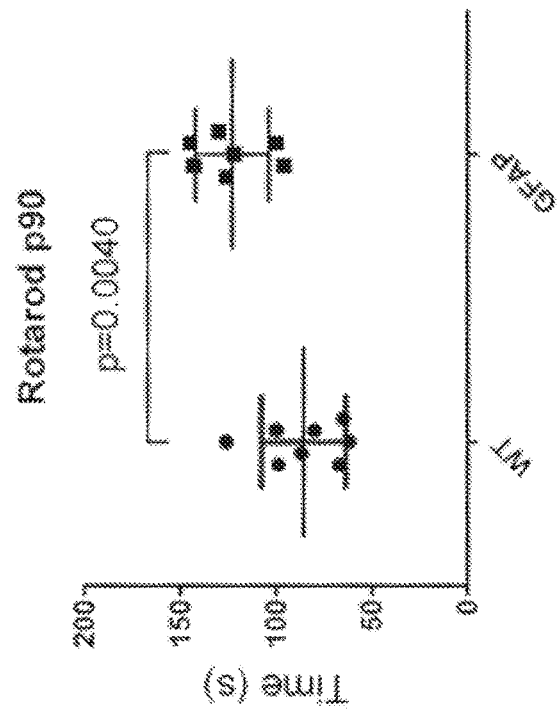
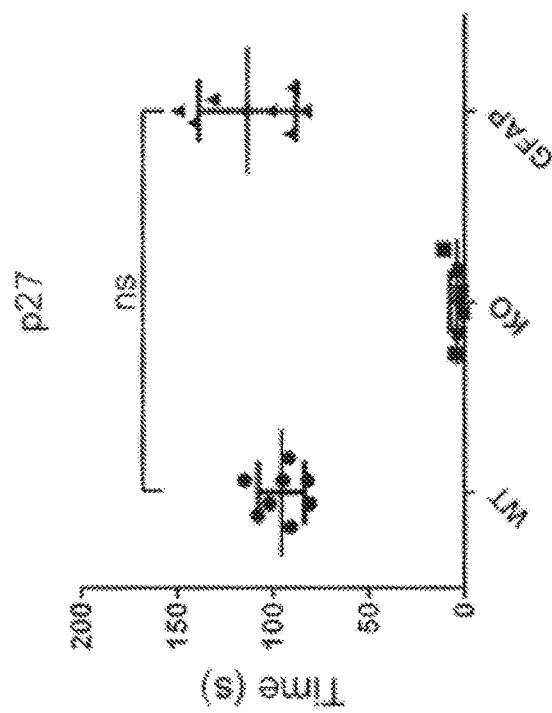
FIG. 26

METHODS AND COMPOSITIONS FOR TREATING METABOLIC IMBALANCE

RELATED APPLICATIONS

This Application is a national stage filing under 35 U.S.C. § 371 of International Patent Application Serial No. PCT/US2017/027759, filed Apr. 14, 2017, and claims the benefit of the filing date under 35 U.S.C. 119(e) of the U.S. provisional Application Ser. No. 62/323,587, filed Apr. 15, 2016, entitled "METHODS AND COMPOSITIONS FOR TREATING METABOLIC IMBALANCE", the entire contents of each of which are incorporated herein by reference.

REFERENCE TO A SEQUENCE LISTING SUBMITTED AS A TEST FILE VIA EFS-WEB

The instant application contains a Sequence Listing which has been submitted in ASCII format via EFS-Web and is hereby incorporated by reference in its entirety. Said ASCII copy, created on Oct. 15, 2018, is named U012070081US01-SEQ-KZM and is 8,568 bytes in size.

BACKGROUND

Diseases such as cancer, obesity, etc., are a huge financial burden for society with increasing incidence and prevalence in populations across the world. Metabolic imbalance is often an underlying cause of disease. For example, in subjects having diabetes, the metabolic pathway that removes glucose from the blood is impaired.

SUMMARY

The disclosure relates, in some aspects, to compositions and methods useful for the diagnosis and treatment of diseases and disorders associated with a metabolic imbalance in a subject. In some embodiments, a metabolic imbalance in a subject is characterized by an increase in glycolytic activity (e.g., a shift towards glycolysis) relative to a subject that does not have a metabolic imbalance, or by an increase in beta-oxidation (e.g., fatty acid metabolism) relative to a subject that does not have a metabolic imbalance.

In some aspects, the disclosure relates to the discovery that delivery of a transgene engineered to express aspartoacylase (ASPA) can, as a result of ASPA expression, produce a shift in energy metabolism away from glycolysis and toward beta-oxidation (e.g., fatty acid metabolism) in subjects having certain diseases (e.g., diseases associated with a metabolic imbalance characterized by increased glycolysis, such as cancer, etc.).

In some aspects, the disclosure relates to the recognition that delivery of a transgene engineered to N-acetylaspartate synthetase (NAT8L) can, as a result of NAT8L expression, shift energy metabolism away from beta-oxidation (e.g., fatty acid metabolism) and toward glycolysis in subjects having certain diseases (e.g., diseases associated with a metabolic imbalance characterized by increased beta oxidation, such as diabetes, etc.).

Accordingly in some aspects, the disclosure provides a method of increasing adenosine tri-phosphate (ATP) production in a subject, the method comprising administering to a subject a recombinant adeno-associated virus (rAAV) comprising a transgene encoding ASPA enzyme or NAT8L enzyme, wherein the subject does not have an ASPA deficiency or a neurodegenerative disease.

In some aspects, the disclosure provides a method for treating a disease associated with a metabolic imbalance in a subject in need thereof, the method comprising administering to the subject an N-acetylaspartate (NAA)-depleting agent, wherein it has been determined that the disease is associated with a metabolic imbalance comprising a shift from beta-oxidation to glycolysis in the subject.

In some aspects, the disclosure provides a method for treating a disease associated with a metabolic imbalance in a subject in need thereof, the method comprising administering to the subject an N-acetylaspartate (NAA)-depleting agent, wherein it has been determined that the disease is associated with a metabolic imbalance comprising a shift from glycolysis to beta-oxidation in the subject.

In some aspects, the disclosure provides a method for treating a disease associated with a metabolic imbalance in a subject in need thereof, the method comprising administering to the subject an N-acetylaspartate (NAA)-increasing agent, wherein it has been determined that the disease is associated with a metabolic imbalance comprising a shift from beta-oxidation to glycolysis in the subject.

In some aspects, the disclosure provides a method for treating a disease associated with a metabolic imbalance in a subject in need thereof, the method comprising administering to the subject an N-acetylaspartate (NAA)-increasing agent, wherein it has been determined that the disease is associated with a metabolic imbalance comprising a shift from glycolysis to beta-oxidation in the subject.

In some aspects, the disclosure provides a method for treating cancer in a subject in need thereof, the method comprising: measuring a metabolic profile of a biological sample obtained from a subject; identifying a metabolic imbalance associated with cancer based upon the metabolic profile; and, administering to the subject an N-acetylaspartate (NAA)-depleting agent, wherein the metabolic imbalance comprises a shift from beta-oxidation to glycolysis. In some embodiments a subject is a human.

In some embodiments of methods described by the disclosure, a disease associated with a metabolic imbalance is obesity, diabetes mellitus, or cancer. In some embodiments, a cancer is ovarian cancer, breast cancer, lung squamous cell carcinoma, kidney renal cell carcinoma, colorectal cancer, prostate cancer, uterine endometroid cancer, or melanoma.

In some embodiments, methods described by the disclosure further comprise detecting a metabolic imbalance by evaluating levels of one or more glycolysis and/or beta-oxidation factors (e.g., by evaluating levels of an informative molecule or set of molecules of a metabolic pathway, for example as disclosed in International Application number PCT/US2016/058197, the entire contents of which are incorporated herein by reference). In some embodiments, levels of one or more glycolysis and/or beta-oxidation factors are determined using a biological sample obtained from a subject. In some embodiments, a biological sample is a tissue sample. In some embodiments, a tissue sample comprises a tumor or tumor cells.

In some embodiments, measuring the metabolic profile comprises assaying the biological sample using liquid chromatography (LC), mass spectrometry (MS), or liquid chromatography/mass spectrometry (LC/MS). In some embodiments, measuring the metabolic profile comprises assaying the biological sample using Ultrahigh Performance Liquid Chromatography-Tandem Mass Spectroscopy (UPLC-MS/MS).

In some embodiments, a metabolic profile comprises a level of a first biomarker selected from the group consisting of glucose, glucose-6-phosphate, 3-phosphoglycerate, pyruvate, lactate, and phosphoenolpyruvate. In some embodiments, a metabolic profile comprises a level of a second biomarker selected from the group consisting of carnitine, malonylcarnitine, myristoylcarnitine, palmitoylcarnitine, malonylcarnitine, and beta-hydroxybutyrate. In some embodiments, a metabolic profile further comprises a level of one or more additional biomarkers indicating an increase in glycolysis in the subject, or indicating an increase in beta-oxidation of the subject.

In some embodiments, an NAA-depleting agent is ASPA. In some embodiments, an NAA-depleting agent is selected from the group consisting of a small molecule, a protein, and a nucleic acid. In some embodiments, an NAA-depleting agent is administered using a recombinant adeno-associated virus (rAAV).

In some embodiments, an NAA-increasing agent is N-acetylaspartate synthetase (NAT8L). In some embodiments, an NAA-increasing agent is selected from the group consisting of a small molecule, a protein, and a nucleic acid. In some embodiments, an NAA-increasing agent is administered using a rAAV.

In some embodiments, an rAAV comprises: a capsid protein; and, a nucleic acid comprising a promoter operably linked to a transgene, wherein the transgene encodes aspartoacylase (ASPA) or N-acetylaspartate synthetase (NAT8L).

In some embodiments, a capsid protein has a serotype selected from the group consisting of AAV9 or variants thereof.

In some embodiments, an rAAV is administered via injection. In some embodiments, the injection is selected from the group consisting of intravenous injection, intravascular injection and intraventricular injection. In some embodiments, the injection is intratumoral injection.

In some embodiments of methods described by the disclosure, administration of an rAAV results in expression of a transgene in a target tissue or cell. In some embodiments, a target tissue or cell is a tumor or a tumor cell.

In some embodiments, an rAAV comprises a tissue-specific promoter, such as a tumor-specific promoter.

In some embodiments, methods described by the disclosure further comprise administering a small molecule metabolic modulator to a subject.

In some embodiments, methods described by the disclosure further comprise prescribing to a subject a dietary intervention, wherein the dietary intervention promotes glycolysis and/or reduces beta-oxidation in the subject.

In some embodiments, methods described by the disclosure further comprise comprising prescribing to the subject a dietary intervention, wherein the dietary intervention promotes beta-oxidation and/or reduces glycolysis in the subject.

In some embodiments, methods described by the disclosure further comprise administering an immune-suppressing agent to a subject. In some embodiments, the immune-suppressing agent is administered to the subject prior to the administration of the rAAV.

BRIEF DESCRIPTION OF DRAWINGS

FIG. 1A shows the metabolic profile of a glioma cell line (U87). FIG. 1B shows the metabolic profile of a glioma cell line (U87) after delivery of rAAV-ASPA.

FIG. 3A shows a reduction in glycolytic reserve of glioma cells administered rAAV-ASPA compared to untreated control cells. FIG. 3B shows an increase in fatty acid (FA) dependency in glioma cells administered rAAV-ASPA compared to untreated control cells.

FIG. 6 shows data illustrating that Canavan disease (CD) causes increased oxygen consumption for cortical-subcortical connectivity.

FIG. 7A shows a Principle Component Analysis (PCA) of WT (untreated/treated) and KO (untreated/treated) mice. FIG. 7B shows Hierarchical Clustering Analysis of WT (untreated/treated) and KO (untreated/treated) mice. Both FIGS. 7A and 7B show clustering of WT and KO (treated) mice, indicating that rAAV-ASPA treatment rescues metabolic phenotype in CD mice.

FIG. 11 shows data illustrating that tissue-specific (intraventricular, ICV) and systemic (intravenous, IV) administration of rAAV-ASPA result in comparable therapeutic outcomes in P1 treated mice having a disease associated with a metabolic imbalance. Mice were assessed at P26.

FIG. 13 shows data illustrating that cognitive function (e.g., working/spatial memory) is restored in Nur7 mice intravenously administered rAAV-ASPA at P1 and at 3 months.

FIG. 16 shows data illustrating that rAAV-ASPA treatment restores the myelin-lipid profile in mice having a disease associated with a metabolic imbalance. Compared to WT mice, KO mice have significantly reduced levels of sphingolipids and other myelin components. CD mice treated with rAAV-ASPA show a significant increase in myelin components, such as sphinganine.

FIG. 26 shows astrocyte-restricted expression of hASPA results in normalization of motor function in mice having a disease associated with a metabolic imbalance (e.g., CD KO mice). CD KO mice were administered astrocyte-restricted rAAV-hASPA and motor function was measured at p27 and p90. Data show that astrocyte-restricted expression of hASPA resulted in restoration of motor function in treated CD KO mice compared to wild-type (WT) mice. At p90, treated CD KO mice outperformed WT mice in a rotarod test.

DETAILED DESCRIPTION

Figure 1A:
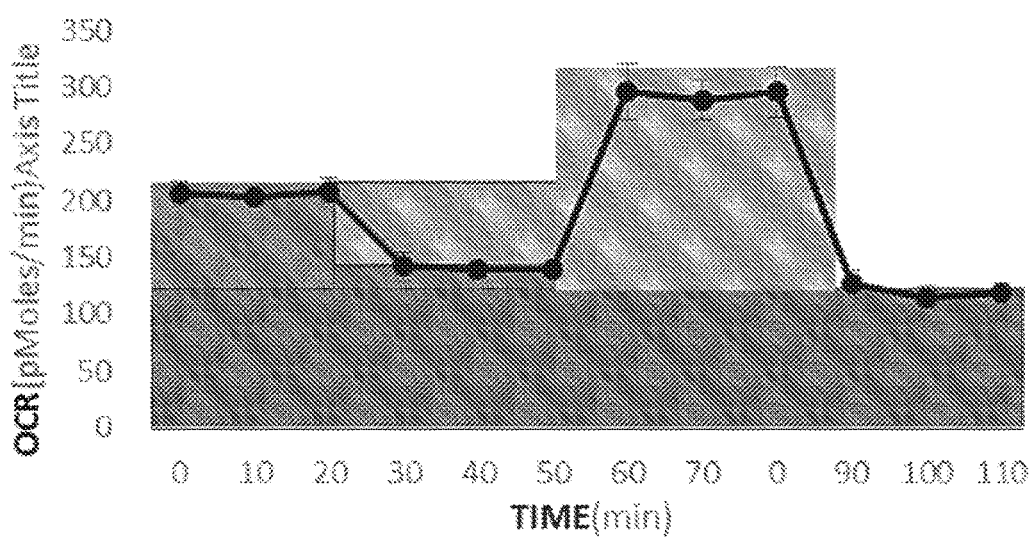
FIGS. 1A-1B show representative data for metabolic profiling of glioma cells, as measured by oxygen consumption rate (OCR) and extracellular acidification rate (ECAR) (e.g., using a Seahorse XF instrument).

Aspects of the disclosure relate to methods for treating a disease associated with a metabolic imbalance (e.g., cancer, obesity, diabetes, etc.) in a subject in need thereof. Methods provided herein, in some embodiments, involve modulating N-acetylaspartate (NAA) levels in a subject. NAA has been identified as the second most abundant molecule in the central nervous system (CNS). In some embodiments, NAA synthesis takes place in neurons. In some embodiments, NAA is not synthesized in cells or organs outside the CNS. NAA is metabolized by the enzyme aspartoacylase (ASPA) into acetate and L-aspartate. In some embodiments, ASPA is expressed in the CNS (e.g., in oligodendrocytes). In some embodiments, ASPA is expressed in peripheral organs, such as kidney, small intestines and others. In some embodiments, diseases such as cancer, obesity, diabetes, etc. demonstrate disturbance of cellular metabolism, for example a shift away from beta-oxidation towards glycolysis, or a shift away from glycolysis and towards beta-oxidation. Accordingly, in some embodiments, detection of a metabolic imbalance (e.g., a disturbance of metabolic activity or pathways in a cell or a subject) may be used as a disease marker for a wide range of diseases or disorders, e.g., cancer, obesity, diabetes, and neurodegenerative diseases and disorders, such as Canavan Disease, Alzheimer disease, traumatic brain injury, and psychiatric disorders.

In some embodiments, methods for treating diseases associated with a metabolic imbalance in a subject in need thereof are provided that involve administering to the subject an N-acetylaspartate (NAA)-depleting agent. As used herein, term "NAA-depleting agent" refers to an agent (e.g., nucleic acid, peptide, protein, small molecule) that depletes NAA levels directly or indirectly. In some embodiments, it has been determined that the disease is associated with a metabolic imbalance comprising a shift from glycolysis to beta-oxidation in the subject. In some embodiments, it has been determined that the disease is associated with a metabolic imbalance comprising a shift from beta-oxidation to glycolysis in the subject.

Other aspects of the disclosure relate to methods for treating disease in a subject in need thereof in which the methods involve administering to the subject an N-acetylaspartate (NAA)-increasing agent. As used herein, term "NAA-increasing agent" refers to an agent (e.g., nucleic acid, peptide, protein, small molecule) that increases NAA levels directly or indirectly. In some embodiments, it has been determined that a certain disease is associated with a metabolic imbalance comprising an NAA deficiency.

In some embodiments, an agent described by the disclosure (e.g., an NAA-depleting agent or an NAA-increasing agent) is a small molecule. Examples of small molecule NAA-depleting agents include rotenone, myxothiazol, cyanide and oligomycin. In some embodiments, an NAA-depleting agent or an NAA-increasing agent is a nucleic acid. In some embodiments, the nucleic acid is a dsRNA, siRNA, miRNA, artificial miRNA (ami-RNA), antisense oligonucleotide (ASO), aptamer (e.g., RNA aptamer, DNA aptamer, etc.), or closed-ended linear DNA molecule (e.g., CELID as described in International Publication No. WO2012/123430). In some embodiments, an NAA-depleting agent or an NAA-increasing agent is a peptide or protein. Examples of peptides and/or proteins include polypeptides, antibodies, and protein complexes (e.g., gene editing complexes, such as CRISPR/Cas9, TALENs, zinc-finger nucleases (ZFNs), etc.).

As used herein, "metabolic imbalance" refers to a dysregulated or abnormal metabolic state in a subject. For example, in some embodiments, CNS cells of a healthy subject display a preference for glycolysis as a major mode of energy (e.g., ATP production); in subjects having certain diseases (e.g., diseases associated with leukodystrophy, e.g., Canavan disease), CNS cells display a preference for fatty acid metabolism. In some embodiments, such a shift away from glycolysis and towards beta-oxidation can be referred to as a "metabolic imbalance". In another example, in some embodiments, cells of a subject having a certain disease (e.g., cancer) display a preference for glycolysis that is significantly higher than cells of a subject not having the disease (e.g., cancer). In some embodiments, such an increased preference for glycolysis (and away from beta-oxidation) can be referred to as a metabolic imbalance. In some embodiments, cells of a subject having a certain disease (e.g., diabetes) display a preference for beta-oxidation that is significantly higher than cells of a subject not having the disease (e.g., diabetes). In some embodiments, such an increased preference for beta-oxidation (and away from glycolysis) can be referred to as a metabolic imbalance.

In some embodiments, methods disclosed herein involve comparing biomarkers (e.g., beta-oxidation, glycolysis) with an appropriate control. An "appropriate control" refers a level of a particular biomarker (e.g., beta-oxidation, glycolysis) that is indicative of a known metabolic status. Such levels can be determined experimentally or can be pre-existing reference levels. In some embodiments, an appropriate control may be a biomarker level indicative of the presence of a metabolic imbalance. For example, an appropriate control may be level of a factor (e.g., beta-oxidation, glycolysis) in a control subject. In some embodiments, a control subject does not have a metabolic imbalance. However, in some embodiments, a control subject does have a metabolic imbalance.

Treatment of Non-CNS Diseases

In some aspects, the disclosure relates to methods for treating diseases associated with metabolic imbalance (e.g., non-CNS diseases, such as diabetes, obesity, cancer, etc.). In some embodiments, the disclosure provides a method of treating a disease associated with a metabolic imbalance, the method comprising administering to a subject in need thereof an rAAV comprising an N-acetylaspartate (NAA)-increasing agent. In some embodiments, the disclosure provides a method of treating a disease associated with a metabolic imbalance, the method comprising administering to a subject in need thereof an rAAV comprising an N-acetylaspartate (NAA)-decreasing agent. Thus, in some embodiments, the methods involve administering to a subject a recombinant adeno-associated virus (rAAV) comprising a transgene encoding ASPA enzyme, or NAT8L enzyme.

Examples of diseases associated with a metabolic imbalance include but are not limited to obesity, diabetes mellitus (e.g., type I diabetes, type II diabetes, gestational diabetes, etc.), and cancer. Examples of cancer associated with metabolic imbalance include but are not limited to ovarian cancer, breast cancer, lung squamous cell carcinoma, kidney renal cell carcinoma, colorectal cancer, prostate cancer, uterine endometroid cancer, and melanoma.

Further non-limiting examples of cancer include, leukemia, such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma, such as Hodgkin lymphoma (HL) (e.g., B-cell HL, T-cell HL) and non-Hodgkin lymphoma (NHL) (e.g., B-cell NHL, such as diffuse large cell lymphoma (DLCL) (e.g., diffuse large B-cell lymphoma (DLBCL, e.g., activated B-cell (ABC) DLBCL (ABC-DLBCL))), follicular lymphoma, chronic lymphocytic leukemia/small lymphocytic lymphoma (CLL/SLL), mantle cell lymphoma (MCL), marginal zone B-cell lymphoma (e.g., mucosa-associated lymphoid tissue (MALT) lymphoma, nodal marginal zone B-cell lymphoma, splenic marginal zone B-cell lymphoma), primary mediastinal B-cell lymphoma, Burkitt lymphoma, Waldenström's macroglobulinemia (WM, lymphoplasmacytic lymphoma), hairy cell leukemia (HCL), immunoblastic large cell lymphoma, precursor B-lymphoblastic lymphoma, central nervous system (CNS) lymphoma (e.g., primary CNS lymphoma and secondary CNS lymphoma); and T-cell NHL, such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); lymphoma of an immune privileged site (e.g., cerebral lymphoma, ocular lymphoma, lymphoma of the placenta, lymphoma of the fetus, testicular lymphoma); a mixture of one or more leukemia/lymphoma as described above; myelodysplasia; and multiple myeloma (MM). Additional exemplary cancers include, but are not limited to, lung cancer (e.g., bronchogenic carcinoma, small cell lung cancer (SCLC), non-small cell lung cancer (NSCLC), adenocarcinoma of the lung); kidney cancer (e.g., nephroblastoma, a.k.a. Wilms' tumor, renal cell carcinoma); acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma; familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; liver cancer (e.g., hepatocellular cancer (HCC), malignant hepatoma); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

Recombinant Adeno-Associated Viruses (rAAVs)

In some aspects, the disclosure provides isolated AAVs that are useful for delivering transgenes that encode NAA-modulating agents (e.g., an NAA-depleting agent, an NAA-increasing agent). As used herein with respect to AAVs, the term "isolated" refers to an AAV that has been artificially produced or obtained. Isolated AAVs may be produced using recombinant methods. Such AAVs are referred to herein as "recombinant AAVs". Recombinant AAVs (rAAVs) preferably have tissue-specific targeting capabilities, such that a nuclease and/or transgene of the rAAV will be delivered specifically to one or more predetermined tissue(s). The AAV capsid is an important element in determining these tissue-specific targeting capabilities. Thus, an rAAV having a capsid appropriate for the tissue being targeted can be selected.

In some aspects, the disclosure provides an rAAV having a capsid appropriate for targeting central nervous system (CNS) tissue or other tissue (e.g., a peripheral tissue). In some embodiments, the capsid has a serotype selected from the group consisting of AAV1, AAV2, AAV5, AAV6, AV6.2, AAV7, AAV8, AAV9 and AAVrh.10. In some embodiments, an rAAV described herein may comprise variants of AAV1, AAV2, AAV5, AAV6, AV6.2, AAV7, AAV8, AAV9, and AAVrh.10 serotype capsid proteins. In some embodiments, the capsid protein comprises an amino acid sequence that is at least 70%, at least 80%, at least 90%, at least 95%, or at least 99% identical to any one of the recited capsids.

Appropriate methods may be used for obtaining recombinant AAVs having a desired capsid protein. (See, for example, US 2003/0138772), the contents of which are incorporated herein by reference in their entirety). Typically the methods involve culturing a host cell which contains a nucleic acid sequence encoding an AAV capsid protein; a functional rep gene; a recombinant AAV vector composed of, AAV inverted terminal repeats (ITRs) and a transgene; and sufficient helper functions to permit packaging of the recombinant AAV vector into the AAV capsid proteins. In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, the functions of the capsid proteins are to protect the viral genome, deliver the genome and interact with the host. In some aspects, capsid proteins deliver the viral genome to a host in a tissue specific manner.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component (s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

In some embodiments, the instant disclosure relates to a host cell containing a nucleic acid that comprises a coding sequence encoding a gene associated with a neurodegenerative disease (e.g., a leukodystrophy). In some embodiments, the instant disclosure relates to a composition comprising the host cell described above. In some embodiments, the composition comprising the host cell above further comprises a cryopreservative.

The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present disclosure. See, e.g., K. Fisher et al, J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an recombinant AAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or functional RNA (e.g., shRNA, miRNA) from a transcribed gene.

The foregoing methods for packaging recombinant vectors in desired AAV capsids to produce the rAAVs of the disclosure are not meant to be limiting and other suitable methods will be apparent to the skilled artisan.

Isolated Nucleic Acids

A "nucleic acid" sequence refers to a DNA or RNA sequence. In some embodiments, proteins and nucleic acids of the disclosure are isolated. As used herein, the term "isolated" means artificially produced. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. As used herein with respect to proteins or peptides, the term "isolated" refers to a protein or peptide that has been isolated from its natural environment or artificially produced (e.g., by chemical synthesis, by recombinant DNA technology, etc.).

In some embodiments, conservative amino acid substitutions may be made to provide functionally equivalent variants, or homologs of the capsid proteins. In some aspects the disclosure embraces sequence alterations that result in conservative amino acid substitutions. As used herein, a conservative amino acid substitution refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g., Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made among amino acids within the following groups: (a) M, I, L, V; (b) F, Y, W; (c) K, R, H; (d) A, G; (e) S, T; (f) Q, N; and (g) E, D. Therefore, one can make conservative amino acid substitutions to the amino acid sequence of the proteins and polypeptides disclosed herein.

Recombinant AAV Vectors (rAAV Vectors)

"Recombinant AAV (rAAV) vectors" of the disclosure are typically composed of, at a minimum, a transgene and its regulatory sequences, and 5' and 3' AAV inverted terminal repeats (ITRs). It is this recombinant AAV vector which is packaged into a capsid protein and delivered to a selected target cell. In some embodiments, the transgene is a nucleic acid sequence, heterologous to the vector sequences, which encodes a polypeptide, protein, functional RNA molecule (e.g., shRNA, miRNA) or other gene product, of interest. The nucleic acid coding sequence is operatively linked to regulatory components in a manner which permits transgene transcription, translation, and/or expression in a cell of a target tissue.

In some embodiments, the instant disclosure relates to a recombinant AAV (rAAV) vector comprising a nucleic acid sequence including a promoter operably linked to a transgene, wherein the transgene is a gene associated with a neurodegenerative disease (e.g., leukodystrophy). In some embodiments, a rAAV vector further comprises nucleic acid sequences encoding one or more AAV inverted terminal repeat sequences (ITRs), for example AAV2 ITRs. In some embodiments, a rAAV vector further comprises nucleic acid sequences encoding one or more AAV ITRs selected from the group consisting of AAV2, AAV3, AAV4, AAV5, and AAV6.

The AAV sequences of the vector typically comprise the cis-acting 5' and 3' inverted terminal repeat sequences (See, e.g., B. J. Carter, in "Handbook of Parvoviruses", ed., P. Tijsser, CRC Press, pp. 155 168 (1990)). The ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). An example of such a molecule employed in the present disclosure is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types (e.g., AAV2, AAV3, AAV4, AAV5, or AAV6 ITR sequences).

In some embodiments, the rAAVs of the present disclosure are pseudotyped rAAVs. Pseudotyping is the process of producing viruses or viral vectors in combination with foreign viral envelope proteins. The result is a pseudotyped virus particle. With this method, the foreign viral envelope proteins can be used to alter host tropism or an increased/decreased stability of the virus particles. In some aspects, a pseudotyped rAAV comprises nucleic acids from two or more different AAVs, wherein the nucleic acid from one AAV encodes a capsid protein and the nucleic acid of at least one other AAV encodes other viral proteins and/or the viral genome. In some embodiments, a pseudotyped rAAV refers to an AAV comprising an inverted terminal repeats (ITRs) of one AAV serotype and an capsid protein of a different AAV serotype. For example, a pseudotyped AAV vector containing the ITRs of serotype X encapsidated with the proteins of Y will be designated as AAVX/Y (e.g., AAV2/1 has the ITRs of AAV2 and the capsid of AAV1). In some embodiments, pseudotyped rAAVs may be useful for combining the tissue-specific targeting capabilities of a capsid protein from one AAV serotype with the viral DNA from another AAV serotype, thereby allowing targeted delivery of a transgene to a target tissue.

In addition to the major elements identified above for the recombinant AAV vector, the vector also includes control elements necessary which are operably linked to the transgene in a manner which permits its transcription, translation and/or expression in a cell transfected with the plasmid vector or infected with the virus produced by the disclosure. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible, ubiquitous, and/or tissue-specific, are known in the art and may be utilized.

As used herein, a nucleic acid sequence (e.g., coding sequence) and regulatory sequences are said to be "operably" linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., shRNA).

For nucleic acids encoding proteins, a polyadenylation sequence generally is inserted following the transgene sequences and before the 3' AAV ITR sequence. A rAAV construct useful in the present disclosure may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and/or other vector elements may be performed, as appropriate, and many such sequences are available [see, e.g., Sambrook et al, and references cited therein at, for example, pages 3.18 3.26 and 16.17 16.27 and Ausubel et al., Current Protocols in Molecular Biology, John Wiley & Sons, New York, 1989]. In some embodiments, a Foot and Mouth Disease Virus 2A sequence is included in polyprotein; this is a small peptide (approximately 18 amino acids in length) that has been shown to mediate the cleavage of polyproteins (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459). The cleavage activity of the 2A sequence has previously been demonstrated in artificial systems including plasmids and gene therapy vectors (AAV and retroviruses) (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459; de Felipe, P et al., Gene Therapy, 1999; 6: 198-208; de Felipe, Petal., Human Gene Therapy, 2000; 11: 1921-1931.; and Klump, H et al., Gene Therapy, 2001; 8: 811-817).

The precise nature of the regulatory sequences needed for gene expression in host cells may vary between species, tissues or cell types, but shall in general include, as necessary, 5' non-transcribed and 5' non-translated sequences involved with the initiation of transcription and translation respectively, such as a TATA box, capping sequence, CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors of the disclosure may optionally include 5' leader or signal sequences. The choice and design of an appropriate vector is within the ability and discretion of one of ordinary skill in the art.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter [Invitrogen]. In some embodiments, a promoter is an enhanced chicken β-actin promoter. In some embodiments, a promoter is an astrocyte specific promoter. In some embodiments, a promoter is an oligodendrocyte specific promoter. In some embodiments, a promoter is an CNS-specific promoter.

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al, Proc. Natl. Acad. Sci. USA, 93:3346-3351 (1996)), the tetracycline-repressible system (Gossen et al, Proc. Natl. Acad. Sci. USA, 89:5547-5551 (1992)), the tetracycline-inducible system (Gossen et al, Science, 268:1766-1769 (1995), see also Harvey et al, Curr. Opin. Chem. Biol., 2:512-518 (1998)), the RU486-inducible system (Wang et al, Nat. Biotech., 15:239-243 (1997) and Wang et al, Gene Ther., 4:432-441 (1997)) and the rapamycin-inducible system (Magari et al, J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (a-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter, Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et al., J. Bone Miner. Res., 11:654-64 (1996)), CD2 promoter (Hansal et al., J. Immunol., 161:1063-8 (1998);

immunoglobulin heavy chain promoter; T cell receptor α-chain promoter, neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)), among others which will be apparent to the skilled artisan. In some embodiments, the promoter is an oligodendrocyte-specific promoter, for example the myelin basic protein (MBP) promoter (Chen et al., J. Neurosci, Res., 55(4); 504-13 (1999)).

In some embodiments, a tissue-specific promoter is a tumor-specific promoter. Examples of tumor-specific promoters include but are not limited to AFP promoter (hepatocellular carcinoma), CCKAR promoter (pancreatic cancer), CEA promoter (epithelial cancers), c-erbB2 promoter (breast cancer, pancreatic cancer), COX-2 promoter, CXCR4 promoter, E2F-1 promoter, HE4 promoter, LP promoter, MUC1 promoter, PSA promoter (prostate cancer), surviving promoter, TRP1 promoter (melanoma), Tyr promoter (melanoma), etc.

Aspects of the disclosure relate to the discovery that astrocyte-specific (e.g., astrocyte-restricted) expression of hASPA results has a positive therapeutic effect (e.g., survival, normalized growth, restoration of normal motor function and cognitive function) in mouse models of Canavan Disease. Therefore, in some embodiments, the transgene of an rAAV described by the disclosure is operably-linked to an astrocyte-specific promoter. Examples of astrocyte-specific promoters include but are not limited to glial fibrillary acidic protein (GFAP) (Brenner et al., J. Neurosci, 14(3, Pt 1); 1030-7 (1994)), aldehyde dehydrogenase 1 family, member L1 (ALDH1L1) promoter (Cahoy et al., J. Neurosci. 28, 264-278 (2008)), and glutamate transporter promoter EAAT1 (Colin et al., Glia 57, 667-679 (2009)). In some embodiments, the astrocyte-specific promoter is the glial fibrillary acidic protein (GFAP) promoter.

In some embodiments, one or more bindings sites for one or more of miRNAs are incorporated in a transgene of a rAAV vector, to inhibit the expression of the transgene in one or more tissues of an subject harboring the transgene. The skilled artisan will appreciate that binding sites may be selected to control the expression of a transgene in a tissue specific manner. For example, binding sites for the liver-specific miR-122 may be incorporated into a transgene to inhibit expression of that transgene in the liver. The target sites in the mRNA may be in the 5' UTR, the 3' UTR or in the coding region. Typically, the target site is in the 3' UTR of the mRNA. Furthermore, the transgene may be designed such that multiple miRNAs regulate the mRNA by recognizing the same or multiple sites. The presence of multiple miRNA binding sites may result in the cooperative action of multiple RISCs and provide highly efficient inhibition of expression. The target site sequence may comprise a total of 5-100, 10-60, or more nucleotides. The target site sequence may comprise at least 5 nucleotides of the sequence of a target gene binding site.

Administration Methods

Agents described by the disclosure may be delivered to a subject in compositions according to any appropriate methods. In some embodiments, an agent (e.g., a rAAV encoding an NAA-depleting agent or an NAA-increasing agent, a small molecule, peptide, protein, nucleic acid, etc.), e.g., suspended in a physiologically compatible carrier (i.e., in a composition), may be administered to a subject, i.e. host animal, such as a human, mouse, rat, cat, dog, sheep, rabbit, horse, cow, goat, pig, guinea pig, hamster, chicken, turkey, or a non-human primate (e.g., Macaque). In some embodiments, a host animal does not include a human.

The compositions of the disclosure may comprise an agent (a rAAV encoding an NAA-depleting agent or an NAA-increasing agent, a small molecule, peptide, protein, nucleic acid, etc.) alone, or in combination with one or more other agents (e.g., a second rAAV encoding one or more different transgenes). In some embodiments, a composition comprises 1, 2, 3, 4, 5, 6, 7, 8, 9, 10, or more different agents (e.g., multiple rAAVs each encoding one or more different transgenes).

In some cases, administration of an agent to a subject elicits an immune response in the subject, for example an immune response against an rAAV capsid protein. Without wishing to be bound by any particular theory, suppressing the immune system of a subject prior to administration of an agent (e.g., a rAAV encoding an NAA-depleting agent or an NAA-increasing agent, a small molecule, peptide, protein, nucleic acid, etc.) results, in some embodiments, in increased therapeutic effect of the agent (e.g., a rAAV encoding an NAA-depleting agent or an NAA-increasing agent, a small molecule, peptide, protein, nucleic acid, etc.). Therefore, in some embodiments, a subject is administered one or more (e.g., 2, 3, 4, 5, or more) immune-suppressing agents prior to administration of an rAAV as described by the disclosure. An "immune-suppressing agent" is any composition (e.g., a protein, nucleic acid, small molecule, etc.) that reduces the immune response of a subject to an agent (e.g., a rAAV encoding an NAA-depleting agent or an NAA-increasing agent, a small molecule, peptide, protein, nucleic acid, etc.). An immune-suppressing agent can reduce the innate immune response, adaptive immune response, cellular immune response, humoral immune response, or any combination of the foregoing, in a subject.

Examples of biological immune-suppressing agents include but are not limited to monoclonal antibodies, such as monoclonal antibodies that block the co-stimulatory pathway (e.g., appropriate antibodies against CTLA4, ICOS, CD80, OX40, or other targets), interfering RNA (e.g., siRNA, dsRNA, shRNA, miRNA, etc.) targeting immunostimulatory molecules (e.g., cytokines), and proteins (e.g., proteasome inhibitors).

Examples of small molecule immune-suppressing molecules include but are not limited to glucocorticoids (e.g., cortisol, cortisone, prednisone, prednisolone, methylprednisolone, dexamethasone, betamethasone, triamcinolone, beclomethasone, fludrocortisone, deoxy corticosterone (DOCA), and aldosterone), cytostatics (e.g., cyclophosphamide, nitrosoureas, platinum compounds, methotrexate, azathioprine, mercaptopurine, fluorouracil, dactinomycin, etc.), immunophilin-targeting drugs (e.g., cyclosporine, tacrolimus, sirolimus, rapamycin, etc.), interferons (e.g., IFN-β), mycophenolate, fingolimod, and myriocin.

An immune-suppressing agent can be administered to a subject at between about one week and one minute prior to administration of an agent (e.g., rAAV encoding an NAA-depleting agent or an NAA-increasing agent, a small molecule, peptide, protein, nucleic acid, etc.) as described by the disclosure. In some embodiments, an immune-suppressing agent is administered to a subject between about 5 days, about 1 day, about 12 hours, about 2 hours, about 1 hour, about 30 minutes, about 10 minutes, about 5 minutes, or about 1 minute prior to administration of an agent (e.g., a rAAV encoding an NAA-depleting agent or an NAA-increasing agent, a small molecule, peptide, protein, nucleic acid, etc.). In some embodiments, a subject is administered an immune-suppressing agent on multiple (e.g. 2, 3, 4, 5, 6, 7, 8, 9, 10, or more) occasions prior to administration of an agent (e.g., a rAAV encoding an NAA-depleting agent or an NAA-increasing agent, a small molecule, peptide, protein, nucleic acid, etc.) to the subject.

In some embodiments, a composition further comprises a pharmaceutically acceptable carrier. Suitable carriers may be readily selected by one of skill in the art in view of the indication for which the agent (e.g., a rAAV encoding an NAA-depleting agent or an NAA-increasing agent, a small molecule, peptide, protein, nucleic acid, etc.) is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the agent (e.g., a rAAV encoding an NAA-depleting agent or an NAA-increasing agent, a small molecule, peptide, protein, nucleic acid, etc.) and carrier(s), other pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

In some embodiments, the agent or agents (e.g. a rAAV encoding an NAA-depleting agent or an NAA-increasing agent, a small molecule, peptide, protein, nucleic acid, etc.) are administered in sufficient amounts to transfect the cells of a desired tissue (e.g., tumor tissue) and to provide sufficient levels of gene transfer and expression without undue adverse effects. Examples of pharmaceutically acceptable routes of administration include, but are not limited to, direct delivery to the selected organ (e.g., intrathecal, intracerebral), oral, inhalation (including intranasal and intratracheal delivery), intraocular, intravenous, intramuscular, subcutaneous, intradermal, intratumoral, and other parental routes of administration. Routes of administration may be combined, if desired.

In some embodiments, the dose of rAAV virions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors.

Generally, an "effective amount" is the amount of an agent sufficient to increase or deplete the expression or activity of NAA or ASPA in a cell. In some embodiments, an effective amount is the amount of an agent sufficient to alleviate a symptom, delay or slow the progression of a disease (e.g., slowing or inhibiting tumor growth) in a subject. In some embodiments, an effective amount of an rAAV is an amount sufficient to target infect an animal, target a desired tissue. In some embodiments, an effective amount of an rAAV is an amount sufficient to produce a stable somatic transgenic animal model. The effective amount will depend primarily on factors such as the species, age, weight, health of the subject, and the tissue to be targeted, and may thus vary among animal and tissue. For example, an effective amount of the rAAV is generally in the range of from about 1 ml to about 100 ml of solution containing from about $10^9$ to $10^{16}$ genome copies (gc). In some embodiments, a dosage between about $10^{10}$ and $10^{15}$ genome copies is appropriate. In some cases, a dosage between about $10^{11}$ to $10^{13}$ rAAV genome copies is appropriate. In certain embodiments, $10^{11}$ or $10^{12}$ rAAV genome copies is effective to target CNS tissue. In some embodiments, a dosage of an rAAV is calculated based upon the weight of the subject to which the rAAV is being administered. For example, in some embodiments, a dosage between $1.0\times10^{10}$ gc/kg and $1.0\times10^{15}$ gc/kg is appropriate. In some embodiments, a dosage of $2.0\times10^{10}$ gc/kg, $2.0\times10^{11}$ gc/kg, $2.0\times10^{12}$ gc/kg, $2.0\times10^{13}$ gc/kg, $2.0\times10^{14}$ gc/kg, or $2.0\times10^{15}$ gc/kg is appropriate. In some cases, stable transgenic animals are produced by multiple doses of an rAAV.

In some embodiments, a dose of an agent (e.g., a rAAV encoding an NAA-depleting agent or an NAA-increasing agent, a small molecule, peptide, protein, nucleic acid, etc.) is administered to a subject no more than once per calendar day (e.g., a 24-hour period). In some embodiments, a dose of an agent (e.g., a rAAV encoding an NAA-depleting agent or an NAA-increasing agent, a small molecule, peptide, protein, nucleic acid, etc.) is administered to a subject no more than once per 2, 3, 4, 5, 6, or 7 calendar days. In some embodiments, a dose of an agent (e.g., a rAAV encoding an NAA-depleting agent or an NAA-increasing agent, a small molecule, peptide, protein, nucleic acid, etc.) is administered to a subject no more than once per calendar week (e.g., 7 calendar days). In some embodiments, a dose of an agent (e.g., a rAAV encoding an NAA-depleting agent or an NAA-increasing agent, a small molecule, peptide, protein, nucleic acid, etc.) is administered to a subject no more than bi-weekly (e.g., once in a two calendar week period). In some embodiments, a dose of an agent (e.g., a rAAV encoding an NAA-depleting agent or an NAA-increasing agent, a small molecule, peptide, protein, nucleic acid, etc.) is administered to a subject no more than once per calendar month (e.g., once in 30 calendar days). In some embodiments, a dose of an agent (e.g., a rAAV encoding an NAA-depleting agent or an NAA-increasing agent, a small molecule, peptide, protein, nucleic acid, etc.) is administered to a subject no more than once per six calendar months. In some embodiments, a dose of an agent (e.g., a rAAV encoding an NAA-depleting agent or an NAA-increasing agent, a small molecule, peptide, protein, nucleic acid, etc.) is administered to a subject no more than once per calendar year (e.g., 365 days or 366 days in a leap year).

In some embodiments, rAAV compositions are formulated to reduce aggregation of AAV particles in the composition, particularly where high rAAV concentrations are present (e.g., ~$10^{13}$ GC/ml or more). Appropriate methods for reducing aggregation of may be used, including, for example, addition of surfactants, pH adjustment, salt concentration adjustment, etc. (See, e.g., Wright F R, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens. Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In some embodiments, agents (e.g., a rAAV encoding an NAA-depleting agent or an NAA-increasing agent, a small molecule, peptide, protein, nucleic acid, etc.) in suitably formulated pharmaceutical compositions disclosed herein are delivered directly to target tissue, e.g., direct to tumor tissue. However, in certain circumstances it may be desirable to separately or in addition deliver the therapeutic agents via another route, e.g., subcutaneously, intraopancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver an agent or agents.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a suitable sterile aqueous medium may be employed. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active agent in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, compositions described by the disclosure may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500.ANG., containing an aqueous solution in the core.

Alternatively, nanocapsule formulations may be used. Nanocapsules can generally entrap substances in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use.

EXAMPLES

Example 1

Modulation of Metabolic Balance in Cells

Figure 1B:
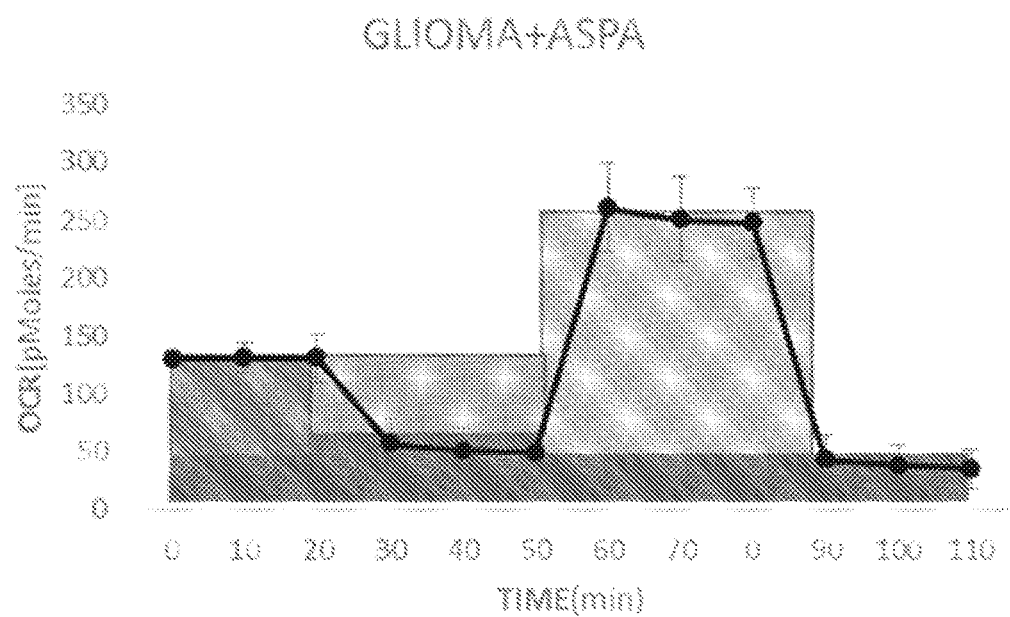

Metabolic profiling was performed in U87 glioma cells. FIG. 1A shows representative data for metabolic profiling of control (untreated) U87 glioma cells, as measured by oxygen consumption rate (OCR) using a Seahorse HF instrument. FIG. 1B shows representative data for metabolic profiling of U87 glioma cells that were administered a recombinant adeno-associated virus that expresses aspartoacylase (ASPA) (referred to as rAAV-ASPA), as measured by oxygen consumption rate (OCR) using a Seahorse HF instrument. A reduction in non-mitochondrial respiration (e.g., respiration associated with glycolysis), and an increase in maximal respiration (e.g., including fatty acid metabolism, such as beta-oxidation) was observed in rAAV-ASPA-treated cells compared with untreated control cells.

Figure 2:
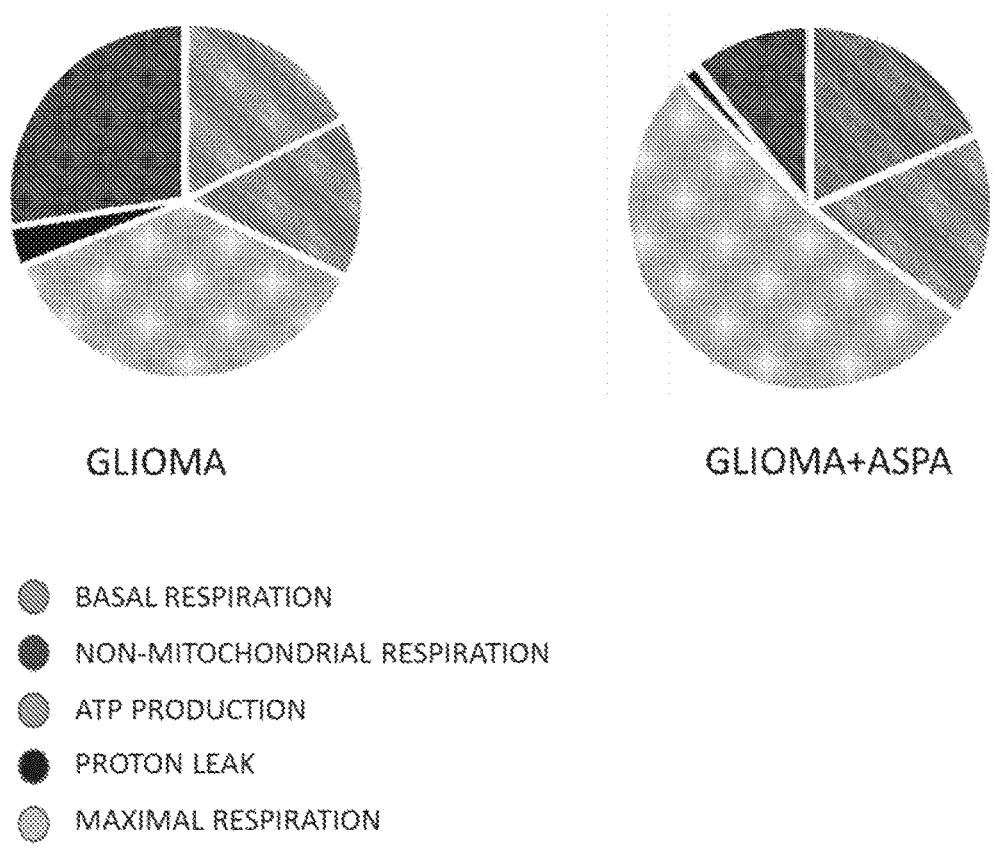
FIG. 2 shows representative data for metabolic profiling of glioma cells (U87). Data indicate that rAAV-ASPA administration results in a reduction in non-mitochondrial respiration and an increase in maximal respiration in the cells.
Figure 3A:
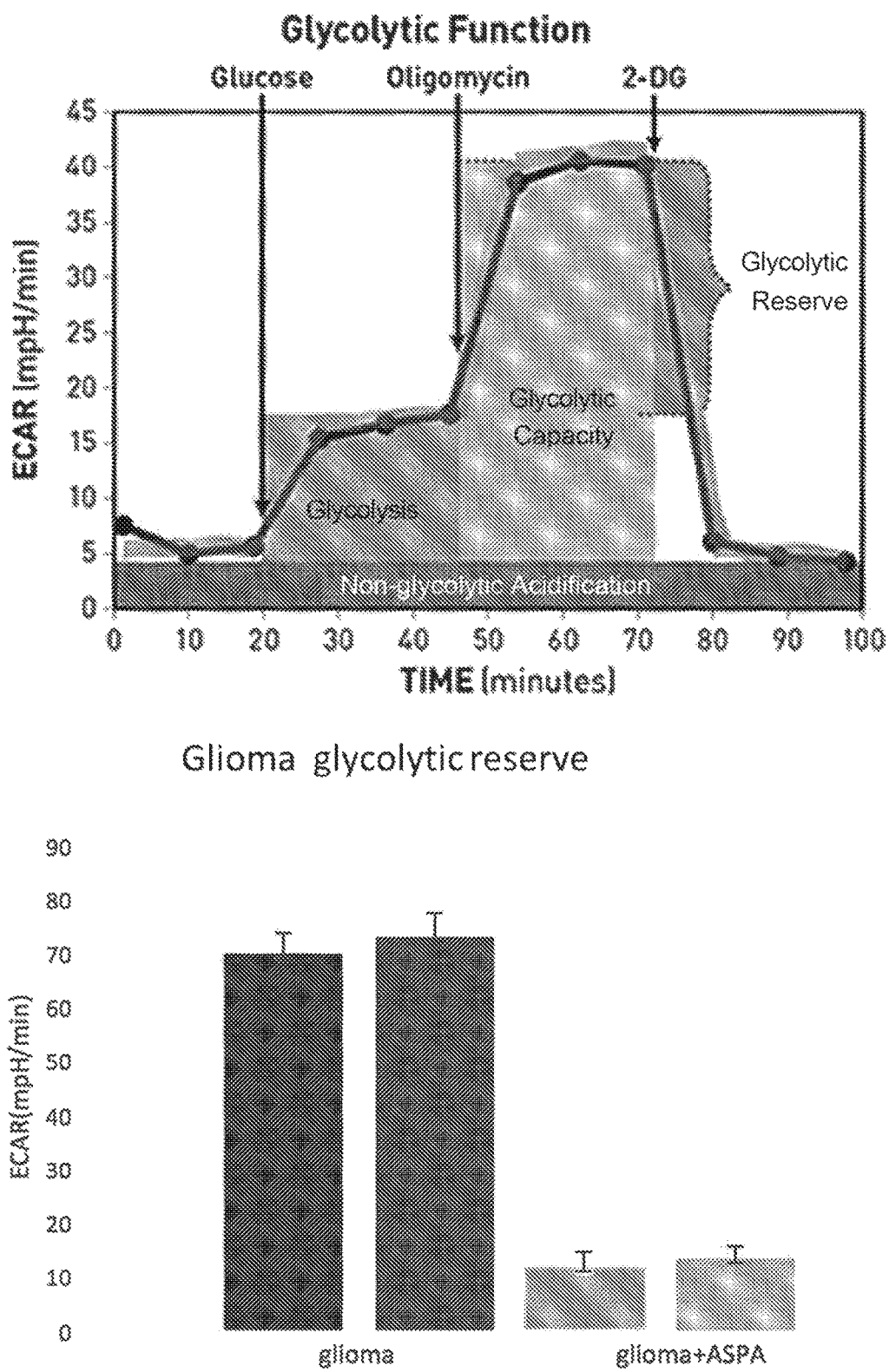
FIGS. 3A-3B show representative data for metabolic profiling of glioma cells (U87).
Figure 3B:
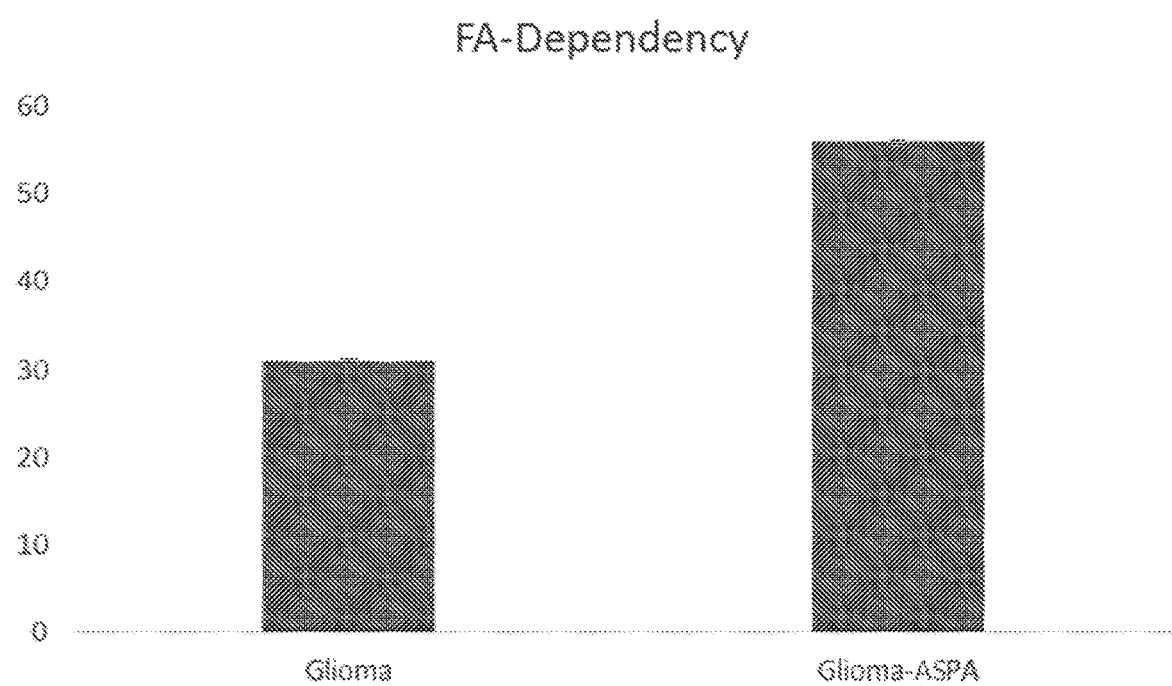

Glycolytic reserves and fatty acid metabolism were quantified. Data indicated that metabolic activity in untreated glioma cells was shifted towards glycolysis, relative to rAAV-ASPA-treated cells (FIG. 2 and FIG. 3A). Metabolic activity in the glioma cells treated with rAAV-ASPA shifted away from glycolysis and towards beta-oxidation (FIG. 2 and FIG. 3B).

Taken together, these data indicate that administering an NAA-depleting agent (e.g., ASPA) to a cell having a metabolic imbalance (or having a disease characterized by a metabolic imbalance, such as cancer), in some embodiments, modulates or shifts metabolic activity to restore balance between glycolysis and beta-oxidation.

Example 2

Pathomechanism of Canavan's Disease

Experimental Design

Global biochemical profiles were determined in mouse brain tissue collected from postnatal day 25 (P25) mice representing treatment groups shown below in Table 1.

TABLE 1

Treatment groups

| Group | n | Description |
|---|---|---|
| WT | 8 | Wild type mouse |
| KO | 8 | Aspartoacylase gene knockout mouse |
| rAAV Ctrl | 8 | Aspartoacylase gene knockout mouse, treated with virus with a promoter-less expression construct |
| rAAV Tx | 8 | Aspartoacylase gene knockout mouse, treated with virus encoding the human ASPA gene |

Metabolomics of Healthy and Canavan Disease Mouse Brains

Figure 5:
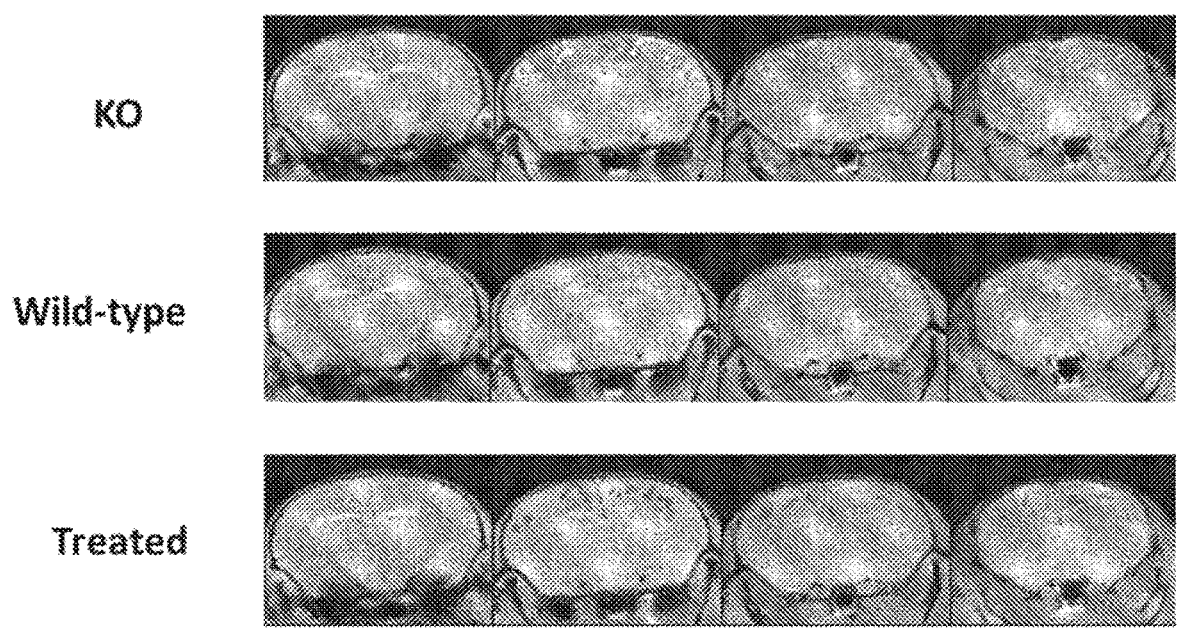
FIG. 5 shows data illustrating that Canavan disease (CD) causes increased oxygen consumption for functional neuro-connectivity, as measured by resting state functional MRI (RS-fMRI).

Results of resting state functional MRI (RS-fMRI) indicate that Canavan disease causes increased oxygen consumption for functional neuro-connectivity (FIG. 5). Further, Canavan disease causes increased oxygen consumption for cortical/sub-cortical connectivity (FIG. 6). These data indicate that Canavan disease may be characterized by an altered metabolic state in the CNS.

The molecular phenotype of brains of mice having Canavan disease was investigated by using a whole brain metabolomics approach. Canavan disease were treated with intravenous (IV) injection of rAAV-ASPA at p1. Healthy and CD mouse brains (both untreated and treated groups) were homogenized and subjected to metabolic analysis. Over 452 metabolites were quantified in each wild-type, untreated, treated and treatment control groups (Table 2). This large data set revealed several crucial and entirely new aspects about Canavan disease pathomechanism, its gene therapy, CNS metabolism and novel function of AspA in general.

TABLE 2

Metabolomics analysis results

| Significantly Altered Biochemicals | Total Biochemicals $p \leq 0.05$ | Biochemicals ($\uparrow\downarrow$) | Total Biochemicals $0.05 < p < 0.10$ | Biochemicals ($\uparrow\downarrow$) |
|---|---|---|---|---|
| KO WT | 273 | 68\|205 | 32 | 7\|25 |
| rAAV Tx rAAV Ctrl | 286 | 190\|96 | 29 | 14\|15 |
| rAAV Ctrl WT | 293 | 81\|212 | 30 | 12\|18 |
| rAAV Tx WT | 88 | 20\|68 | 41 | 9\|32 |
| rAAV Ctrl KO | 44 | 26\|18 | 32 | 16\|16 |
| rAAV Tx KO | 257 | 184\|73 | 41 | 21\|20 |

Statistical Analysis

Figure 7B:
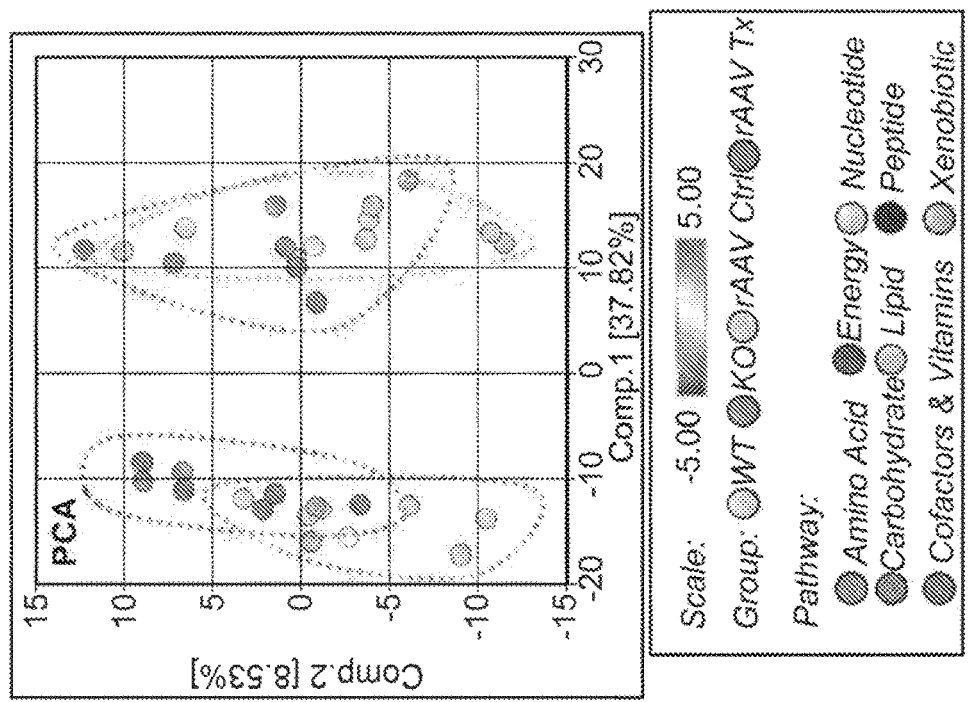
FIGS. 7A-7B show statistical analysis of whole brain metabolome in wild-type (WT) and ASPA knockout (KO) mice. Treated mice were administered rAAV-ASPA via intravenous injection at P1. Neuormetabolome data was analyzed at P25; N=8.
Figure 7A:
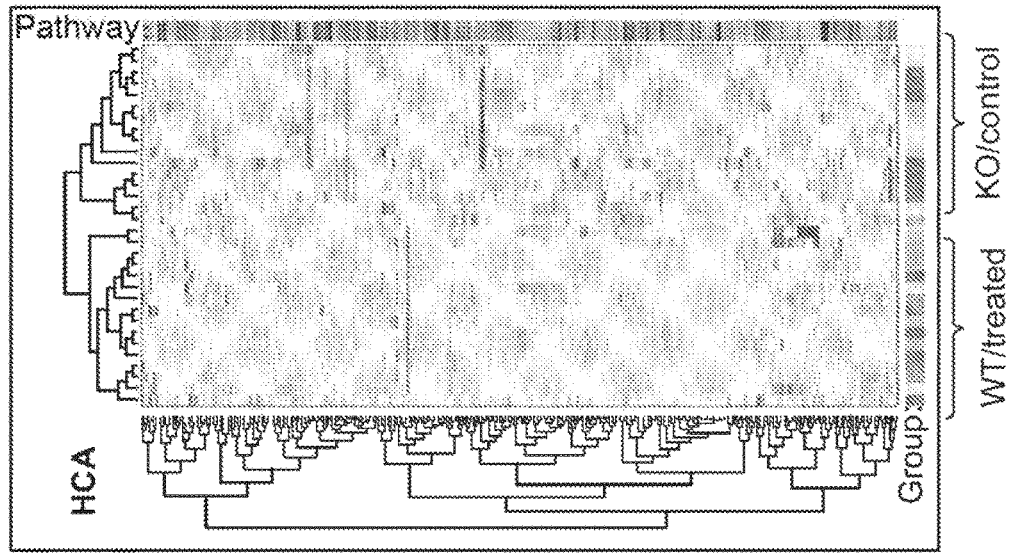

Principal component analysis (PCA) transforms a large number of metabolic variables into a smaller number of orthogonal variables (Component 1, Component 2, etc.) in order to analyze variation between groups and to provide a high-level overview of the dataset. In the PCA (FIG. 7A), samples formed into two populations; interestingly, rather than reflecting the genetic background, these two populations appeared to reflect disease state: WT and rAAV Tx formed the left-most population, with KO and rAAV Ctrl forming the right population, consistent with a "rescue" of disease by treatment.

Figure 4:
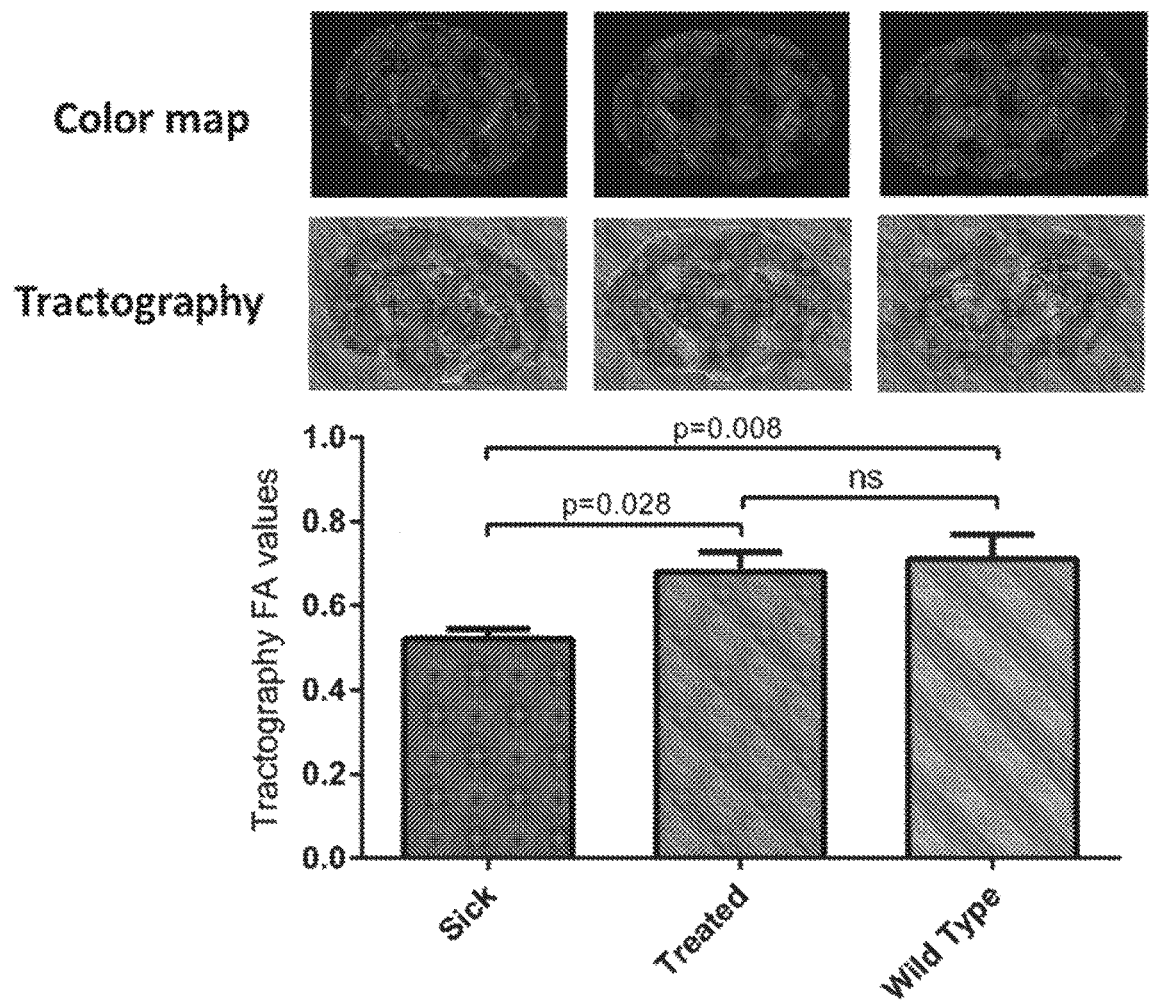
FIG. 4 shows data illustrating that rAAV-ASPA gene therapy restores the thalamo-cortical tract in animals that have a disease associated with a metabolic imbalance (Canavan's disease, CD), as measured by diffusion tensor imaging (DTI) for brain water flow.

The hierarchical clustering analysis (HCA) analyzes similarities between groups (FIG. 7B); consistent with observations in the PCA, the top-level separation of the dendrogram distinguished between WT and rAAV Tx samples (on the left) and KO and rAAV samples (on the right), with subclusters forming by individual samples by group. It is striking that both the PCA and HCA grouped the WT and rAAV Tx samples together. A high-level assessment of patterns of metabolic changes in the HCA suggests that WT and rAAV Tx tended to show similar trends in a number of metabolites, suggesting rAAV Tx was effective at modulating disease. Many of the observed changes in KO (compared to WT) trended in the opposite direction in rAAV (Tx vs Ctrl), consistent with "rescue" of disease-associated phenotypes. Consistent with the metabolic analysis, FIG. 4 shows that rAAV-ASPA gene therapy restores the thalmo-cortical tract of CD mice, as measured by diffusion tensor imaging for brain water flow.

Neurotransmitter Biosynthesis

Aspartoacylase (ASPA) is responsible for the breakdown of N-acetylaspartate (producing acetate and aspartate). Consistently, N-acetylaspartate (NAA) was increased in KO (compared to WT); treatment with rAAV-expressing ASPA resulted in a decrease in NAA (and increases in aspartate). Curiously, while NAA levels were increased (KO vs WT), the neuropeptide N-acetyl-aspartyl-glutamate (NAAG) was not significantly changed (which could reflect changes in demand or regulation of steady-state pools/pool size). Gamma-aminobutyrate (GABA) was decreased (KO vs WT), which could reflect changes in GABA-mediated signaling (GABA increased in rAAV Tx, compared to rAAV Ctrl).

Several other neurotransmitters were also detected in the dataset; while acetylcholine and serotonin were not significantly changed in KO (compared to WT), serotonin did show increases in rAAV Tx (compared to Ctrl), which could reflect changes in serotonergic signaling.

Glucose Metabolism

In the absence of disease, energetics in the brain is thought to focus on glycolytic use, with acetyl CoA input into the TCA cycle to support oxidative metabolism and macromolecule biosynthesis. Increases in glucose, glucose 6-phosphate, and an isobar of sugar diphosphates (fructose 1,6-diphosphate, glucose 1,6-diphosphate, myo-inositol 1,4 or 1,3-diphosphate) could suggest changes in glucose use or increased availability.

Glucose and related molecules (fructose, mannose and myo-inositol) were elevated, though nucleotide sugars (e.g., UDP-glucose, UDP-galactose) were decreased, which could suggest changing biosynthetic demand (KO vs WT). Three-carbon glycolytic intermediates 3-phosphoglycerate (3-PG) and phosphoenolpyruvate (PEP) were also increased; pools for these biochemicals tend to increase as glycolytic use declines.

Consistent with decreasing glycolytic use, lactate was decreased (with non-significant decrease in pyruvate). Glycogen metabolites (maltotetraose, maltotriose, and maltose) were also increased, reflecting decreased glycolytic use. Changes in energetics reflect declining energy demand (potentially associated with increased neuronal cell death or senescence) or may reflect metabolic effects of NAA accumulation in the brain.

Figure 8:
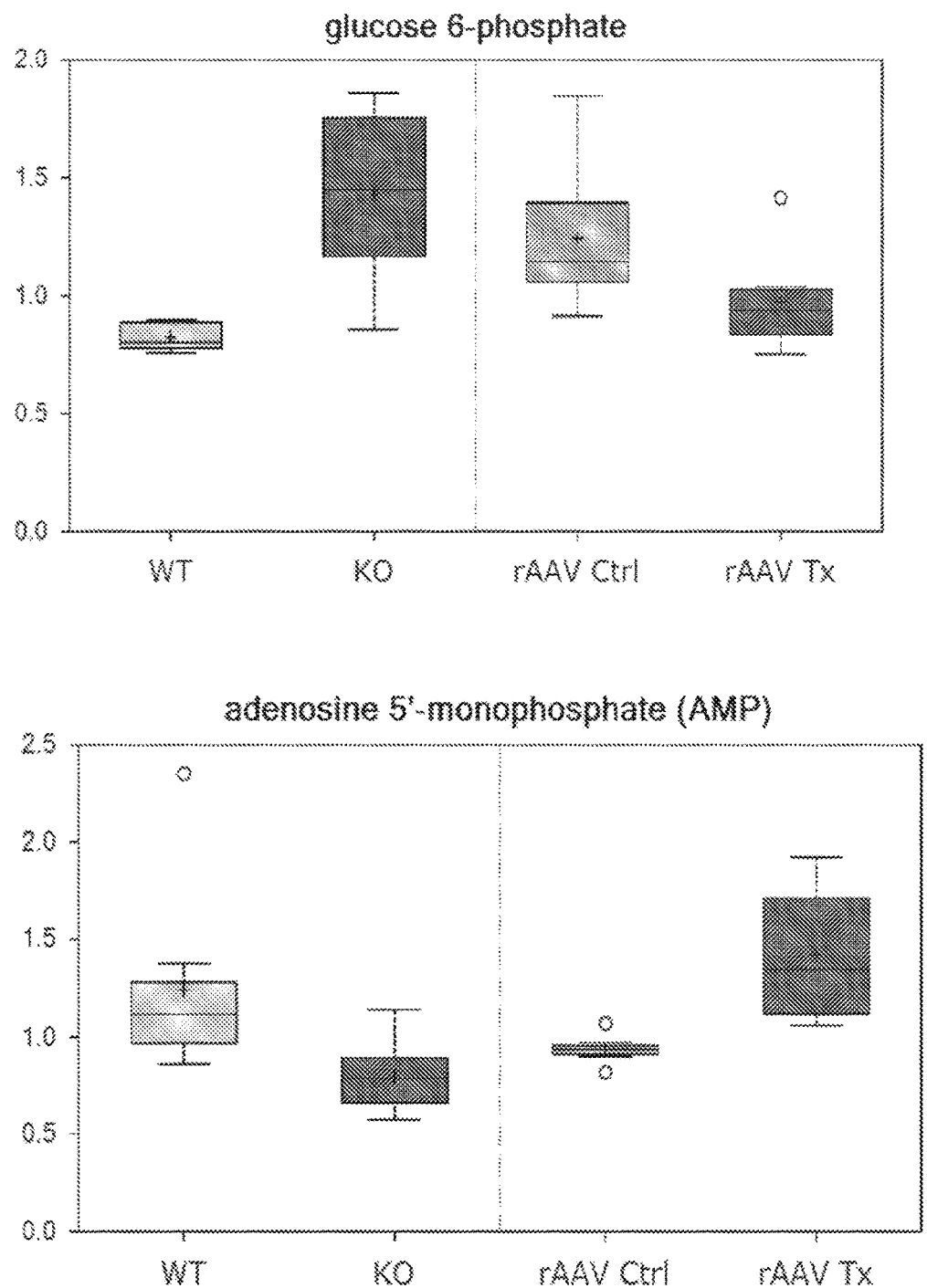
FIG. 8 shows representative data relating to levels of glucose metabolism biomarkers in WT (untreated and treated) and mice having a disease associated with a metabolic imbalance (KO, untreated and treated) mice. Treated mice were administered rAAV-ASPA.
Figure 8:
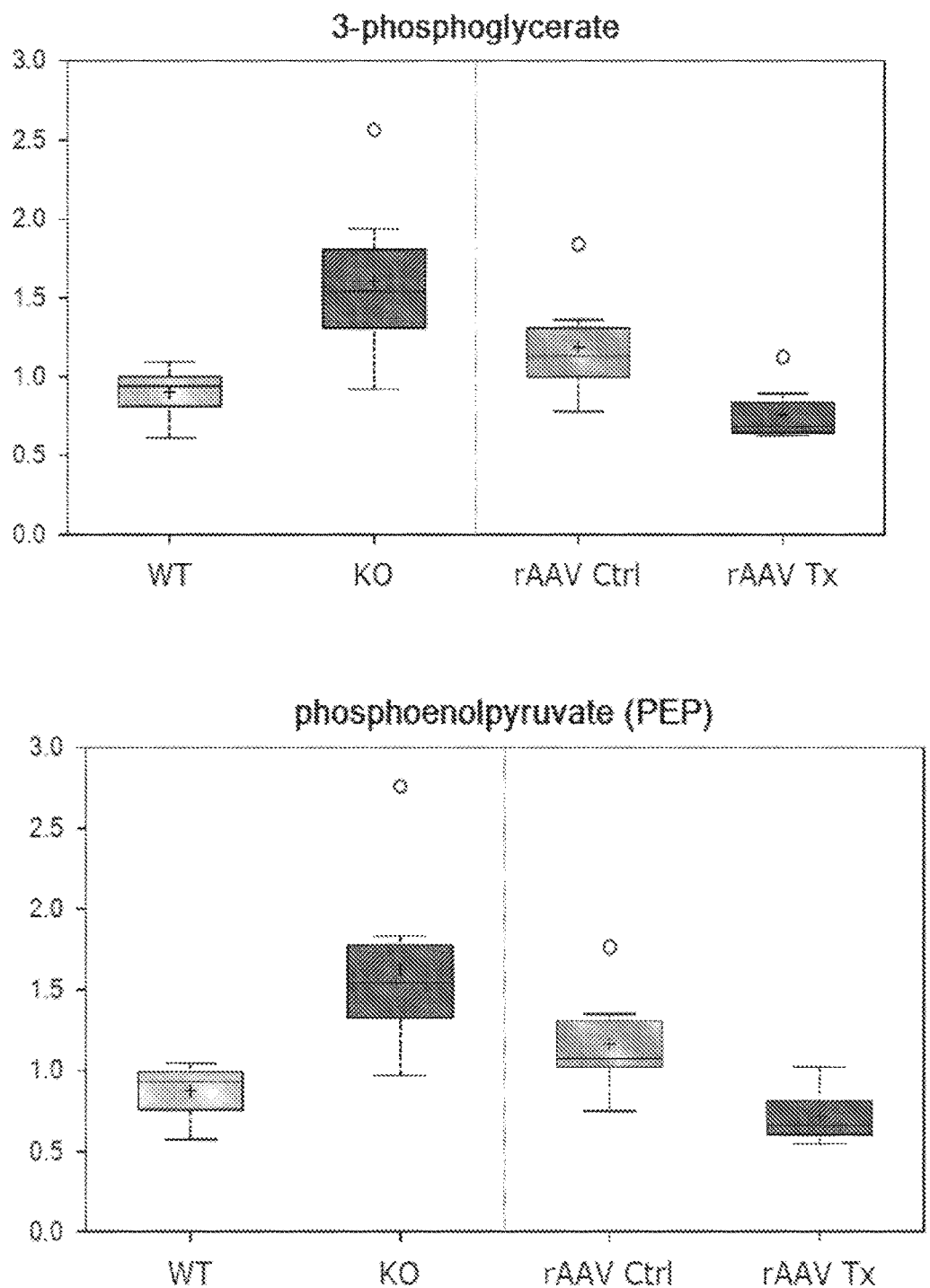
Figure 8:
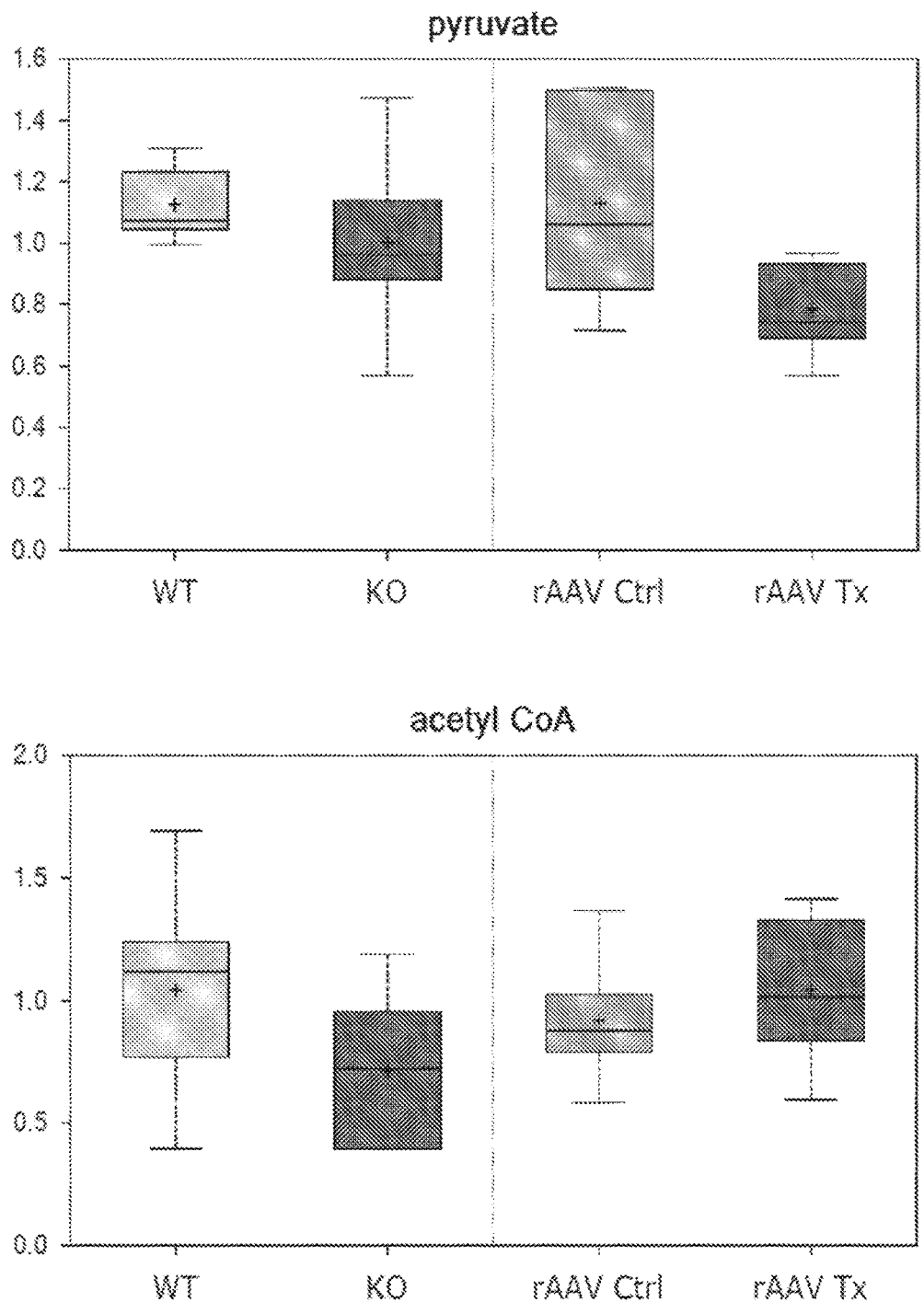
Figure 8:
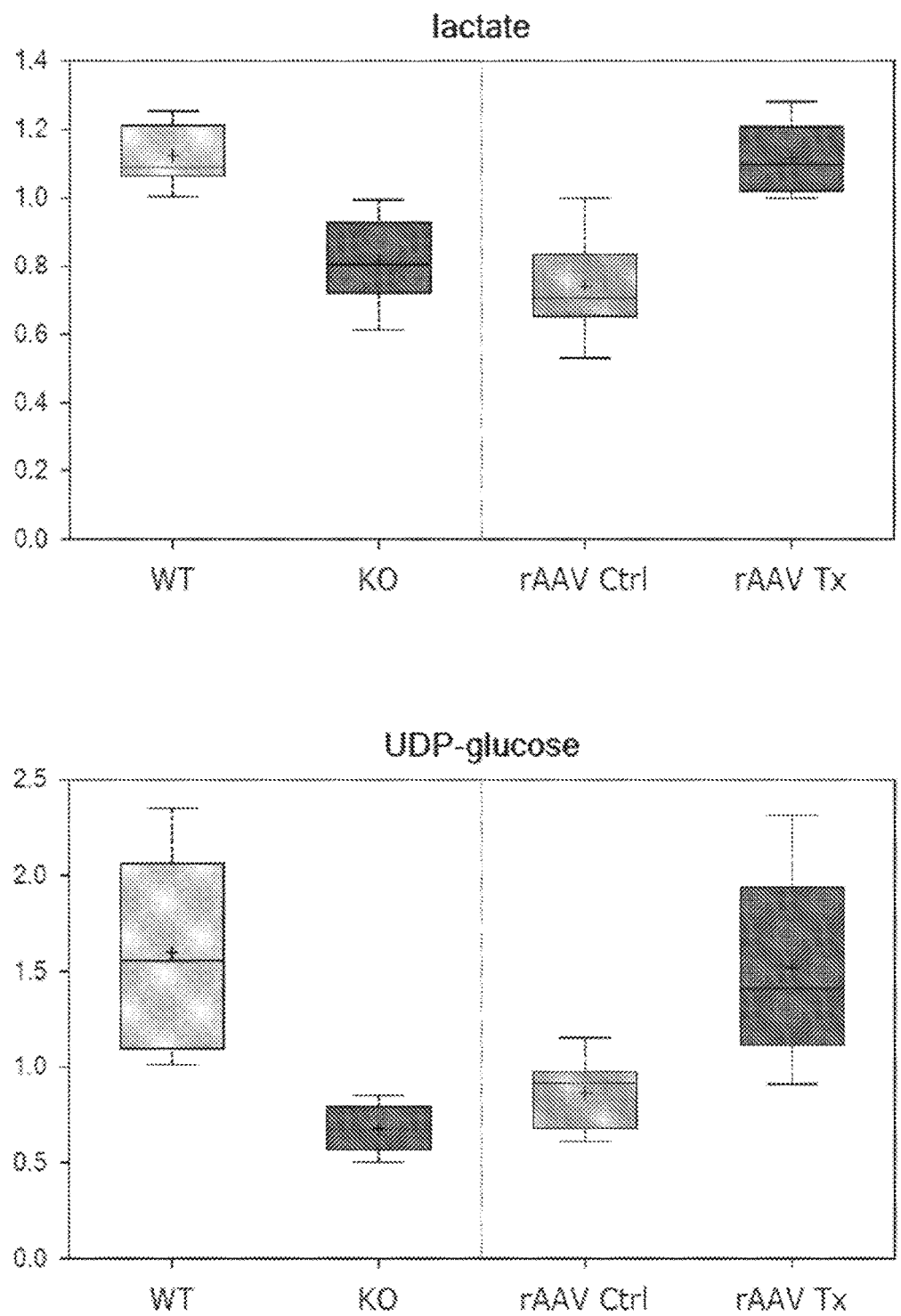
Figure 8:
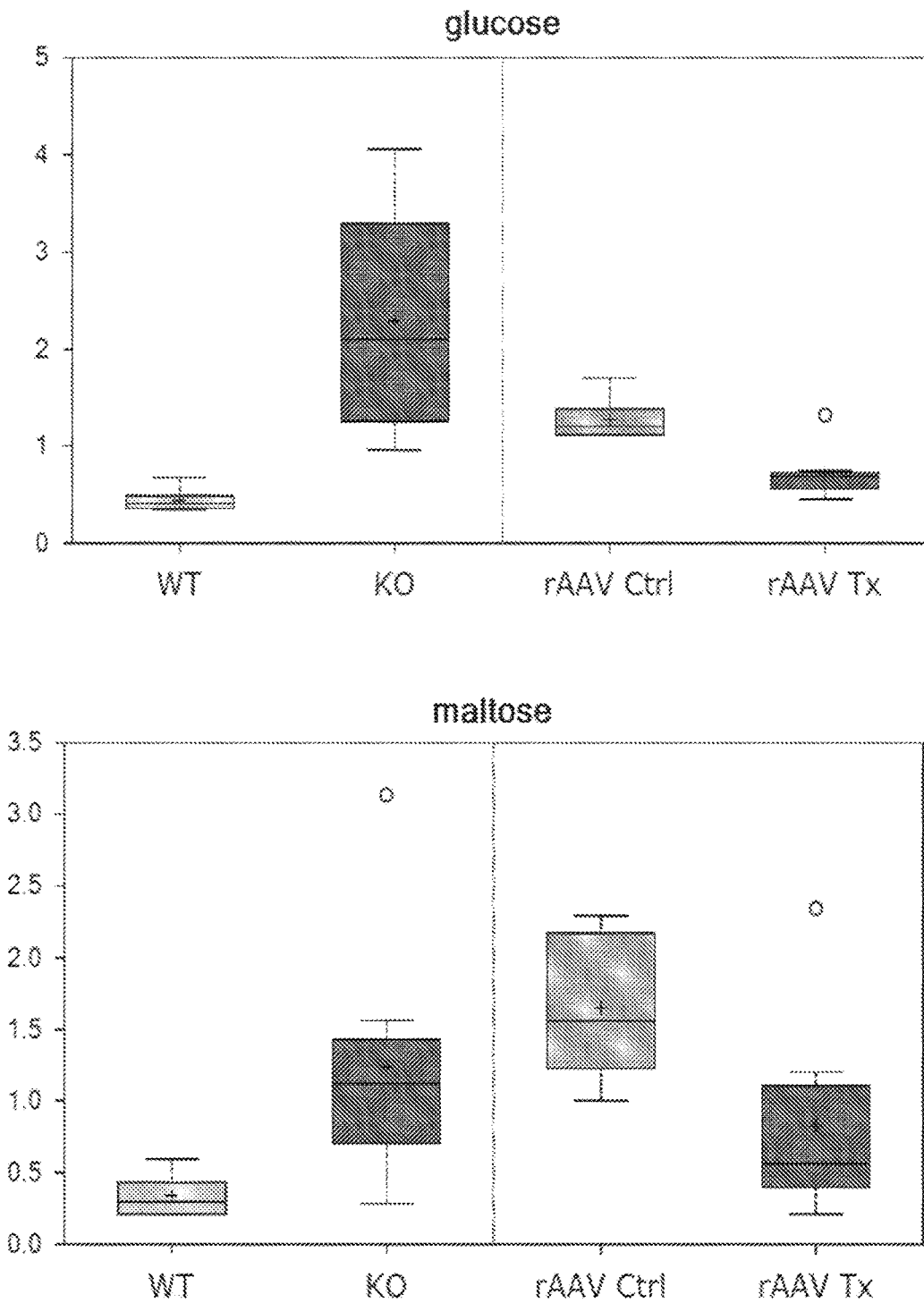
Figure 8:
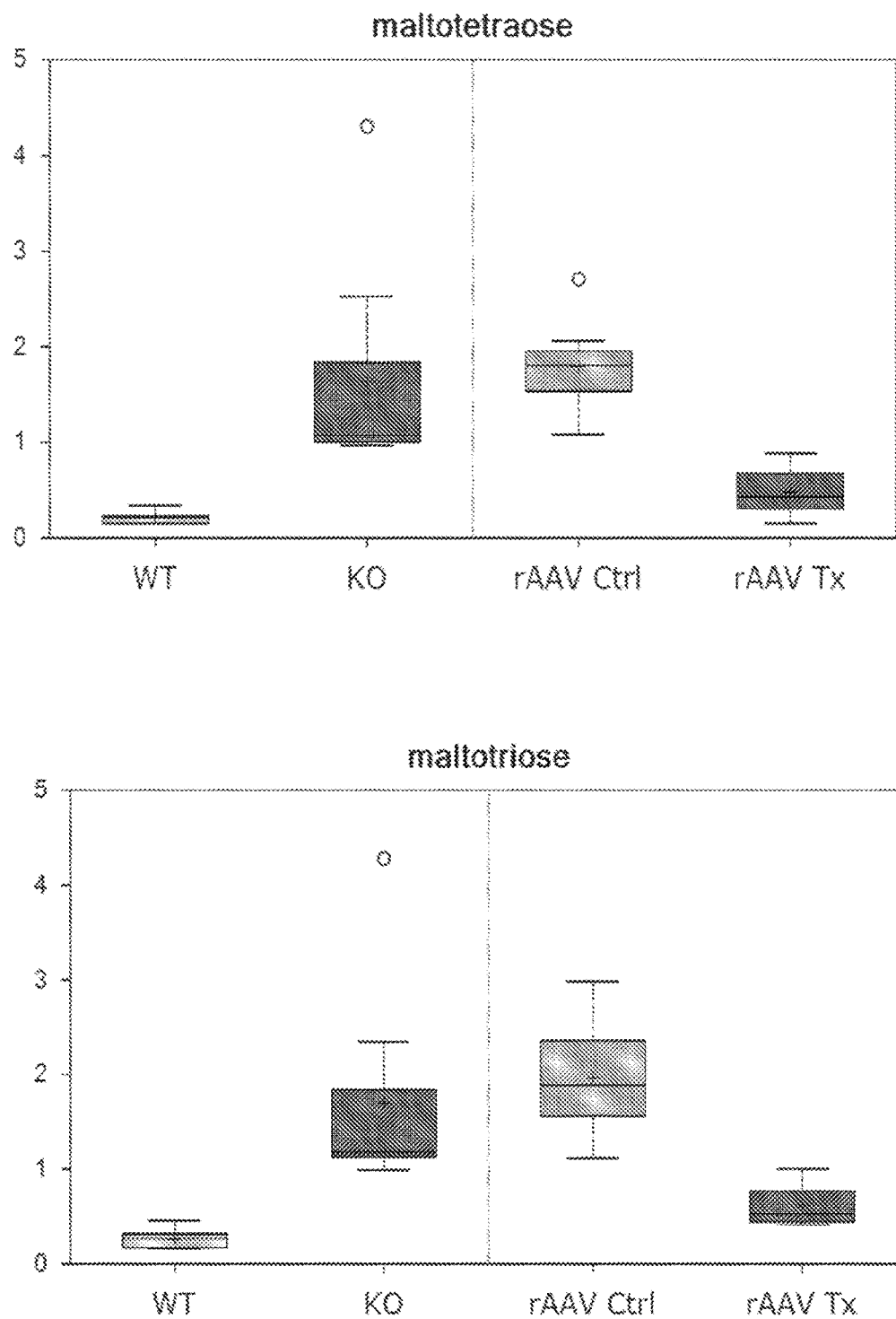

In rAAV (Tx vs Ctrl), decreases in glucose and related molecules, with increases in lactate, were suggestive of increasing glycolytic use. Interestingly, DHAP was elevated in rAAV (Tx vs Ctrl), which could reflect changing use for triglyceride biosynthesis (potentially related to a restoration of lipid biosynthesis, TAGs can be used as a precursor for phospholipids). Representative data relating to glucose metabolism is provided in FIG. 8.

Lipid Metabolism

Complex lipids, sphingolipids, diacylglycerols, monoacylglycerols, and plasmalogens were all decreased, with decreases in lysolipids, long-chain (e.g., palmitate, palmitoleate, and stearate) and polyunsaturated fatty acids, and longer acylcarnitines (e.g., myristoylcarnitine, palmitoylcarnitine) suggestive of changing availability or use to support beta-oxidation (KO vs WT). The ketone body 3-hydroxybutyrate (BHBA) was also elevated in KO (compared to WT), with decreases in malonylcarnitine (a surrogate reporter for malonyl CoA) suggestive of a shift toward increased fatty acid beta-oxidation. Increases in BHBA may also reflect changes in liver ketogenesis (or increased brain ketone uptake to supplement energetics).

Increases in carnitine, deoxycarnitine, and changes in coenzyme A precursors (increases in pantothenate with decreases in 3'-dephosphocoenzyme A and coenzyme A) could reflect changing demand or use (KO vs WT). N-acetylaspartate has been suggested as a key carrier of 2-carbon units to oligodendrocytes for lipid biosynthesis; decreases in lipids could reflect increased demand related to decreased biosynthesis.

Figure 9:
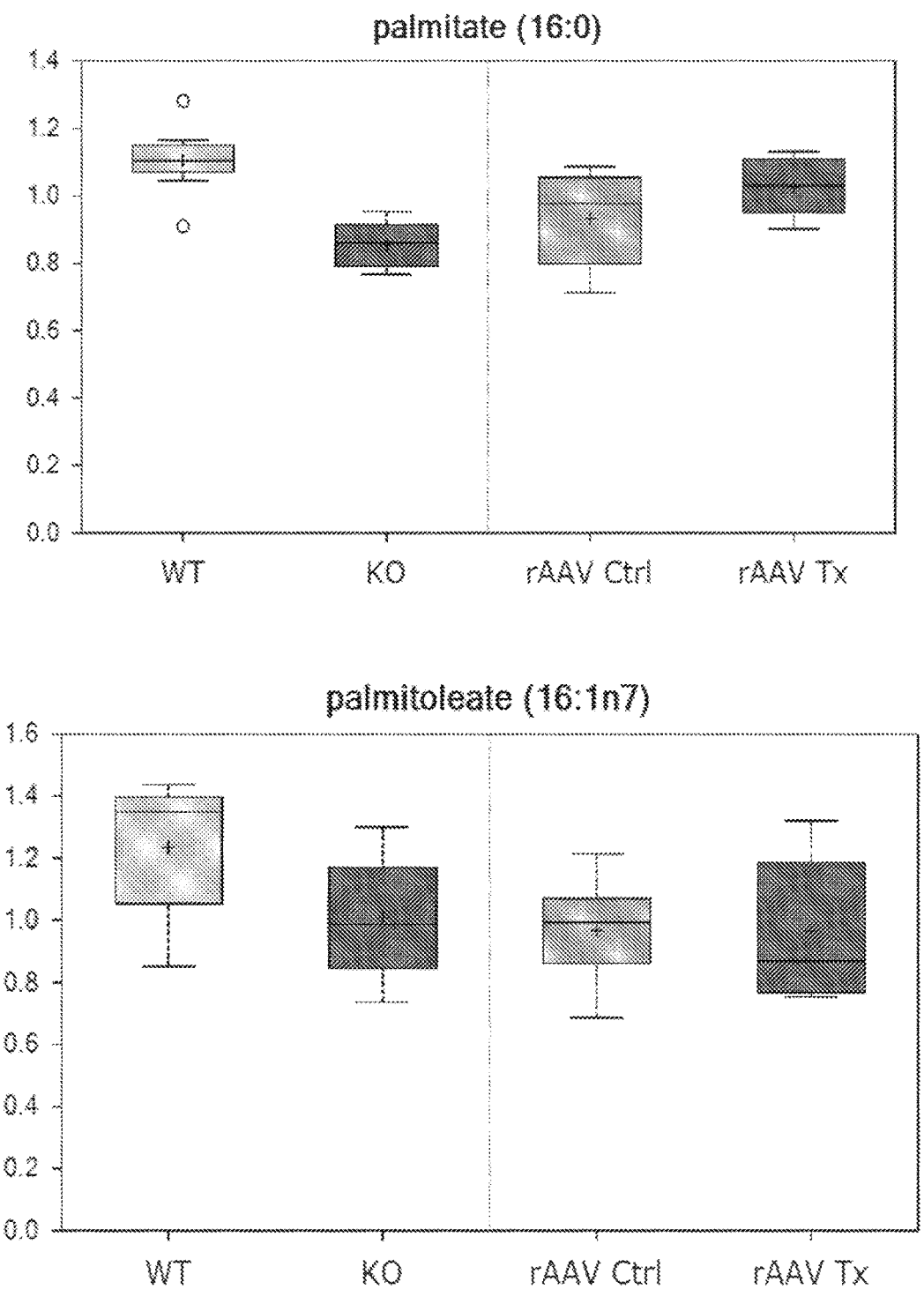
FIG. 9 shows representative data relating to levels of beta-oxidation biomarkers in WT (untreated and treated) and mice having a disease associated with a metabolic imbalance (KO, untreated and treated) mice. Treated mice were administered rAAV-ASPA.
Figure 9:
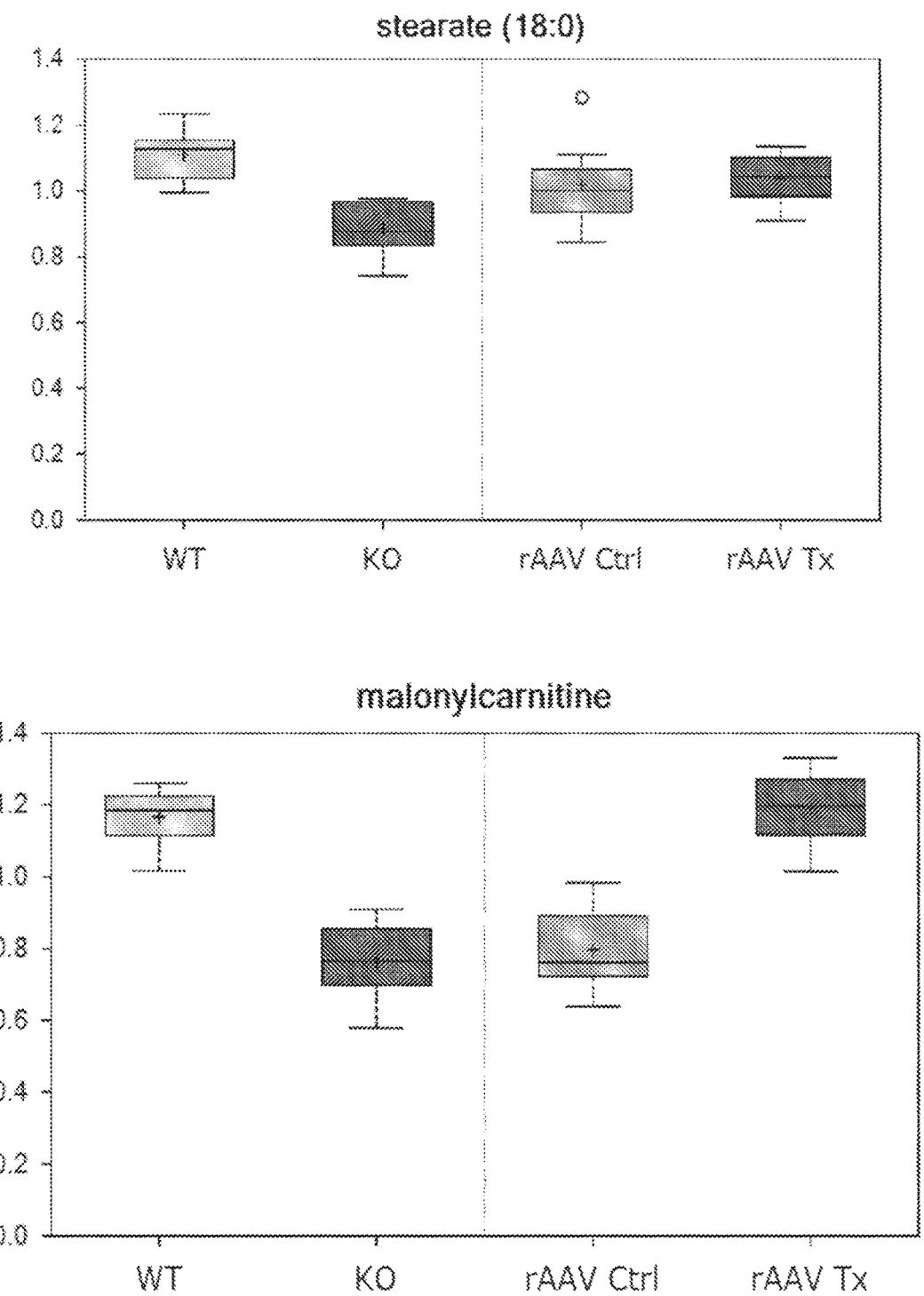
Figure 9:
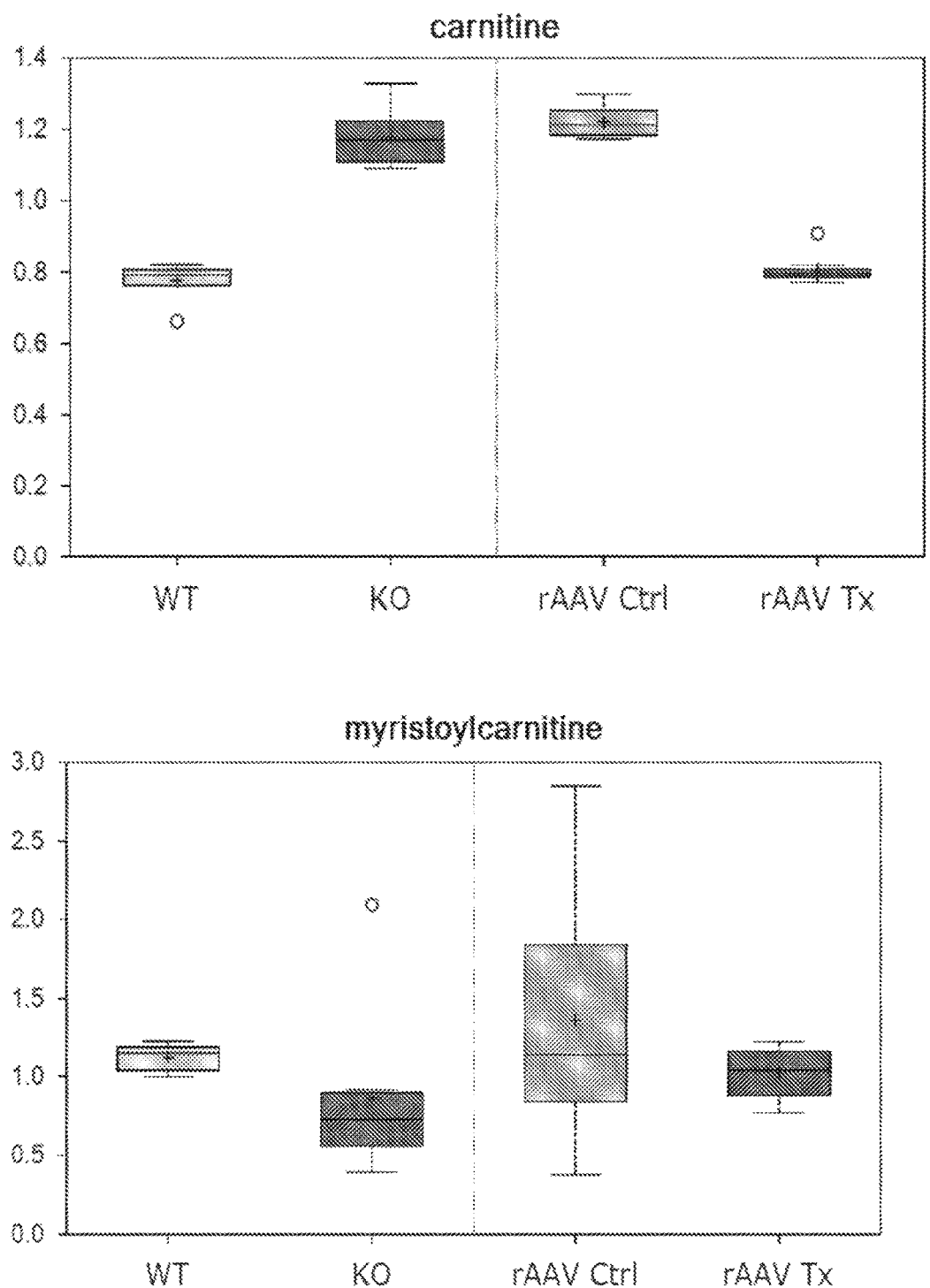
Figure 9:
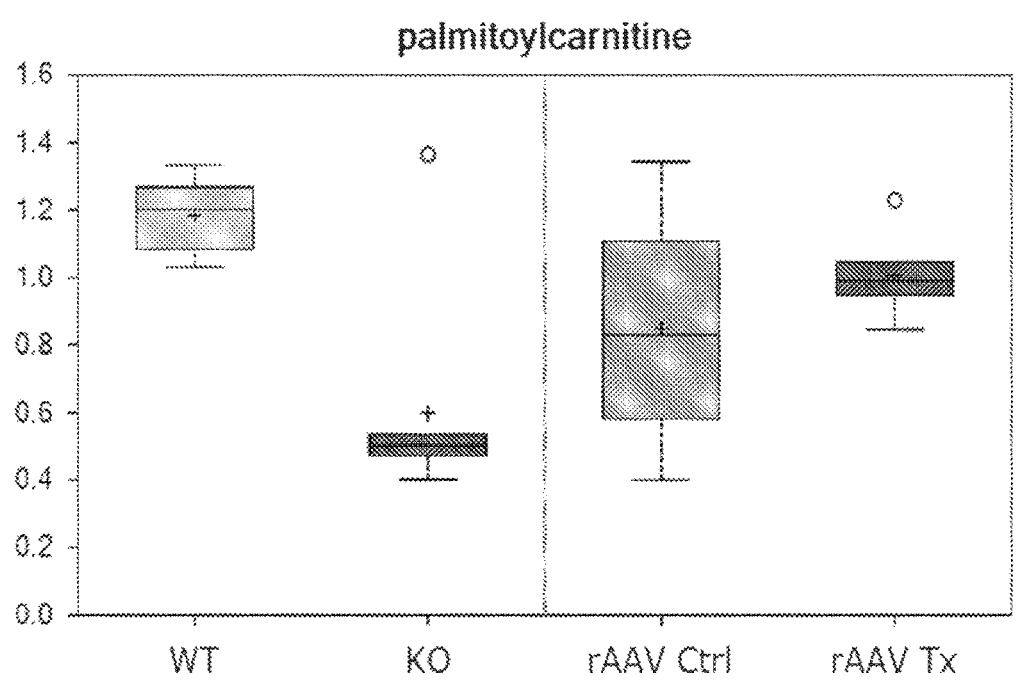

Interestingly, in rAAV (Tx vs Ctrl), increases in malonylcarnitine could imply shifts toward increased fatty acid biosynthesis; metabolites related to phospholipid biosynthesis and remodeling (e.g., choline, CDP-choline, phosphoethanolamine) were also elevated. Finally, decreases in sphingolipids (e.g., sphinganine, sphingosine, and sphingomyelins) in KO (compared to WT), with increases in serine and threonine, could reflect changing availability for myelin biosynthesis, which has been suggested as one cause of neuronal cell death in Canavan disease; rAAV (Tx vs Ctrl) showed increases in these biochemicals. Representative data relating to lipid metabolism is provided in FIG. 9.

Redox Homeostasis

Figure 10:
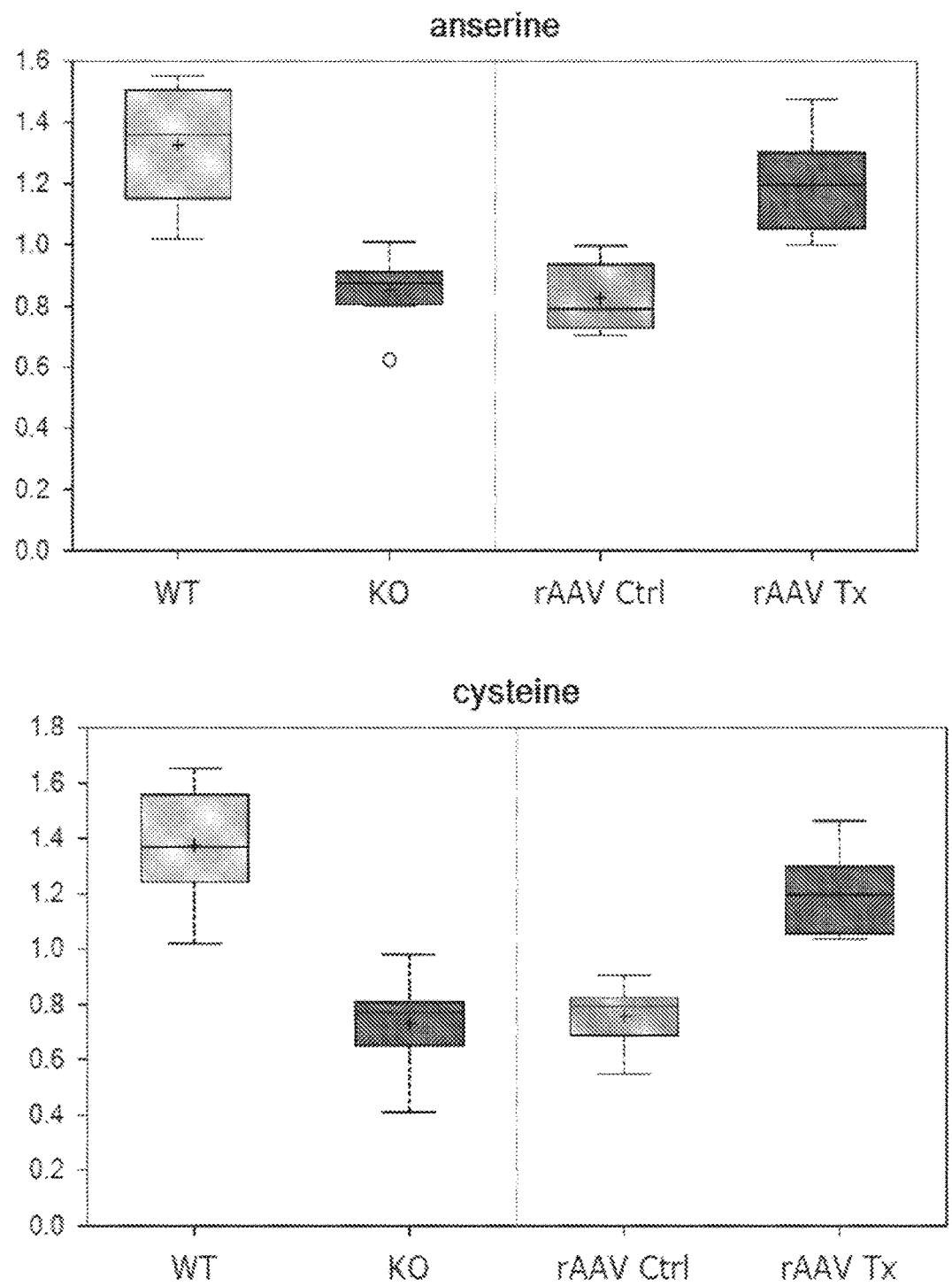
FIG. 10 shows representative data illustrating down-regulation of $O_2$ radical scavengers (e.g., anserine) and their precursor molecules (e.g., cysteine) in mice having a disease associated with a metabolic imbalance (e.g., CD mice (KO)). Treatment with rAAV-ASPA restores anserine and cysteine levels in KO mice.

Changes in metabolites related to glutathione biosynthesis (e.g., methionine, cystathionine, and cysteine) could suggest alterations in redox homeostasis in KO (compared to WT) (FIG. 10). Glutathione (either oxidized or reduced) was decreased, as were related oxidized products (S-methylglutathione and S-lactoylglutathione), likely reflecting decreased glutathione availability. Finally, gamma-glutamyl amino acids tended to decrease as a class (potentially reflecting decreased glutathione and/or amino acid availability); decreases in 5-oxoproline could indicate declining exchange of gamma-glutamyl amino acids to regenerate glutathione. Changes in KO (compared to WT) were suggestive of a less robust redox environment; however, significant differences in oxidized lipids (e.g. 4-hydroxy-nonenal-glutathione, 9/13-HODE) and products of methionine or cysteine oxidation (methionine sulfoxide, cysteine sulfinic acid) were not observed. Given the overall decrease in parent metabolites, "similar" levels in KO compared to WT may reflect a relative increase in these products (as a result of increasing oxidative stress). Changes in endogenous antioxidants, such as decreases in vitamin C metabolites (ascorbate, dehydroascorbate and threonate) and dipeptide products of histidine with anti-oxidant function (anserine (FIG. 10), homocarnosine), and increases in taurine and N-acetyltaurine, could reflect use to balance changes in redox homeostasis. Finally, changes in rAAV (Tx vs Ctrl) were consistent with decreasing oxidative stress (essentially showing inverse changes as those observed in KO vs WT).

Gene Therapy in Canavan Disease

While gene therapy in CD patients using intraparenchymal injections of ASPA expression systems was considered safe, it failed to show clinically significant improvements. Similar results were found using acetate replacement.

Figure 12:
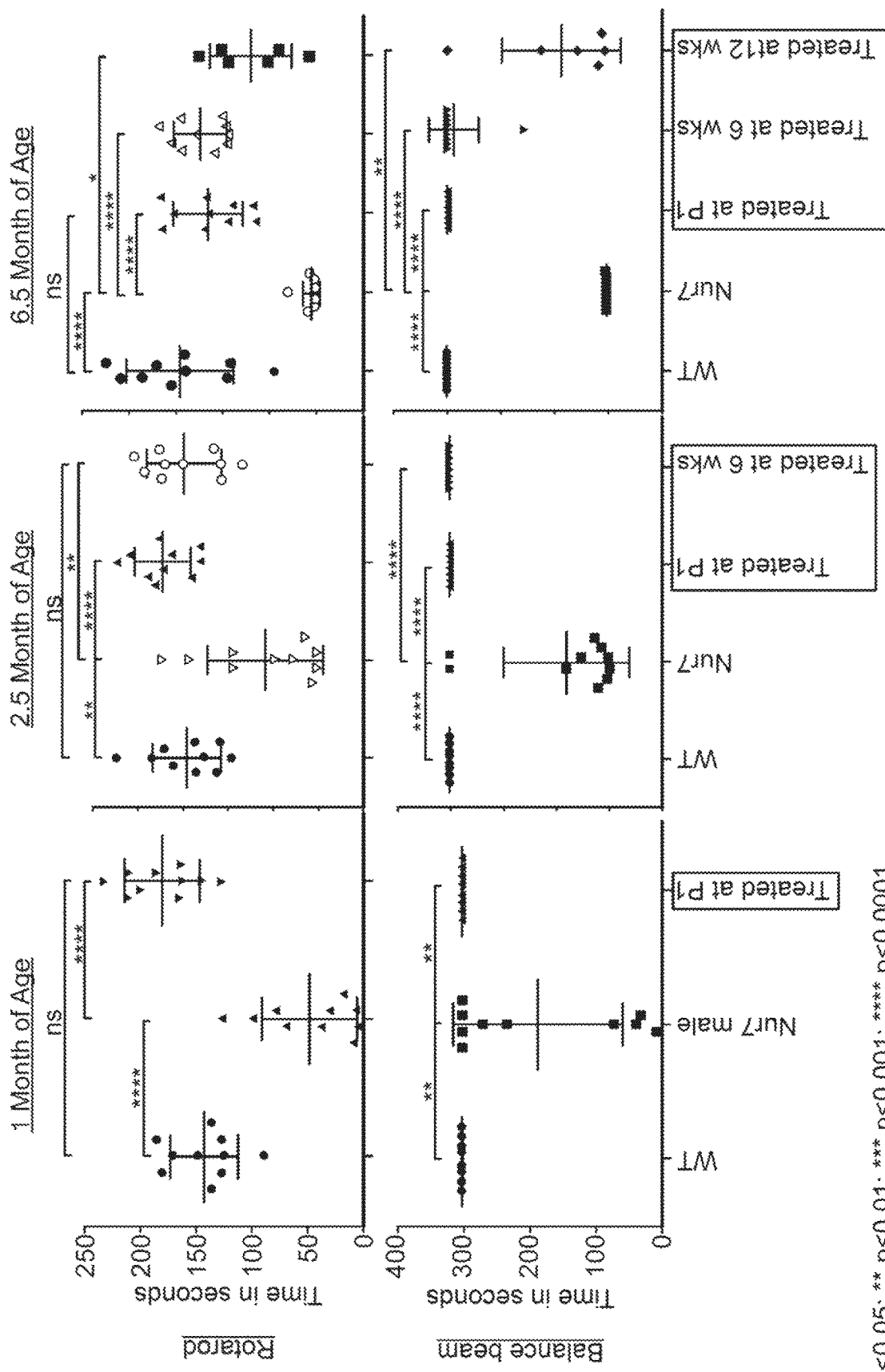
FIG. 12 shows data illustrating that administration of rAAV-ASPA restores mobility of mice having a disease associated with a metabolic imbalance (e.g., Nur7). Mice were administered rAAV-ASPA at various time points (e.g., 1 month of age, 2.5 months of age, 6.5 months of age). Psychomotor function was assessed by rotarod and balance beam tests.
Figure 14:
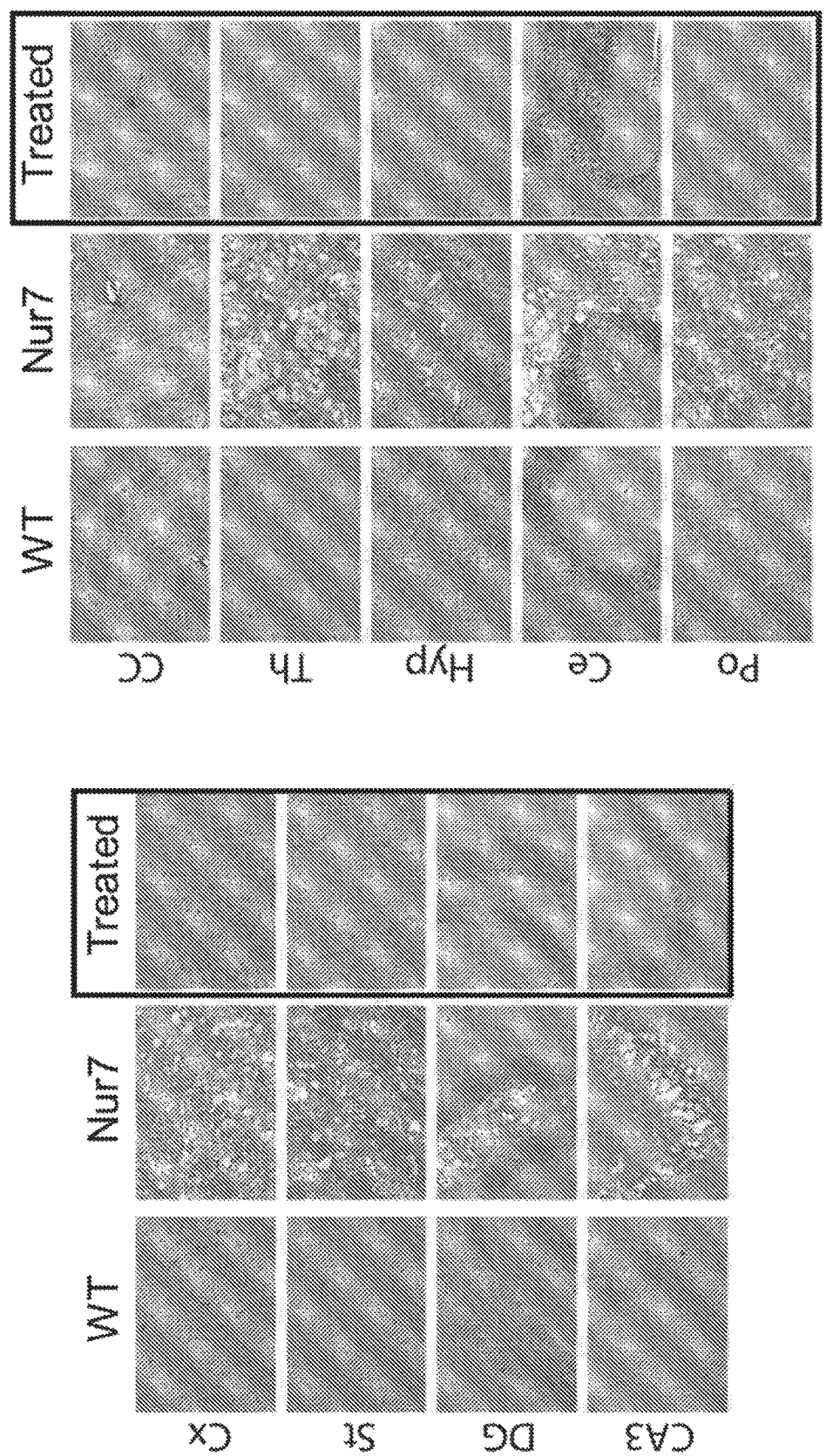
FIG. 14 shows data illustrating the rapid and efficient elimination of spongy degeneration of the CNS in Nur7 mice receiving intravenous administration of rAAV-ASPA at P1. Neuropathology was assessed at P25.
Figure 15:
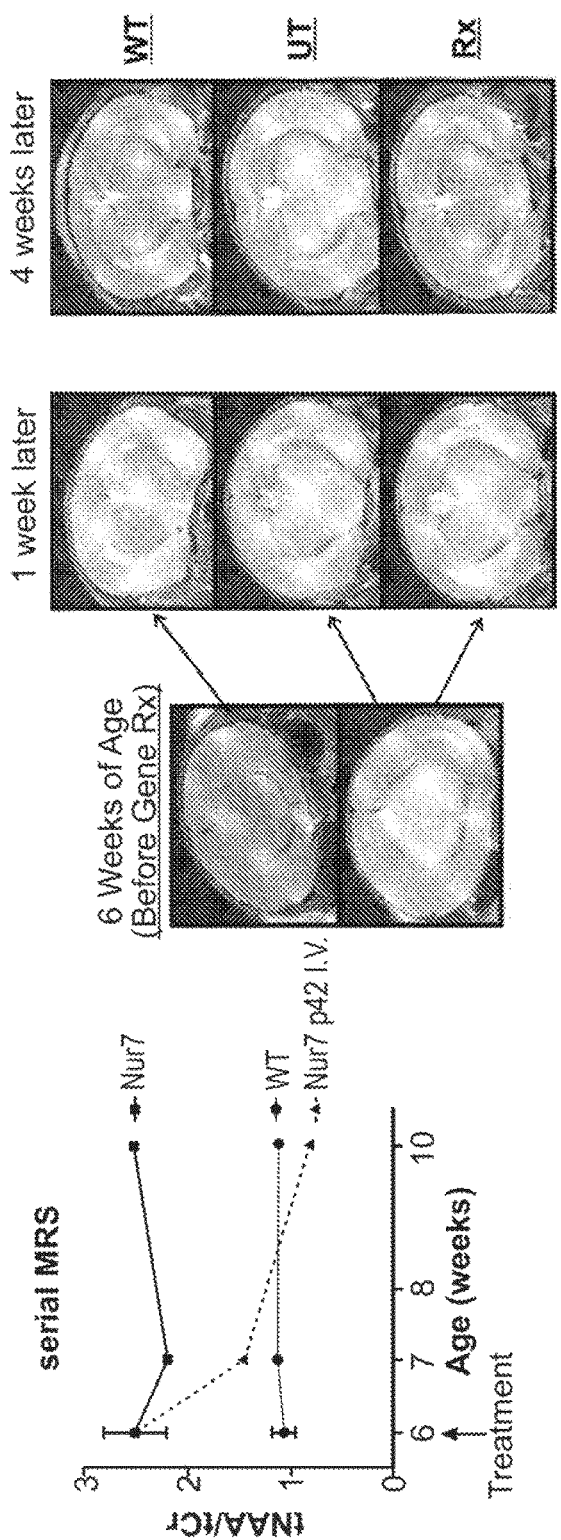
FIG. 15 shows data illustrating that administration of rAAV-ASPA rapidly reduces NAA in the brain of Nur7 mouse. Nur7 mice were treated with rAAV-ASPA at 6 weeks of age and monitored at 7 weeks and 10 weeks of age by neuroimaging.

Data described herein demonstrate that either intraventricular (e.g., direct injection) or intravenous injection (e.g., systemic) of recombinant adeno-associated virus (rAAV) expressing ASPA can cure Canavan Disease. CD mice administered rAAV expressing ASPA by either intraventricular injection show similar improvement of motor function (FIG. 11). Systemic (e.g., IV) injection of rAAV-ASPA also expands the treatment window. Experimental data indicate that rAAV-ASPA administered intravenously to Nur7 mice (a model of mild CD) as late as 3 months of age results in restoration of mobility (FIG. 12) and improvement of cognitive function (FIG. 13). Further, intravenous delivery of rAAV-ASPA results in rapid and efficient elimination of spongy degeneration of the CNS (FIG. 14) in Nur7 mice receiving treatment at P1. Importantly, intravenous administration of rAAV-ASPA results in rapid reduction of NAA in the brain of Nur7 mice (FIG. 15). Mice were treated at 6 weeks and monitored at 7 and 10 weeks by neuroimaging. Treatment of CD mice with rAAV-ASPA also restores the myelin lipid profile, as evidenced by measurement of sphingolipids in treated and control mice (FIG. 16).

A crucial finding is that high ubiquitous ASPA expression enhances motor performance in treated CD mice over wild-type mice. This may be the result of enhanced energy metabolism due to direct intervention in the ASPA-mediated metabolism of NAA.

The results from this global metabolomic study compare WT or aspartoacylase (ASPA) KO brain samples, or KO mice treated with recombinant AAV (to express ASPA or not, as control), including changes in metabolites related to energetics (carbohydrate and lipid metabolism), neurotransmitter production, inflammation, and redox homeostasis. In the principal component analysis (PCA), samples split into two groups, with WT and rAAV Tx in one, and KO and rAAV Ctrl in the other, suggesting rAAV Tx-mediated "rescued" metabolomic effects of ASPA deficiency. Consistent with loss of ASPA function, N-acetylaspartate (NAA) accumulated in brain (KO vs WT), while levels decreased following ASPA re-expression (rAAV Tx vs Ctrl). Lipids tended to show decreases across all classes, which could reflect changes in beta-oxidation and/or biosynthesis (KO vs WT); rAAV Tx (compared to rAAV Ctrl) showed increases in a marker of lipid biosynthesis, with increases in a number of lipid classes. Evidence of declining glycolytic use in KO (compared to WT) was reversed in rAAV Tx (compared to rAAV Control). Finally, changes in the dataset pointed to increasing inflammation and oxidative stress in KO (compared to WT), with decreases in rAAV Tx (compared to Ctrl).

Summary of Results
Regarding Gene Therapy:

Gene Therapy reverses the metabolic changes in Canavan disease brains.

Regarding Canavan Disease Pathomechanism and CNS Energy Metabolism:

1. Glucose metabolism in Canavan brains
   a. Substrates for glycolysis are abundant in Canavan mouse brains
      i. Substrates of glycolysis accumulate (e.g. glucose, glucose-6-phosphate, 3-phosphoglycerate, phosphoenolpyruvate) indicating a decreased rate of glycolysis.
      ii. Increased phosphoenolpyruvate inhibits the enzyme "triosephosphate isomerase" which decreases the efficacy of glycolysis by utilizing only 50% of each glucose molecule for energy production.
      iii. Glycogen, the glucose storage system of cells, is being broken down despite the abundancy of glucose in Canavan mouse brains. In a physiologic state, increased glucose leads to glycogen synthesis not break down.
   b. Products of glycolysis are unchanged or decreased in Canavan mouse brains
      i. Pyruvate is unchanged despite the abundancy of glycolysis substrates, which is paralleled by an decrease in lactate. Both indicates that the glycolytic rate is decreased.
2. Fatty acid metabolism in Canavan brains
   a. Products of fatty acid break down are changed to favor beta-oxidation (use of fatty acids for energy production).
      i. Carnitine is increased in Canavan brains. The transport into mitochondria is the rate limiting step in beta-oxidation. This transport is conducted by Carnitine palmitoyltransferase 1 and 2 (CPT1 and CPT2). Fatty acids need to be bound to carnitine in order to be transported into mitochondria. An increase in carnitine usually facilitates the esterification of fatty acids and carnitine supported fatty acid transport into mitochondria.
      ii. Several carnitine esters are increased, decreased or unchanged indicating consumption of fatty acids in Canavan brains.
      iii. Several fatty acids are decreased as well in Canavan brains, which might be because of fatty acid consumption for energy production, e.g. ATP or other energy equivalents.
      iv. Malonylcarnitine, a surrogate marker for malonyl-CoA is decreased which facilitates fatty acid transport into mitochondria for beta-oxidation (Malonyl-CoA inhibits CPT1 and thus reduces fatty acid transport into mitochondria; a reduction in malonyl-CoA removed this inhibitory stimulus). Malonyl-CoA is also a precursor for fatty acid synthesis and thus mediates between fatty acid break down and fatty acid synthesis. The fact that malonylcarnitine is decreased points towards fatty acid break down.
3. Ketone bodies in Canavan brains
   a. The ketone body beta-hydroxybutyrate is increased, which is directly broken down to acetate and feed into the TCA cycle.
   b. Beta-hydroxybutyrate also mediates between metabolism and transcription.
4. Acetate in Canavan brains
   a. Acetyl-CoA is not changed in the CD neurometabolome, which argues against the "acetate deficiency hypothesis". In addition, it might also explain why acetate supplementation failed to cure Canavan disease in patients.
   b. Acetylcarnitine, which has been reported to be crucial in energy production is highly increased and thus facilitates energy production.
5. Antioxidants
   a. Some antioxidants were decreased, some increased, which could support the oxidative stress hypothesis. However, there was a significant reduction in metabolites for the synthesis of antioxidants, suggesting that the decreased in some antioxidants is an issue of supply rather than demand. This argues against the oxidative stress hypothesis as a primary disease causing factor.

NAA accumulation and/or ASPA deficiency disrupt the CNS energy metabolism by favoring fatty acids over glucose/lactate for energy production, causing "self-consumption" of fatty acids, critical components of myelin and thus white matter vacuolations and disease pathology.

NAA metabolic deficiency and/or its causative ASPA deficiency might promote fatty acid over glucose/lactate consumption for energy production.

NAA metabolism with its associated proteins such as AspA, might be a key player in regulating and communication between metabolic pathways and monitoring metabolic homeostasis of cells and organs, which is demonstrated by the fact that despite the abundancy of glucose, fatty acid metabolism is favored, glycogen is broken down and ketone bodies are formed, which are highly detrimental processes in a physiologic system but not in a state of altered NAA/ASPA metabolism. Also, in addition to be involved in NAA metabolism, AspA may play critical roles in energy metabolism.

These conclusions are further supported by the fact that rAAV mediated delivery of ASPA corrects these observed changes.

Example 3

Nur7 Mouse Model of Canavan Disease

A single intravenous (i.v.) injection of recombinant adeno-associated virus (rAAV) expressing human ASPA (hASPA) rescues early lethality and partially restores motor function (1$^{st}$ generation gene therapy) in a CD knock-out (CD KO) mouse, which resembles the congenital sub-form of CD and displays the severest phenotype of all available CD mouse models, with early death at around post-natal day (p) 28.

This example describes a 3$^{rd}$ generation rAAV expressing hASPA (also referred to as FKzhAspA-Opt), which comprises the sequence represented by SEQ ID NO: 1 and cures disease in a CD KO mouse model. Interestingly, the 3$^{rd}$ generation gene therapy turns CD KO mice into "supermice", that outperform wild-type (WT) mice on rotarod motor function test. This rescue is persistent-treated mice assessed at 1.5 years of age still show no signs of disease reoccurrence. CNS pathology and magnet resonance imaging (MRI) at p25 and p365 show complete normalization.

To further support the efficacy of the 3$^{rd}$ generation gene therapy, neurometabolome profiling was performed. Data indicate that over 400 characterized metabolites that showed reversal of the Canavan disease related metabolic changes including myelin associated lipids. Transcriptomic profiling was also performed.

To further evaluate the potency of the 3$^{rd}$ generation gene therapy, different doses and routes of administration were tested. Of note, 200-fold lower doses intraventricularly (ICV) administered rAAV still rescues lethality, while mice treated ICV with 20-fold reduced dose draw even with WT mice on motor function testing.

Figure 17:
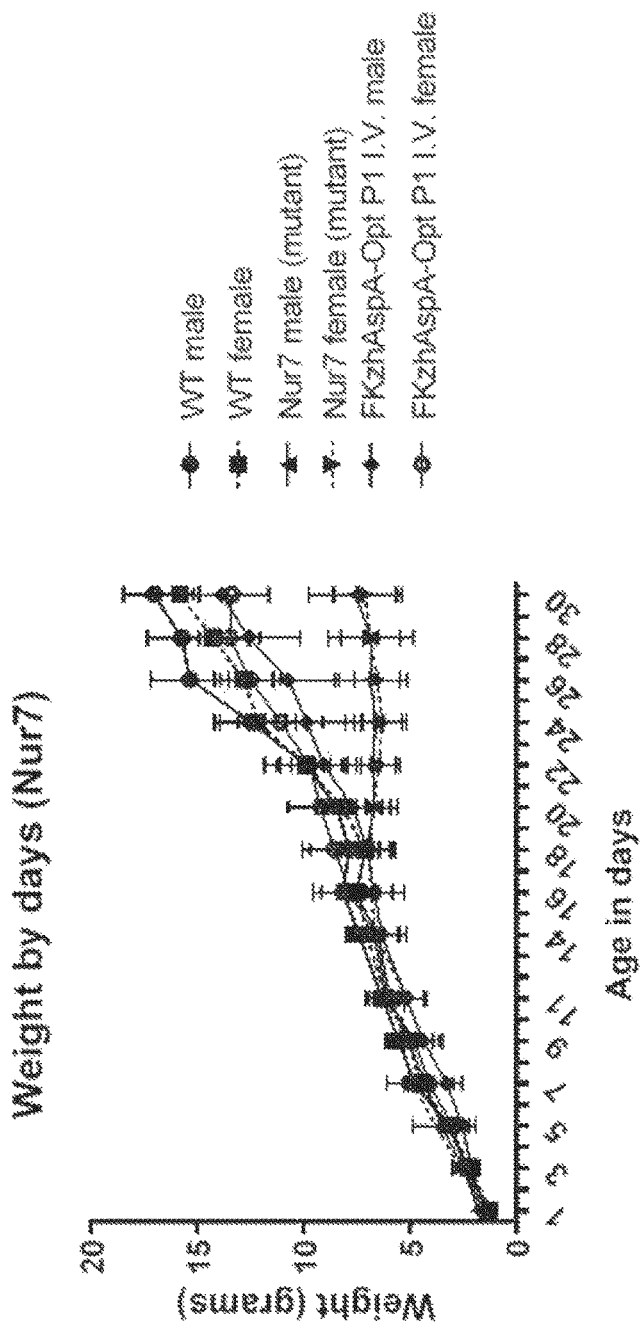
FIG. 17 shows weight loss/gain patterns in wild-type (WT) and mice having a disease associated with a metabolic imbalance (e.g., Nur7). Nur7 mice treated with i.v. administered $3^{rd}$ generation rAAV-hASPA (FKzhAspA-Opt) at P1 show growth similar to WT mice. Male and female mice show the same pattern of weight loss/gain.
Figure 18:
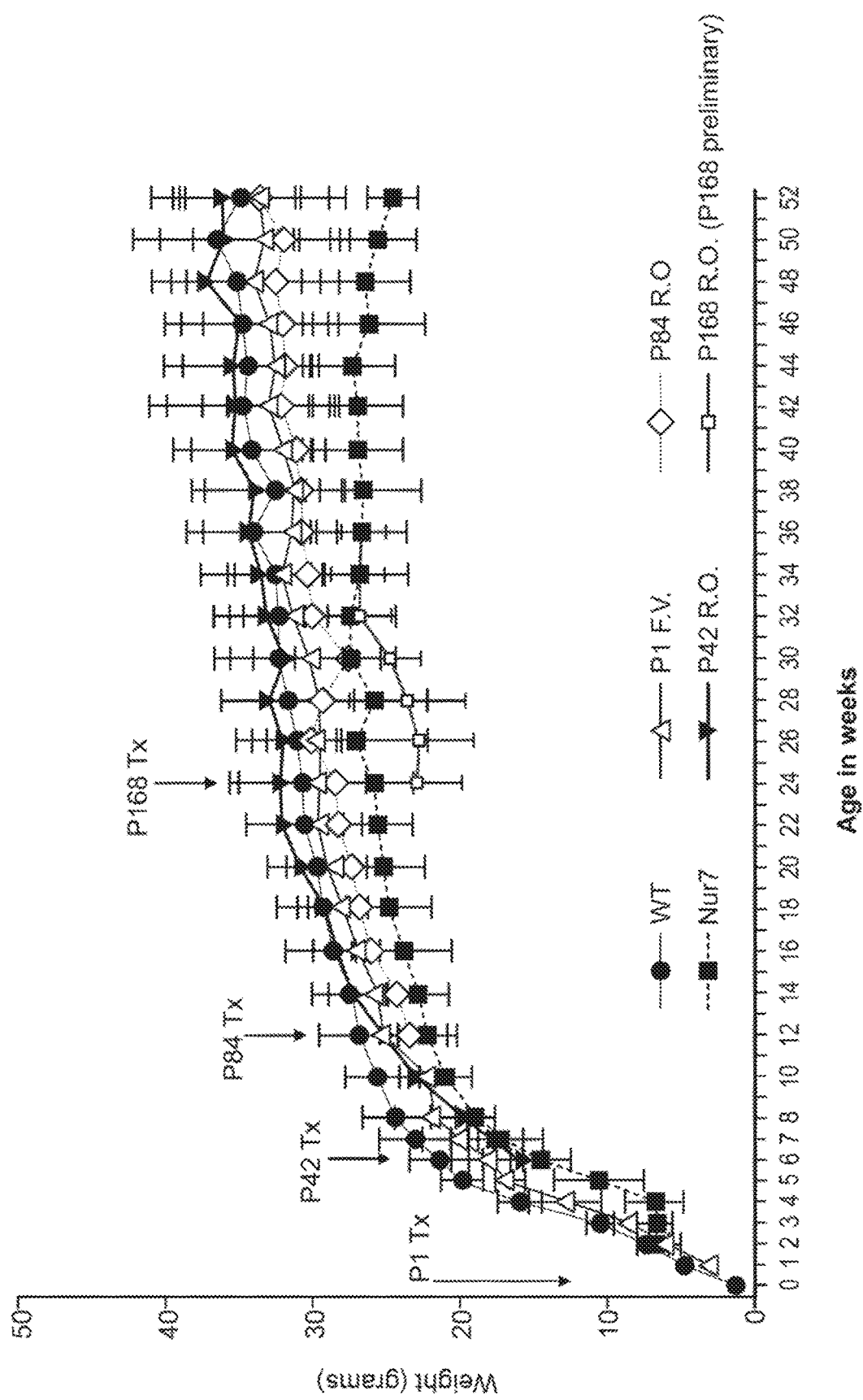
FIG. 18 shows improvement in overall health of mice having a disease associated with a metabolic imbalance (e.g., Nur7) mice treated with rAAV-hASPA. Nur7 mice were treated with rAAV-hASPA at p1, p42, p84, or p168 and weighed. Treated mice were compared to a wild-type (WT) mouse control. All treatment groups show normalization/improvement in weight.

Next, the Nur7 mouse model, which resembles infantile and juvenile sub-form of CD, was tested. This model displays a similar disease pattern as the CD KO mouse with respect to growth curve and neurologic symptoms but eventually re-gains weight and shows survival similar to wild-type mice (FIG. 17). Again, mice received a single i.v. dose of rAAVhASPA at p1 (gold standard positive control) and subsequent groups were dosed at 6, 12, and 24 weeks of age with a dose 10-fold higher than that for neonates to determine the therapeutic window. Of note, mice treated at 6 weeks of age recovered within 4 weeks post-treatment. Mice treated later than 6 weeks require more time to recover but still showed significant improvement over Nur7 mutants (FIG. 18). This recovery was also correlated by CNS pathology and MRI.

Figure 19:
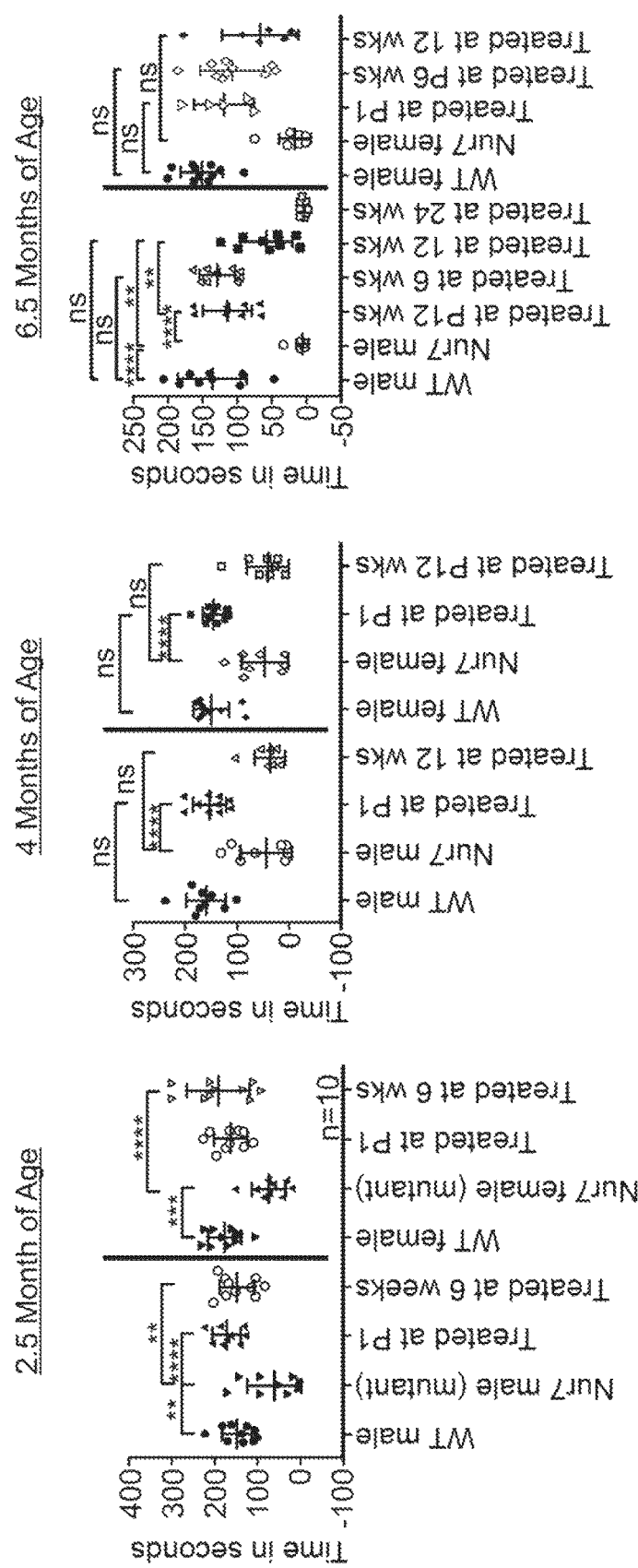
FIG. 19 shows data related to the expanded therapeutic window for treatment of CD using rAAV-hASPA. Nur7 mice treated with rAAV-hASPA at p1, p42, p84 and p168, and motor function was assessed by rotarod. Mice treated at 6 weeks of age recovered completely within 4 weeks post-injection.
Figure 20:
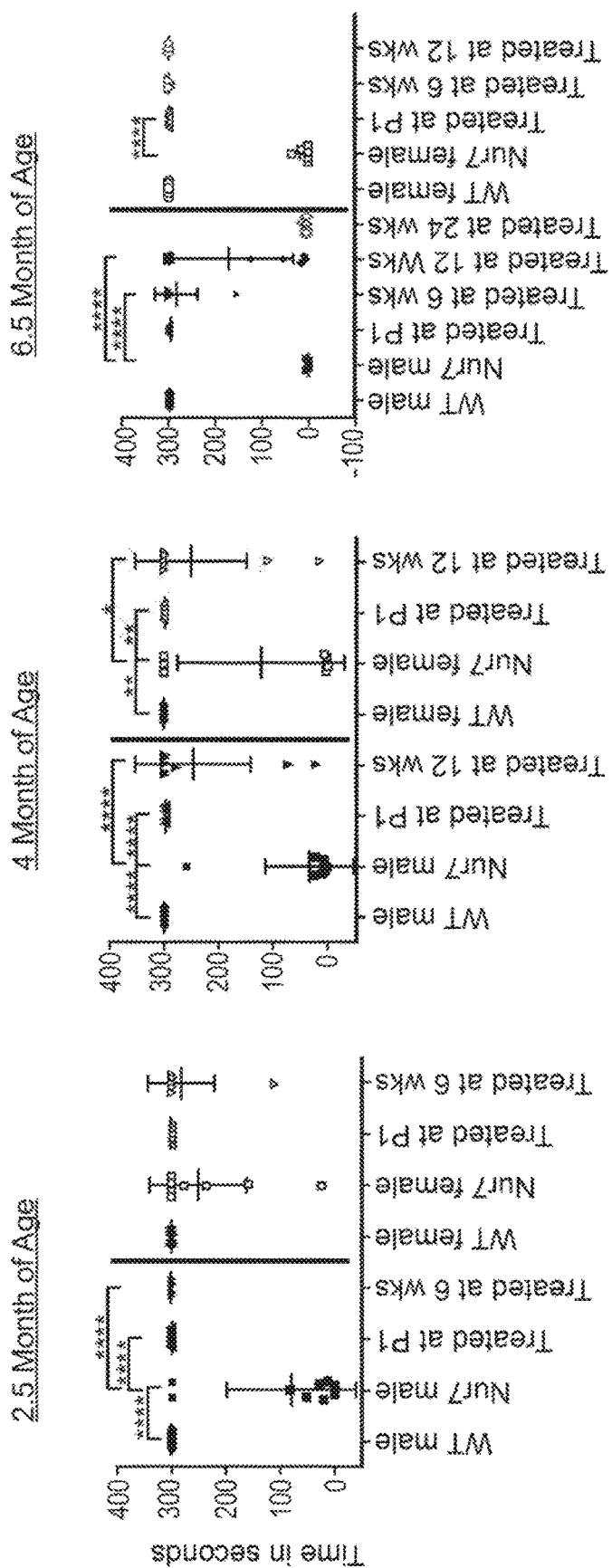
FIG. 20 shows data related to the expanded therapeutic window for treatment of CD using rAAV-hASPA. Nur7 mice treated with rAAV-hASPA at p1, p42, and p84, and motor function was assessed by balance beam.
Figure 21:
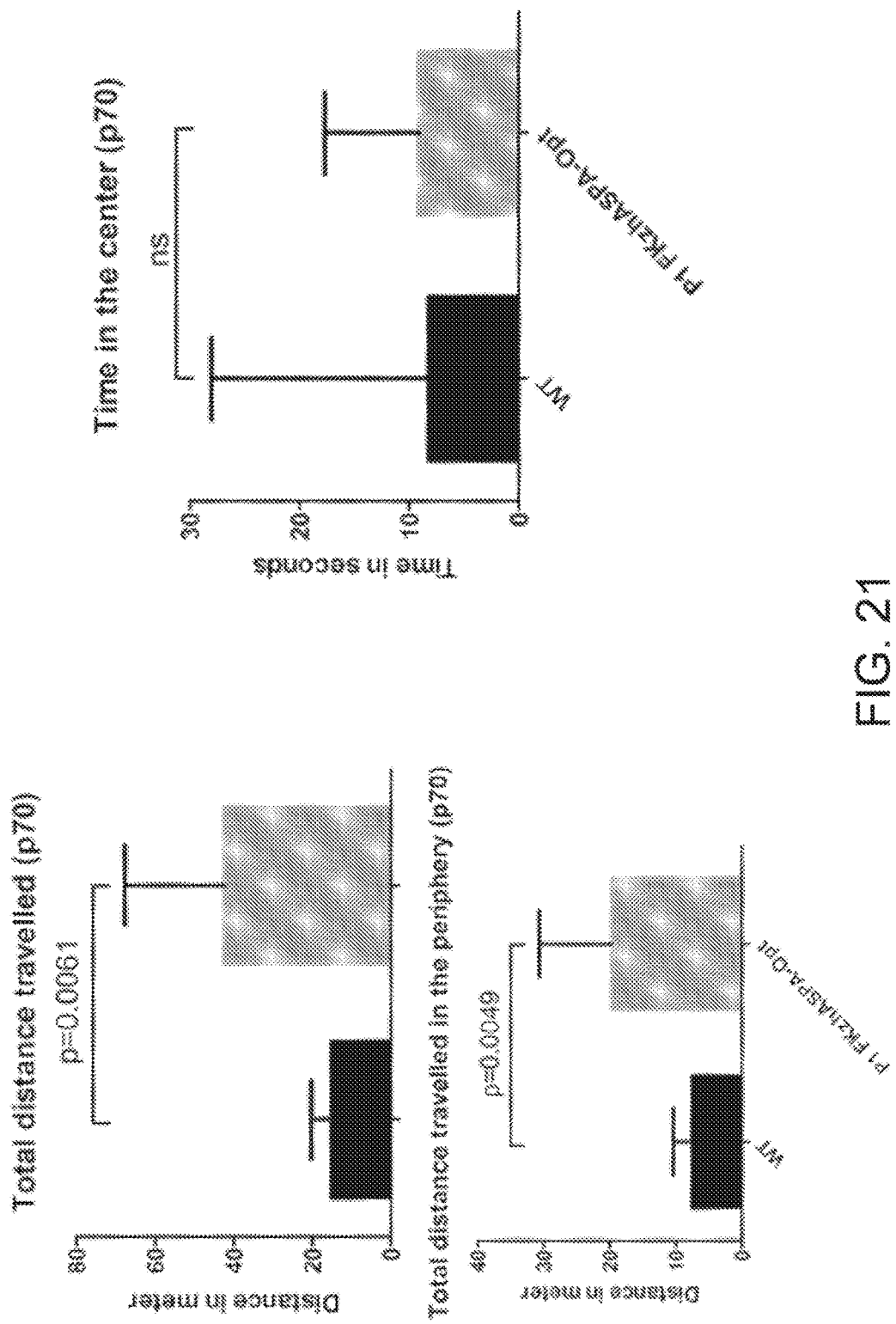
FIG. 21 shows data related to assessment of cognitive function of Nur7 mice treated with rAAV-hASPA. At p'70, Nur7 mice treated with rAAV-hASPA outperformed wild-type (WT) mice with respect to total distance travelled and total distance travelled in the periphery.
Figure 22:
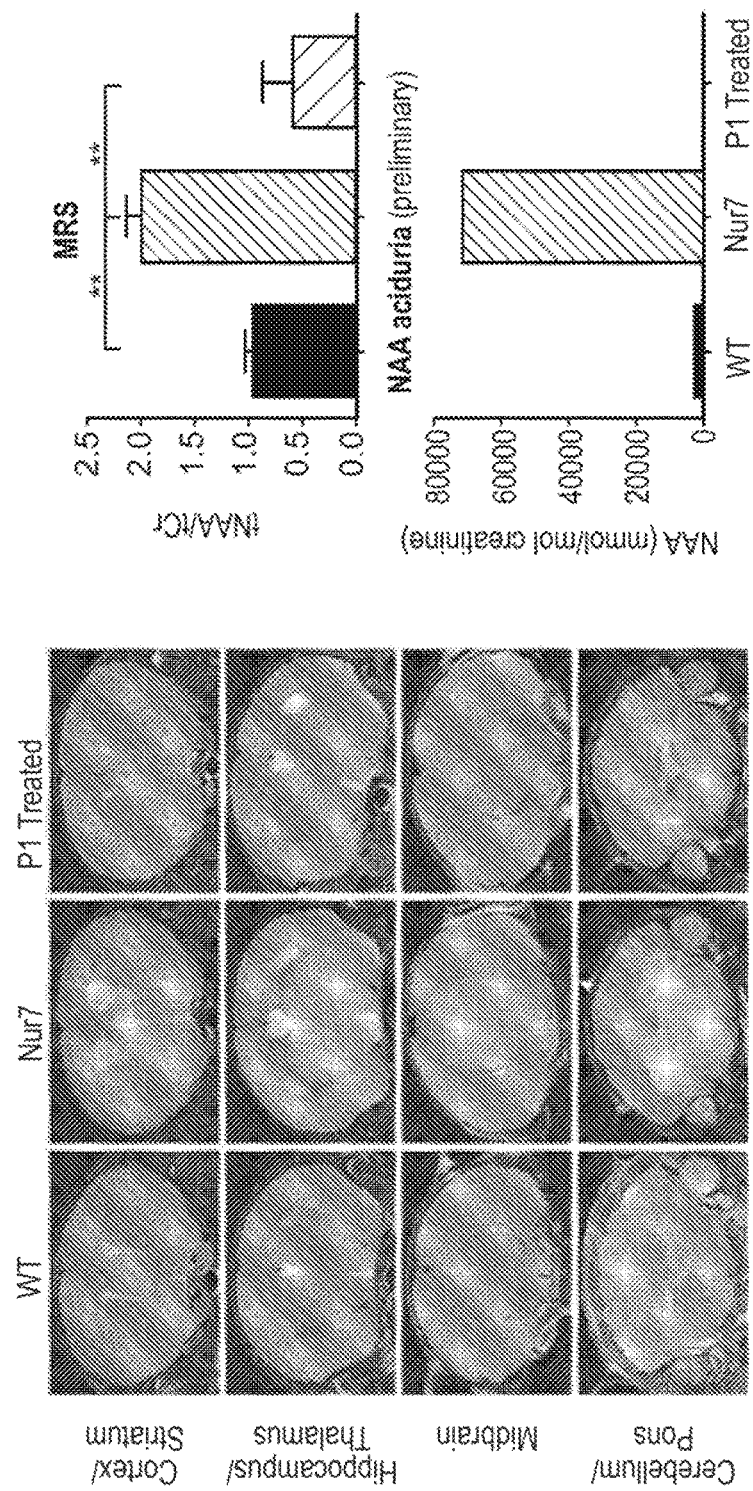
FIG. 22 shows normalization of T2 signal and NAA levels in the brains of Nur7 mice treated with rAAV-hASPA, as shown by magnetic resonance imaging (MRI), magnetic resonance spectroscopy (MRS) and measurement of NAA aciduria.
Figure 23:
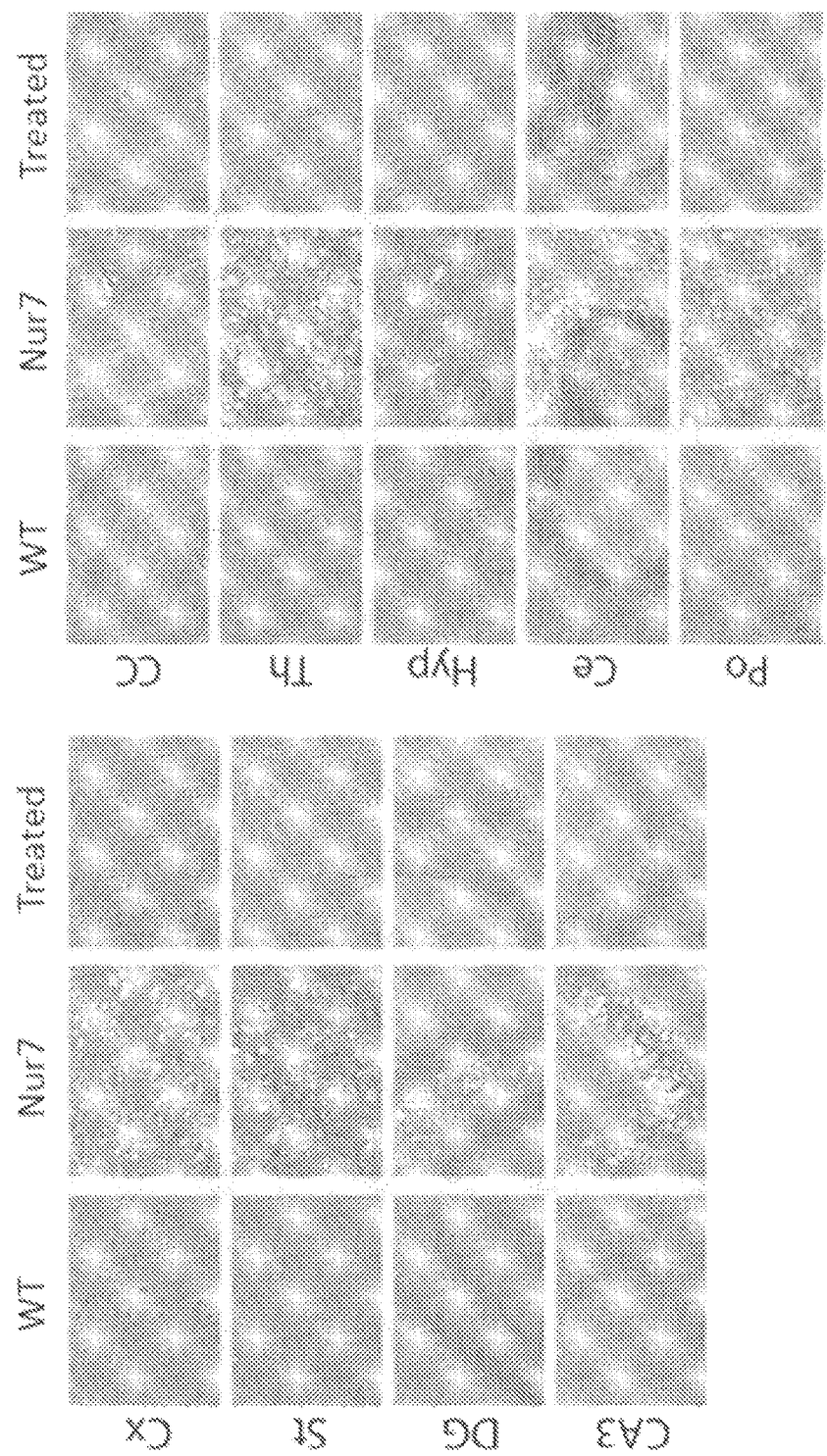
FIG. 23 shows normalization of brain morphology at p25 in Nur7 mice treated with rAAV-hASPA at p1.
Figure 24:
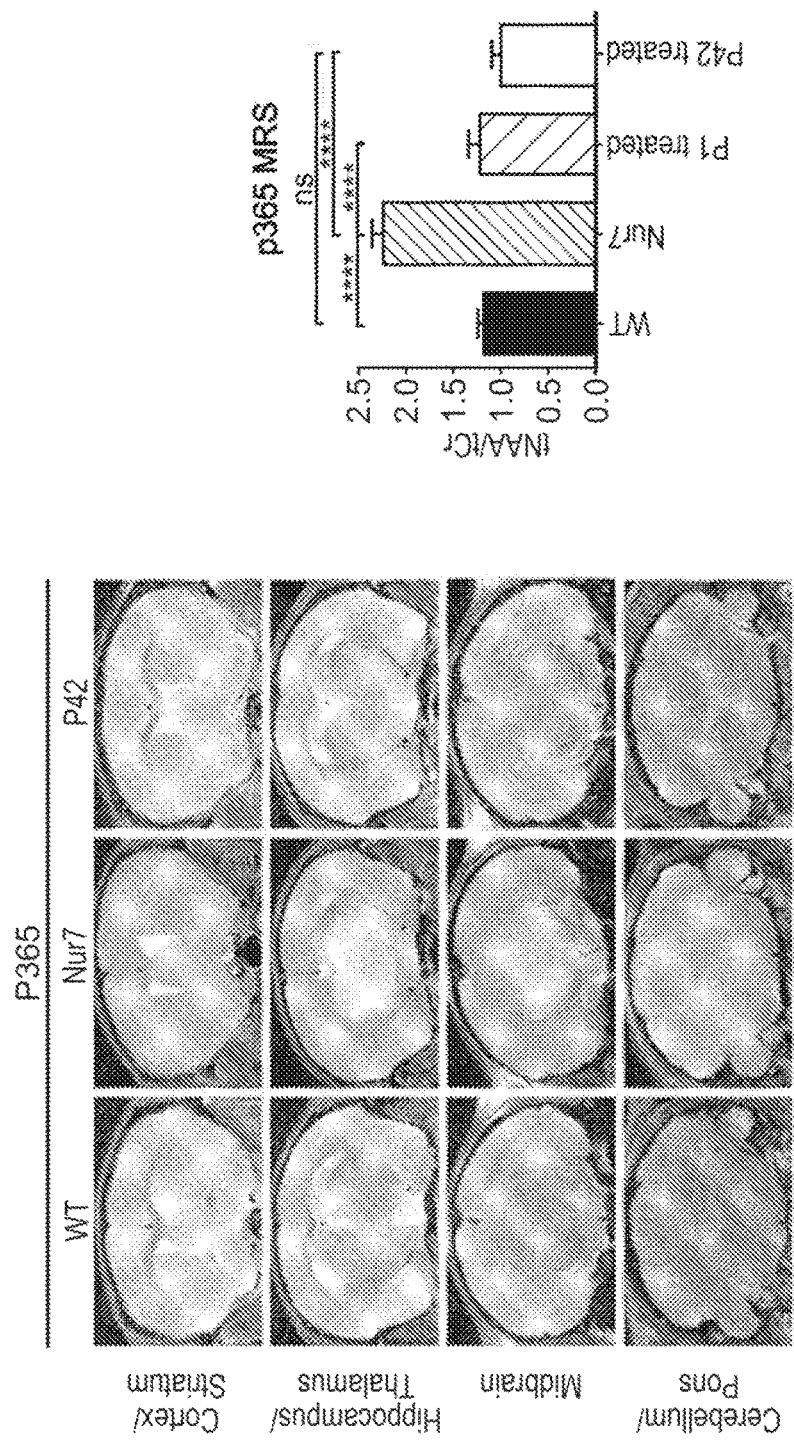
FIG. 24 shows complete normalization of T2 signal intensities and MRS in one-year old Nur7 mice that were treated with rAAV-hASPA at p42.

Motor function was tested for all mice 4 weeks after treatment and subsequent intervals up to one year of age for direct comparison (FIG. 19 and FIG. 20). Generally, the earlier mice were treated, the better the therapeutic outcome. Surprisingly, juvenile mice at 6 weeks of age recovered completely within 4 weeks post-injection (FIG. 19 and FIG. 20). Although mice treated at 3 months of age and older did not respond immediately within the first 4 weeks post-treatment, they eventually showed significant improvements over Nur7 mutant control mice. Cognitive function was also tested; representative data are shown in FIG. 21. Of note, cognitive function testing revealed that treated mice recover cognitively before motor function improves; this was even true for late treatment time points. Furthermore, response to rAAVhASPA gene therapy was confirmed via MRS for N-acetyaspartate, MRI, and neuropathology (FIGS. 22-24).

Overall, data demonstrate that rAAV mediated hASPA expression of the 3$^{rd}$ generation gene therapy vector not only prevents but also rescues the clinical manifestation and pathology of the juvenile and adult model of Canavan disease at an unprecedented level, which might have implications for other CNS disorders that require treatment in later stages of life. In addition, this is confirmed on different levels of cellular complexity by MRI, fMRI, CNS pathology, and neurometabolic profiling.

Example 4

Astrocyte-Restricted hASPA Expression in CD KO Mice (Severe Phenotype)

Several tissue/cell-specific expression cassettes configured for restricting hASPA expression to either astrocytes, neurons, oligodendrocytes, liver, heart, or muscle were produced. For example, a rAAV-hASPA construct comprising an astrocyte-specific glial fibrillary acidic protein (GFAP) promoter was produced. Tissue-restricted rAAV were administered to Canavan disease knock-out (CD KO) mice. Surprisingly, mice expressing hASPA restricted to peripheral organs showed extended survival and normalization of the growth curve at later time points, suggesting a contribution of peripheral organs to the disease pathomechanism.

Figure 25:
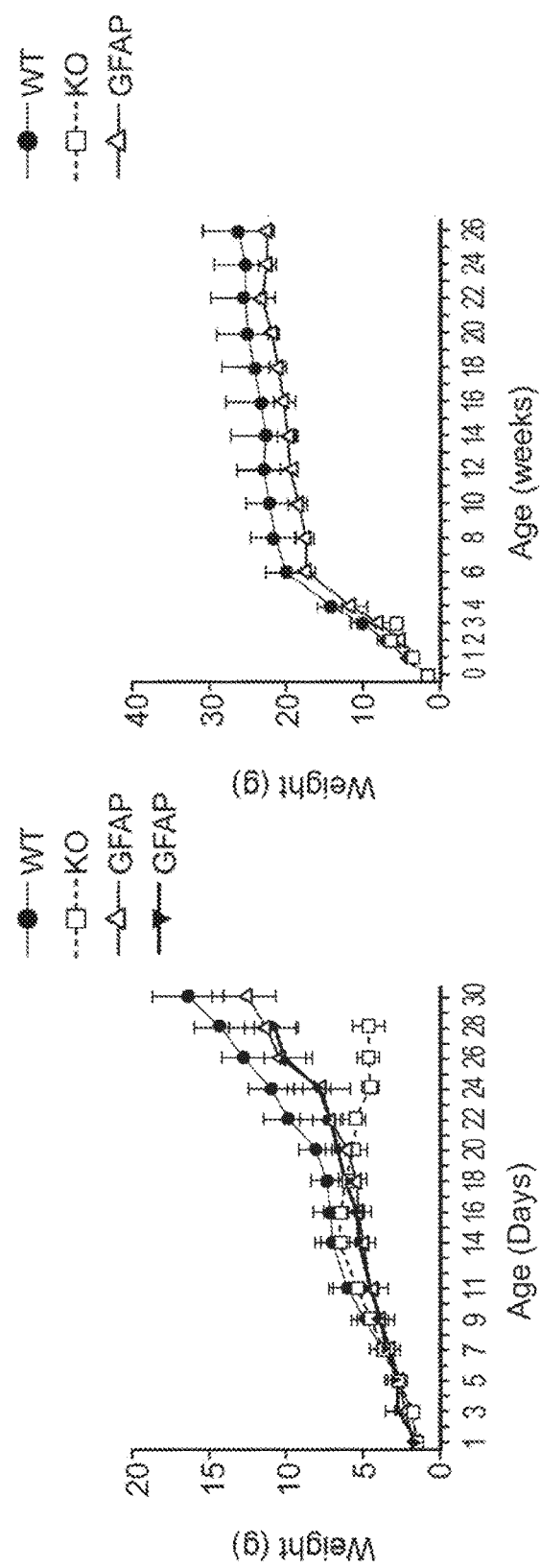
FIG. 25 shows improvement in overall health, as measured by weight gain, in mice having a disease associated with a metabolic imbalance (e.g., CD KO mice) treated with astrocyte-restricted rAAV-hASPA. The astrocyte-specific expression of ASPA was produced by using a glial fibrillary acidic protein (GFAP) promoter to drive hASPA expression. The lifespan of mice having a disease associated with a metabolic imbalance (e.g., CD KO mice) treated with astrocyte-restricted rAAV-hASPA extended beyond the 28 day lifespan of untreated mice having a disease associated with a metabolic imbalance, and was not significantly different from the lifespan of wild-type (WT) mice.
Figure 27:
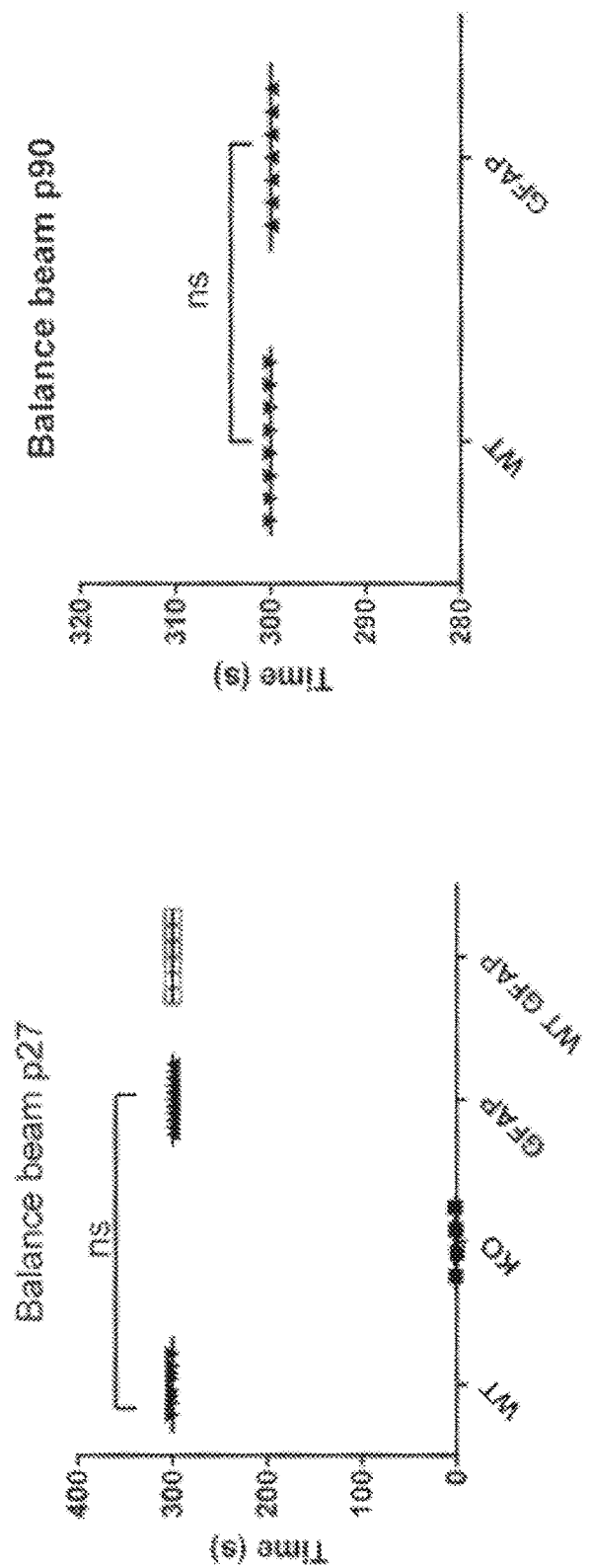
FIG. 27 shows astrocyte-restricted expression of hASPA results in normalization of motor function in CD KO mice. CD KO mice were administered astrocyte-restricted rAAV-hASPA and motor function was measured by a balance beam test at p27 and p90. Data show that astrocyte-restricted expression of hASPA resulted in restoration of motor function in treated CD KO mice compared to wild-type (WT) mice.

Astrocyte-restricted hASPA expression produced the strongest disease recovery matching the performance of wild-type (WT) mice (FIGS. 25-27). FIG. 25 shows astrocyte-restricted expression of hASPA results in survival and growth of treated CD KO mice compared to untreated control mice. FIG. 26 shows astrocyte-restricted expression of hASPA results in restoration of motor function in treated CD KO mice, as measured by rotarod test at p27 and p90. FIG. 27 shows astrocyte-restricted expression of hASPA results in restoration of motor function in treated CD KO mice, as measured by balance beam test at p27 and p90.

Figure 28:
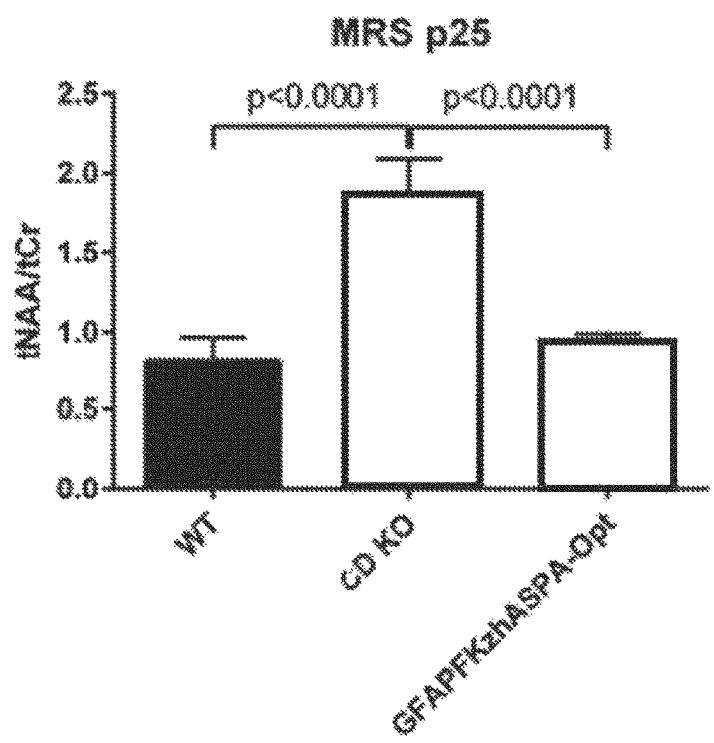
FIG. 28 shows astrocyte-restricted expression of hASPA normalizes NAA levels, as measured by MRS.

A lower dose of rAAV-hASPA was administered to mice via localized brain injections. Data indicates localized T2 hyper-intensity signal clearance on MRI was well correlated with reduction of NAA levels by MRS (FIG. 28). In other words, the further away from the injection site, the higher the NAA levels, which supports the idea of drainage and hydrolytic activity of NAA towards the injection side. Currently, we are investigating this metabolic sink theory in more detail by creating a functional map of therapeutic gene transfer in the brain by mass spectrometry quantification of NAA, and vector genome and ASPA transcripts analyses in 5 different anatomic regions.

Overall, data indicate that hASPA expression does not have to be restored in oligodendrocytes in order to rescue lethality and Canavan disease phenotype.

SEQUENCES

>SEQ ID NO: 1-Codon-optimized human aspartoacylase
(hASPA) cDNA (full Kozak sequence underlined)
GCCACCATGACAAGCTGCCACATCGCCGAGGAGCACATCCAGAAAGTCGC
CATTTTTGGGGGAACTCACGGTAACGAACTCACAGGGGTCTTCCTGGTGA
AGCACTGGCTCGAGAACGGCGCAGAAATCCAGAGAACCGGACTGGAGGTG
AAACCCTTCATTACAAATCCTCGGGCCGTCAAGAAATGCACTCGCTACAT
CGACTGTGATCTGAACCGGATTTTTGATCTGGAAAATCTCGGCAAGAAAA
TGTCCGAGGACCTGCCATACGAAGTGAGGAGAGCTCAGGAGATCAACCAC
CTCTTCGGACCCAAGGACAGCGAAGATTCCTATGACATCATTTTTGATCT
GCATAACACCACATCAAATATGGGGTGCACCCTGATCCTCGAGGACAGCC
GCAACAATTTCCTGATCCAGATGTTTCACTATATTAAGACAAGTCTGGCA
CCACTCCCCTGTTACGTGTATCTGATTGAGCATCCCTCTCTCAAGTACGC
TACTACCCGAAGTATCGCAAAATATCCTGTGGGGATTGAAGTCGGTCCTC
AGCCACAGGGAGTCCTGCGAGCCGATATCCTCGACCAGATGAGGAAGATG
ATCAAACATGCTCTGGATTTCATTCACCACTTCAACGAGGGCAAGGAGTT
CCCCCCTTGCGCCATCGAGGTGTACAAGATCATTGAAAAAGTCGATTATC
CTCGGGACGAGAACGGCGAAATTGCCGCTATCATTCACCCAAATCTGCAG
GACCAGGATTGGAAGCCCCTCCATCCTGGGGATCCAATGTTCCTGACACT
CGACGGTAAAACTATCCCACTGGGCGGAGACTGTACCGTGTACCCCGTGT
TTGTCAATGAGGCAGCCTACTATGAAGAAGAAGCTTTCGCCAAAACA
ACAAAACTCACTCTCAATGCTAAATCTATTCGGTGCTGCCTCCACTGA >SEQ ID NO: 2-Codon-optimized human aspartoacylase
(hASPA)
MTSCHIAEEHIQKVAIFGGTHGNELTGVFLVKHWLENGAEIQRTGLEVKP
FITNPRAVKKCTRYIDCDLNRIFDLENLGKKMSEDLPYEVRRAQEINHLF
GPKDSEDSYDIIFDLHNTTSNMGCTLILEDSRNNFLIQMFHYIKTSLAPL
PCYVYLIEHPSLKYATTRSIAKYPVGIEVGPQPQGVLRADILDQMRKMIK
HALDFIHHFNEGKEFPPCAIEVYKIIEKVDYPRDENGEIAAIIHPNLQDQ
DWKPLHPGDPMFLTLDGKTIPLGGDCTVYPVFVNEAAYYEKKEAFAKTTK
LTLNAKSIRCCLH >SEQ ID NO: 3-Codon-optimized human NAT8L cDNA
(full Kozak sequence underlined)
GCCACCATGCACTGCGGGCCACCTGATATGGTCTGTGAAACTAAGATTGT
CGCTGCCGAGGATCACGAGGCTCTGCCTGGAGCTAAAAAAGATGCTCTGC
TGGCCGCCGCCGGCGCCATGTGGCCCCCTCTGCCAGCAGCACCAGGACCA
GCAGCAGCACCACCCGCCCCTCCACCCGCCCCTGTGGCCCAGCCACACGG
CGGCGCCGGCGGCGCCGGCCCTCCAGGCGGCCGGGGCGTGTGCATCCGGG
AGTTCAGAGCAGCAGAGCAGGAGGCAGCAAGGAGAATCTTTTATGACGGC
ATCATGGAGCGGATCCCCAACACCGCCTTCAGGGGACTGAGGCAGCACCC
TAGAGCACAGCTGCTGTACGCACTGCTGGCCGCCCTGTGCTTTGCCGTGA
GCAGGTCCCTGCTGCTGACCTGTCTGGTGCCCGCCGCCCTGCTGGGACTG
AGGTACTATTACAGCCGGAAAGTGATCAGAGCCTATCTGGAGTGCGCCCT
GCACACAGACATGGCCGATATCGAGCAGTATTACATGAAGCCCCCTGGCT
CCTGTTTCTGGGTGGCCGTGCTGGACGGGAAACGTGGTGGGAATCGTGGCA
GCAAGGGCACACGAGGAGGACAATACCGTGGAGCTGCTGCGCATGTCTGT
GGATAGCAGGTTCCGCGGCAAGGGAATCGCAAAGGCCCTGGGAAGGAAGG
TGCTGGAGTTTGCCGTGGTGCACAATTACTCTGCCGTGGTGCTGGGCACC
ACAGCAGTGAAGGTGGCAGCCCACAAGCTGTATGAGTCCCTGGGCTTTAG
GCACATGGGCGCCTCTGATCACTACGTGCTGCCTGGCATGACACTGTCCC
TGGCCGAGAGACTGTTCTTCCAGGTCCGCTACCATAGATATAGACTGCAG
CTGAGGGAGGAGTGA >SEQ ID NO: 4-Codon-optimized human NAT8L
MHCGPPDMVCETKIVAAEDHEALPGAKKDALLAAAGAMWPPLPAAPGPAA
APPAPPPAPVAQPHGGAGGAGPPGGRGVCIREFRAAEQEAARRIFYDGIM
ERIPNTAFRGLRQHPRAQLLYALLAALCFAVSRSLLLTCLVPAALLGLRY
YYSRKVIRAYLECALHTDMADIEQYYMKPPGSCFWVAVLDGNVVGIVAAR
AHEEDNTVELLRMSVDSRFRGKGIAKALGRKVLEFAVVHNYSAVVLGTTA
VKVAAHKLYESLGFRHMGASDHYVLPGMTLSLAERLFFQVRYHRYRLQLR
EE

---

What is claimed is:

1. A method for treating a disease associated with a metabolic imbalance in a subject in need thereof, the method comprising:
    administering to the subject a recombinant adeno-associated virus (rAAV) comprising a nucleic acid molecule, wherein the nucleic acid molecule comprises the sequence according to SEQ ID NO: 1 encoding aspartoacylase (ASPA),
    wherein the disease is associated with a metabolic imbalance comprising a shift from beta-oxidation to glycolysis in the subject,
    wherein the disease is a cancer.

2. The method of claim 1, wherein the rAAV comprises a capsid protein of AAV serotype AAV9, or a variant thereof.

3. The method of claim 1, wherein the nucleic acid molecule further comprises sequences encoding 5' and 3' inverted terminal repeats of serotype AAV2.

4. The method of claim 1, wherein the nucleic acid molecule is operably linked to a promoter selected from the group consisting of a cytomegalovirus (CMV) promoter, a β-actin promoter, a CNS-specific promoter, a retroviral Rous sarcoma virus (RSV) LTR promoter, an SV40 promoter, a dihydrofolate reductase promoter, a phosphoglycerol kinase (PGK) promoter, and an EF1a promoter.

5. The method of claim 4, wherein the nucleic acid molecule is operably linked to a β-actin promoter.

6. The method of claim 1, wherein administration of the rAAV results in expression of ASPA in a target tissue.

7. The method of claim 6, wherein the target tissue comprises tumor tissue.

8. The method of claim 1, wherein the cancer is ovarian cancer, breast cancer, lung squamous cell carcinoma, kidney renal cell carcinoma, colorectal cancer, prostate cancer, uterine endometroid cancer, glioma, or melanoma.

9. The method of claim 8, wherein the cancer is glioma.

10. The method of claim 1, further comprising, prior to administering the rAAV to the subject, identifying the metabolic imbalance based at least in part upon a metabolic profile of a biological sample obtained from the subject.

11. The method of claim 10, wherein the biological sample is a tissue sample.

12. The method of claim 11, wherein the tissue sample comprises a tumor or tumor cells.

13. The method of claim 10, wherein the metabolic profile is measured using liquid chromatography, mass spectrometry, or liquid chromatography/mass spectrometry.

14. The method of claim 10, wherein the metabolic profile comprises a level of a biomarker selected from the group consisting of glucose, glucose-6-phosphate, 3-phosphoglycerate, pyruvate, lactate, and phosphoenolpyruvate.

15. The method of claim 10, wherein the metabolic profile comprises a level of a biomarker selected from the group consisting of carnitine, malonylcarnitine, myristoylcarnitine, palmitoylcarnitine, malonylcarnitine, and beta-hydroxybutyrate.

16. The method of claim 10, wherein the metabolic profile comprises a level of a biomarker indicating an increase in glycolysis in the subject.

17. The method of claim 1, wherein the rAAV is administered to the subject via injection.

18. The method of claim 1, wherein the rAAV is administered to the subject intravascularly.

* * * * *

SEQUENCE LISTING

<160> NUMBER OF SEQ ID NOS: 4

<210> SEQ ID NO 1
<211> LENGTH: 948
<212> TYPE: DNA
<213> ORGANISM: Artificial Sequence
<220> FEATURE:
<223> OTHER INFORMATION: Synthetic Polynucleotide

<400> SEQUENCE: 1
gccaccatga caagctgcca catcgccgag gagcacatcc agaaagtcgc cattttttggg      60 ggaactcacg gtaacgaact cacaggggtc ttcctggtga agcactggct cgagaacggc     120
gcagaaatcc agagaaccgg actggaggtg aaaccttca ttacaaatcc tcgggccgtc      180
aagaaatgca ctcgctacat cgactgtgat ctgaaccgga tttttgatct ggaaaatctc     240
ggcaagaaaa tgtccgagga cctgccatac gaagtgagga gagctcagga gatcaaccac     300
ctcttcggac ccaaggacag cgaagattcc tatgacatca tttttgatct gcataacacc     360
acatcaaata tggggtgcac cctgatcctc gaggacagcc gcaacaattt cctgatccag     420
atgtttcact atattaagac aagtctggca ccactcccct gttacgtgta tctgattgag     480
catccctctc tcaagtacgc tactacccga agtatcgcaa aatatcctgt ggggattgaa     540
gtcggtcctc agccacaggg agtcctgcga gccgatatcc tcgaccagat gaggaagatg     600
atcaaacatg ctctggattt cattcaccac ttcaacgagg gcaaggagtt cccccccttgc    660 gccatcgagg tgtacaagat cattgaaaaa gtcgattatc ctcgggacga gaacggcgaa     720

```
attgccgcta tcattcaccc aaatctgcag gaccaggatt ggaagcccct ccatcctggg    780
gatccaatgt tcctgacact cgacggtaaa actatcccac tgggcggaga ctgtaccgtg    840
taccccgtgt tgtcaatga ggcagcctac tatgagaaga agaagctttt cgccaaaaca    900
acaaaactca ctctcaatgc taaatctatt cggtgctgcc tccactga               948
```

<210> SEQ ID NO 2
<211> LENGTH: 313
<212> TYPE: PRT
<213> ORGANISM: Artificial Sequence
<220> FEATURE:
<223> OTHER INFORMATION: Synthetic Polypeptide

<400> SEQUENCE: 2

```
Met Thr Ser Cys His Ile Ala Glu Glu His Ile Gln Lys Val Ala Ile
1               5                   10                  15

Phe Gly Gly Thr His Gly Asn Glu Leu Thr Gly Val Phe Leu Val Lys
                20                  25                  30

His Trp Leu Glu Asn Gly Ala Glu Ile Gln Arg Thr Gly Leu Glu Val
            35                  40                  45

Lys Pro Phe Ile Thr Asn Pro Arg Ala Val Lys Lys Cys Thr Arg Tyr
        50                  55                  60

Ile Asp Cys Asp Leu Asn Arg Ile Phe Asp Leu Glu Asn Leu Gly Lys
65                  70                  75                  80

Lys Met Ser Glu Asp Leu Pro Tyr Glu Val Arg Arg Ala Gln Glu Ile
                85                  90                  95

Asn His Leu Phe Gly Pro Lys Asp Ser Glu Asp Ser Tyr Asp Ile Ile
            100                 105                 110

Phe Asp Leu His Asn Thr Thr Ser Asn Met Gly Cys Thr Leu Ile Leu
        115                 120                 125

Glu Asp Ser Arg Asn Asn Phe Leu Ile Gln Met Phe His Tyr Ile Lys
130                 135                 140

Thr Ser Leu Ala Pro Leu Pro Cys Tyr Val Tyr Leu Ile Glu His Pro
145                 150                 155                 160

Ser Leu Lys Tyr Ala Thr Thr Arg Ser Ile Ala Lys Tyr Pro Val Gly
                165                 170                 175

Ile Glu Val Gly Pro Gln Pro Gln Gly Val Leu Arg Ala Asp Ile Leu
            180                 185                 190

Asp Gln Met Arg Lys Met Ile Lys His Ala Leu Asp Phe Ile His His
        195                 200                 205

Phe Asn Glu Gly Lys Glu Phe Pro Pro Cys Ala Ile Glu Val Tyr Lys
    210                 215                 220

Ile Ile Glu Lys Val Asp Tyr Pro Arg Asp Glu Asn Gly Glu Ile Ala
225                 230                 235                 240

Ala Ile Ile His Pro Asn Leu Gln Asp Gln Asp Trp Lys Pro Leu His
                245                 250                 255

Pro Gly Asp Pro Met Phe Leu Thr Leu Asp Gly Lys Thr Ile Pro Leu
            260                 265                 270

Gly Gly Asp Cys Thr Val Tyr Pro Val Phe Val Asn Glu Ala Ala Tyr
        275                 280                 285

Tyr Glu Lys Lys Glu Ala Phe Ala Lys Thr Thr Lys Leu Thr Leu Asn
    290                 295                 300

Ala Lys Ser Ile Arg Cys Cys Leu His
305                 310
```

<210> SEQ ID NO 3
<211> LENGTH: 915
<212> TYPE: DNA
<213> ORGANISM: Artificial Sequence
<220> FEATURE:
<223> OTHER INFORMATION: Synthetic Polynucleotide

<400> SEQUENCE: 3

```
gccaccatgc actgcgggcc acctgatatg gtctgtgaaa ctaagattgt cgctgccgag      60
gatcacgagg ctctgcctgg agctaaaaaa gatgctctgc tggccgccgc cggcgccatg     120
tggccccctc tgccagcagc accaggacca gcagcagcac cacccgcccc tccacccgcc     180
cctgtggccc agccacacgg cggcgccggc ggcgccggcc ctccaggcgg ccggggcgtg     240
tgcatccggg agttcagagc agcagagcag gaggcagcaa ggagaatctt ttatgacggc     300
atcatggagc ggatccccaa caccgccttc aggggactga ggcagcaccc tagagcacag     360
ctgctgtacg cactgctggc cgccctgtgc tttgccgtga caggtccct gctgctgacc     420
tgtctggtgc ccgccgccct gctgggactg aggtactatt acagccggaa agtgatcaga     480
gcctatctgg agtgcgccct gcacacagac atggccgata tcgagcagta ttacatgaag     540
ccccctggct cctgttcctg gtggccgtg ctggacggaa acgtggtggg aatcgtggca     600
gcaagggcac acgaggagga caataccgtg gagctgctgc gcatgtctgt ggatagcagg     660
ttccgcggca aggaatcgc aaaggccctg gaaggaagg tgctggagtt tgccgtggtg     720
cacaattact ctgccgtggt gctgggcacc acagcagtga aggtggcagc ccacaagctg     780
tatgagtccc tgggctttag gcacatgggc gcctctgatc actacgtgct gcctggcatg     840
acactgtccc tggccgagag actgttcttc caggtccgct accatagata tagactgcag     900
ctgagggagg agtga                                                      915
```

<210> SEQ ID NO 4
<211> LENGTH: 302
<212> TYPE: PRT
<213> ORGANISM: Artificial Sequence
<220> FEATURE:
<223> OTHER INFORMATION: Synthetic Polypeptide

<400> SEQUENCE: 4

```
Met His Cys Gly Pro Pro Asp Met Val Cys Glu Thr Lys Ile Val Ala
1               5                   10                  15

Ala Glu Asp His Glu Ala Leu Pro Gly Ala Lys Lys Asp Ala Leu Leu
            20                  25                  30

Ala Ala Ala Gly Ala Met Trp Pro Leu Pro Ala Ala Pro Gly Pro
        35                  40                  45

Ala Ala Ala Pro Pro Ala Pro Pro Ala Pro Val Ala Gln Pro His
    50                  55                  60

Gly Gly Ala Gly Gly Ala Gly Pro Pro Gly Gly Arg Gly Val Cys Ile
65                  70                  75                  80

Arg Glu Phe Arg Ala Ala Glu Gln Glu Ala Ala Arg Arg Ile Phe Tyr
                85                  90                  95

Asp Gly Ile Met Glu Arg Ile Pro Asn Thr Ala Phe Arg Gly Leu Arg
            100                 105                 110

Gln His Pro Arg Ala Gln Leu Leu Tyr Ala Leu Leu Ala Ala Leu Cys
        115                 120                 125

Phe Ala Val Ser Arg Ser Leu Leu Leu Thr Cys Leu Val Pro Ala Ala
    130                 135                 140
```

-continued

```
Leu Leu Gly Leu Arg Tyr Tyr Ser Arg Lys Val Ile Arg Ala Tyr
145                 150                 155                 160

Leu Glu Cys Ala Leu His Thr Asp Met Ala Asp Ile Glu Gln Tyr Tyr
                165             170                 175

Met Lys Pro Pro Gly Ser Cys Phe Trp Val Ala Val Leu Asp Gly Asn
            180             185                 190

Val Val Gly Ile Val Ala Ala Arg Ala His Glu Glu Asp Asn Thr Val
        195             200                 205

Glu Leu Leu Arg Met Ser Val Asp Ser Arg Phe Arg Gly Lys Gly Ile
        210             215             220

Ala Lys Ala Leu Gly Arg Lys Val Leu Glu Phe Ala Val Val His Asn
225             230             235             240

Tyr Ser Ala Val Val Leu Gly Thr Thr Ala Val Lys Val Ala Ala His
                245             250             255

Lys Leu Tyr Glu Ser Leu Gly Phe Arg His Met Gly Ala Ser Asp His
            260             265             270

Tyr Val Leu Pro Gly Met Thr Leu Ser Leu Ala Glu Arg Leu Phe Phe
            275             280             285

Gln Val Arg Tyr His Arg Tyr Arg Leu Gln Leu Arg Glu Glu
    290             295             300
```